United States Patent
Day et al.

(10) Patent No.: US 6,566,377 B2
(45) Date of Patent: May 20, 2003

(54) β₃ ADRENERGIC RECEPTOR AGONISTS AND USES THEREOF

(75) Inventors: Robert F. Day, Groton, CT (US); Jennifer A. Lafontaine, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/981,551

(22) Filed: Oct. 17, 2001

(65) Prior Publication Data

US 2002/0052392 A1 May 2, 2002

Related U.S. Application Data

(60) Provisional application No. 60/242,274, filed on Oct. 20, 2000.

(51) Int. Cl.⁷ ............... A61K 31/4439; C07D 403/10
(52) U.S. Cl. ............... 514/340; 514/341; 546/271.4; 546/272.1; 546/269.7; 546/275.1; 546/269.1; 546/275.4; 546/272.4
(58) Field of Search ............... 546/271.4, 272.1, 546/269.7, 275.1, 269.1, 275.4, 272.4; 514/340, 341

(56) References Cited

U.S. PATENT DOCUMENTS

| | | | |
|---|---|---|---|
| 4,358,455 A | 11/1982 | Atkinson et al. | 424/263 |
| 5,153,210 A | 10/1992 | Ainsworth et al. | 514/369 |
| 5,977,124 A | 11/1999 | Dow | 514/272 |
| 6,291,491 B1 | 9/2001 | Weber et al. | 514/357 |

FOREIGN PATENT DOCUMENTS

| | | | |
|---|---|---|---|
| EP | 0295828 | 12/1988 | C07D/277/34 |
| EP | 0543662 | 9/1996 | C07C/217/22 |
| WO | WO 9965877 | 12/1999 | C07D/213/80 |
| WO | WO0206258 | 1/2002 | C07D/277/42 |

OTHER PUBLICATIONS

CA 135:242138, Ashton et al. 2001.*
CA 136:134753, Malamas et al. 2002.*

* cited by examiner

*Primary Examiner*—Jane Fan
(74) *Attorney, Agent, or Firm*—Peter C. Richardson; Gregg C. Benson; Arlene K. Musser

(57) ABSTRACT

The instant invention provides β₃ adrenergic receptor agonists of structural Formula (I),

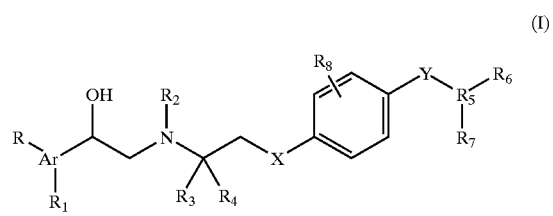

the stereoisomers and prodrugs thereof, and the pharmaceutically acceptable salts of the compounds, stereoisomers and prodrugs, wherein Ar, R, $R_1$, $R_2$, $R_3$, $R_4$, $R_5$, $R_6$, $R_7$, $R_8$, X, and Y, are as defined herein. The invention further provides intermediates useful in the preparation of the compounds of Formula (I), to combinations of the compounds of Formula (I), the stereoisomers and prodrugs thereof, and the pharmaceutically acceptable salts of the compounds, stereoisomers and prodrugs, with anti-obesity agents; to pharmaceutical compositions comprising the compounds of Formula (I), the stereoisomers and prodrugs thereof, and the pharmaceutically acceptable salts of the compounds, stereoisomers and prodrugs, or pharmaceutical compositions comprising the compounds of Formula (I), the stereoisomers and prodrugs thereof, and the pharmaceutically acceptable salts of the compounds, stereoisomers and prodrugs, and anti-obesity agents; and methods of treating β₃ adrenergic receptor-mediated diseases, conditions, or disorders in a mammal which methods comprise administering to the mammal an effective amount of a compound of Formula (I), a stereoisomer or prodrug thereof, or a pharmaceutical composition thereof; or a combination of a compound of Formula (I), a pharmaceutically acceptable salt of the compound, stereoisomer, or prodrug, and an anti-obesity agent, or a pharmaceutical composition thereof.

7 Claims, No Drawings

β₃ ADRENERGIC RECEPTOR AGONISTS AND USES THEREOF

CROSS REFERENCE TO RELATED APPLICATION

This application claims the benefit of U.S. Provisional Application No. 60/242,274 filed Oct. 20, 2000.

FIELD OF THE INVENTION

The present invention relates to compounds of Formula (I) depicted hereinbelow, which compounds are $\beta_3$ adrenergic receptor agonists and, accordingly, have utility as, inter alia, hypoglycemic, and anti-obesity agents.

The invention further relates to intermediates useful in the preparation of the compounds of Formula (I); to combinations of the compounds of Formula (I) with anti-obesity agents; to pharmaceutical compositions comprising such compounds and combinations; and to methods of using the compounds, combinations, and pharmaceutical compositions in the treatment of $\beta_3$ adrenergic receptor-mediated diseases, conditions, or disorders in a mammal. The compounds and combinations of the invention also possess utility for increasing the content of lean meat in edible animals, i.e. ungulate animals such as cattle, swine, and the like, as well as poultry.

The compounds and combinations of this invention further possess utility in the treatment of intestinal motility disorders, depression, prostate disease, dyslipidemia, and airway inflammatory disorders.

BACKGROUND OF THE INVENTION

The disease diabetes mellitus is characterized by metabolic defects in the production and utilization of carbohydrates which result in the failure to maintain appropriate blood sugar levels. The results of these defects include, inter alia, elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type 1 diabetes, or insulin-dependent diabetes mellitus (IDDM), is the result of an absolute deficiency of insulin, the hormone that regulates carbohydrate utilization. Type 2 diabetes, or non-insulin-dependent diabetes mellitus (NIDDM), often occurs with normal, or even elevated, levels of insulin and appears to be the result of the inability of tissues to respond appropriately to insulin. Most Type 2 diabetic patients are also obese.

The compounds of the invention effectively lower blood glucose levels when administered orally to mammals with hyperglycemia or diabetes.

Obesity constitutes a major health risk that leads to mortality and incidence of Type 2 diabetes mellitus, hypertension, and dyslipidemia. In the United States, more than 50% of the adult population is overweight, and almost 25% of the population is considered to be obese. The incidence of obesity is increasing in the United States at a three-percent cumulative annual growth rate. While the vast majority of obesity occurs in the United States and Europe, the prevalence of obesity is also increasing in Japan. Furthermore, obesity is a devastating disease which can also wreak havoc on an individual's mental health and self-esteem, which can ultimately affect a person's ability to interact socially with others. Unfortunately, the precise etiology of obesity is complex and poorly understood, and societal stereotypes and presumptions regarding obesity only tend to exacerbate the psychological effects of the disease. Because of the impact of obesity on society in general, much effort has been expended in efforts to treat obesity, however, success in the long-term treatment and/or prevention thereof remains elusive.

The compounds, pharmaceutical compositions, and combinations of the invention also reduce body weight or decrease weight gain when administered to a mammal. The ability of the compounds to affect weight gain is due to activation of $\beta_3$ adrenergic receptors which stimulate the metabolism of adipose tissue.

β-Adrenergic agents have been generally classified into $\beta_1$, $\beta_2$, and $\beta_3$ receptor-specific subtypes. Agonists of β-receptors promote the activation of adenyl cyclase. Activation of $\beta_1$ receptors invokes an increase in heart rate while activation of $\beta_2$ receptors induces smooth muscle tissue relaxation which produces a drop in blood pressure and the onset of skeletal muscle tremors. Activation of $\beta_3$ receptors is known to stimulate lipolysis (e.g., the breakdown of adipose tissue triglycerides into glycerol and fatty acids) and metabolic rate (energy expenditure), thereby promoting the loss of fat mass. Accordingly, compounds that stimulate $\beta_3$ receptors are therefore useful as anti-obesity agents, and can be further used to increase the content of lean meat in edible animals. In addition, compounds that are $\beta_3$ receptor agonists have hypoglycemic activity, however, the precise mechanism of this effect is presently unknown.

Until recently, $\beta_3$ adrenergic receptors were thought to be found predominantly in adipose tissue, however, $\beta_3$ receptors are now known to be located in such diverse tissues as the intestine, (J. Clin. Invest., 91, 344 (1993)) and the brain Eur. J. (Pharm., 219, 193 (1992)). Stimulation of $\beta_3$ receptors has also been demonstrated to induce relaxation of smooth muscle in the colon, trachea, and bronchi. See, for example, Life Sciences, 44, 1411 (1989), Br. J. Pharm., 112, 55 (1994), and Br. J. Pharmacol., 110, 1311 (1993). Furthermore, stimulation of $\beta_3$ receptors has also been found to induce relaxation of histamine-contracted guinea pig ileum. See, for example, J. Pharm. Exp. Ther., 260, 1, 192 (1992).

The $\beta_3$ receptor is also expressed in the human prostate (J. Clin. Invest., 91, 344 (1993). Because stimulation of the $\beta_3$ receptor causes relaxation of smooth muscles that have been shown to express the $\beta_3$ receptor, i.e. intestinal smooth muscle, one of ordinary skill in the art would also predict relaxation of prostate smooth muscle. Therefore, $\beta_3$ agonists are useful in the treatment or prevention of prostate disease.

Commonly assigned U.S. Pat. No. 5,977,124 discloses certain $\beta_3$ adrenergic receptor agonists having utility in the treatment of, inter alia, hypoglycemia and obesity.

U.S. Pat. No. 5,776,983 discloses certain catecholamines useful as $\beta_3$-agonists.

U.S. Pat. No. 5,030,640 discloses certain α-heterocyclic ethanol amino alkyl indoles, which are useful as growth promoters, bronchodilators, anti-depressants, and anti-obesity agents.

U.S. Pat. No. 5,019,578 discloses certain α-heterocyclic ethanolamines useful as growth promoters.

U.S. Pat. No. 4,478,849 discloses pharmaceutical compositions comprising certain ethanolamine derivatives and methods of using such compositions in the treatment of obesity and/or hyperglycaemia.

U.S. Pat. No. 4,358,455 discloses certain heterocyclic compounds of the structural formula Het—CHOH—CH₂—

NH—aralkyl, which compounds are useful for treating glaucoma and cardiovascular disease.

European Patent Application Publication No. 0 516 349, published Dec. 2, 1992, discloses certain 2-hydroxyphenethyl amines which possess anti-obesity, hypoglycemic, and related utilities.

U.S. Pat. No. 5,153,210 discloses certain heterocyclic compounds of the formula $R^o$—X—CH(OH)—CH$_2$—N($R^1$)—C($R^2$)($R^3$)—(CH$_2$)$_n$—Y—A—$R^4$—$R^5$ which compounds are useful as anti-obesity and anti-hyperglycaemic agents.

PCT International Patent Application Publication No. WO 99/65877, published Dec. 23, 1999, discloses heterocyclic compounds having the structural formula

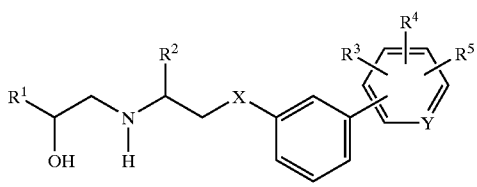

which compounds are useful for the treatment of diseases susceptible to amelioration by administration of an atypical beta-adrenoceptor agonist.

SUMMARY OF THE INVENTION

The instant invention provides $\beta_3$ adrenergic receptor agonists of structural Formula (I),

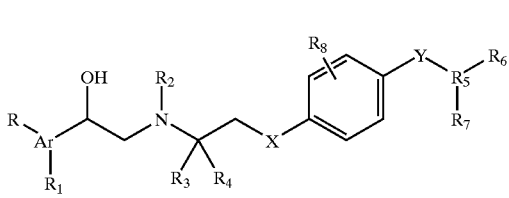

the stereoisomers and prodrugs thereof, and the pharmaceutically acceptable salts of the compounds, stereoisomers and prodrugs, wherein Ar, R, $R_1$, $R_2$, $R_3$, $R_4$, $R_5$, $R_6$, $R_7$, $R_8$, X, and Y are as defined hereinbelow.

In another aspect, the invention provides intermediates useful in the preparation of the compounds of Formula (I); to combinations of the compounds of Formula (I), the stereoisomers and prodrugs thereof, and the pharmaceutically acceptable salts of the compounds, stereoisomers and prodrugs, with anti-obesity agents; to pharmaceutical compositions comprising the compounds of Formula (I), the stereoisomers and prodrugs thereof, and the pharmaceutically acceptable salts of the compounds, stereoisomers and prodrugs, or pharmaceutical compositions comprising the compounds of Formula (I), the stereoisomers and prodrugs thereof, and the pharmaceutically acceptable salts of the compounds, stereoisomers and prodrugs, and anti-obesity agents; and methods of treating $\beta_3$ adrenergic receptor-mediated diseases, conditions, or disorders in a mammal which methods comprise administering to the mammal an effective amount of a compound of Formula (I), a stereoisomer or prodrug thereof, or a pharmaceutical composition thereof; or a combination of a compound of Formula (I), a pharmaceutically acceptable salt of the compound, stereoisomer, or prodrug, and an anti-obesity agent, or a pharmaceutical composition thereof, acceptable salt of the compound, stereoisomer, or prodrug, and an anti-obesity agent, or a pharmaceutical composition thereof.

DETAILED DESCRIPTION OF THE INVENTION

The present invention provides $\beta_3$ adrenergic receptor agonists of structural Formula (I),

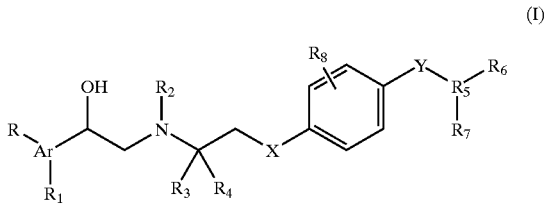

the stereoisomers and prodrugs thereof, and the pharmaceutically acceptable salts of said compounds, stereoisomers and prodrugs, wherein:

Ar is pyridyl, oxazolyl, thiazolyl, or phenyl;

R is hydrogen, hydroxy, oxo, halogen, —CF$_3$, —(C$_1$–C$_6$)alkyl, —(C$_1$–C$_6$)alkoxy, —(C$_3$–C$_8$)cycloalkyl, —NR$_9$R$_{10}$, —NR$_9$SO$_2$R$_{10}$, —NR$_9$COR$_{10}$, or —SO$_2$R$_9$;

R$_1$ is hydrogen, —(C$_1$–C$_6$)alkyl, halogen, —(C$_1$–C$_6$)alkoxy, or hydroxy;

R$_2$, R$_3$, R$_4$ are, independently, hydrogen, or —(C$_1$–C$_6$)alkyl;

R$_5$ is a 5- or 6-membered ring heterocycle having from 1 to 4 heteroatoms selected from the group consisting of oxygen, sulfur, or nitrogen;

R$_6$ and R$_7$ are, independently, hydrogen, halogen, cyano, oxo, —(C$_1$–C$_6$)acyl, —CO$_2$R$_9$, —NR$_9$R$_{10}$, hydroxy, —(C$_1$–C$_6$)alkoxy, —CONR$_9$R$_{10}$, —NR$_9$SO$_2$R$_{10}$, —SO$_2$NR$_9$R$_{10}$, or —SO$_2$R$_9$; —(C$_1$–C$_6$)alkyl, optionally substituted with —(C$_3$–C$_8$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; —(C$_3$–C$_8$)cycloalkyl, optionally substituted with —(C$_1$–C$_6$)alkyl, —(C$_3$–C$_8$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; aryl, optionally substituted with —(C$_1$–C$_6$)alkyl, —(C$_3$–C$_7$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; or heterocycle, optionally substituted with —(C$_1$–C$_6$)alkyl, —(C$_3$–C$_8$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle;

R$_8$ is hydrogen, —(C$_1$–C$_4$)alkyl, or halogen; and

R$_9$ and R$_{10}$ are, independently, hydrogen, —(C$_1$–C$_6$)alkyl, alkylalkoxy, —(C$_3$–C$_8$)cycloalkyl, —(C$_1$–C$_6$)haloalkyl, —(C$_1$–C$_6$)alkoxy, aryl, or heterocycle;

X is a direct bond or oxygen; and

Y is a direct bond, —(C$_1$–C$_6$)alkyl, —OCH$_2$—, —CH$_2$O—, or oxygen; provided that:

(i) when Ar is phenyl, R is —NR$_9$SO$_2$R$_{10}$, —SO$_2$NR$_9$R$_{10}$, or —SO$_2$R$_9$; and (ii) when Ar is phenyl, —NR$_9$SO$_2$R$_{10}$, and R$_6$ and R$_7$ are both hydrogen, then R$_5$ is not imidazolyl.

The compounds of Formula (I), the stereoisomers and prodrugs thereof, and the pharmaceutically acceptable salts of the compounds, stereoisomers and prodrugs, wherein Ar, R, R$_1$, R$_2$, R$_3$, R$_4$, R$_5$, R$_6$, R$_7$, R$_8$, X, and Y are as defined hereinabove, that are extant in the (R)-stereo configuration, designated by Formula (I') hereinbelow, are especially preferred.

$$(I')$$

A first generally preferred subgroup of the compounds of Formula (I), the stereoisomers and prodrugs thereof, and the pharmaceutically acceptable salts of the compounds, stereoisomers and prodrugs, comprises those compounds wherein Ar is pyridyl; R, $R_1$, $R_2$, $R_3$, $R_4$ and $R_8$, are hydrogen; X is oxygen; Y is a direct bond; and $R_5$ is a five- or six-membered ring heterocycle selected from the group consisting of dihydropyridazinonyl, imidazolyl, isothiazolyl, isoxazolyl, oxadiazolyl, oxazolinyl, oxazolyl, pyrazinyl, pyrazolyl, pyridazinonyl, pyridazinyl, pyridyl, pyrimidinonyl, pyrimidyl, thiadiazolyl, thiazolinyl, thiazolyl, triazinyl, and triazolyl, Among the first generally preferred subgroup of the compounds of Formula (I), the stereoisomers and prodrugs thereof, and the pharmaceutically acceptable salts of the compounds, stereoisomers and prodrugs, the following compounds are particularly preferred:

(R)-2-{2-[4-(4-benzofuran-2-yl-thiazol-2-yl)-phenoxy]-ethylamino}-1-pyridin-3-yl-ethanol;
(R)-2-{2-[4-(2-benzyloxymethyl-oxazol-4-yl)-phenoxy]-ethylamino}-1-pyridin-3-yl-ethanol;
(R)-2-{2-[4-(2-butyl-thiazol-4-yl)-phenoxy]-ethylamino}-1-pyridin-3-yl-ethanol;
(R)-2-{2-[4-(2-tert-butyl-thiazol-4-yl)-phenoxy]-ethylamino}-1-pyridin-3-yl-ethanol;
(R)-2-{2-[4-(2-cyclopentyl-thiazol-4-yl)-phenoxy]-ethylamino}-1-pyridin-3-yl-ethanol;
(R)-2-{2-[4-(2,5-dimethyl-oxazol-4-yl)-phenoxy]-ethylamino}-1-pyridin-3-yl-ethanol;
(R)-2-(2-{4-[2-(2-ethyl-pyridin-4-yl)-thiazol-4-yl]-phenoxy}-ethylamino)-1-pyridin-3-yl-ethanol;
(R)-2-{2-[4-(2-ethyl-oxazol-4-yl)-phenoxy]-ethylamino}-1-pyridin-3-yl-ethanol;
(R)-2-{2-[4-(4-ethyl-thiazol-2-yl)-phenoxy]-ethylamino}-1-pyridin-3-yl-ethanol;
(R)-2-{2-[4-(2-ethyl-thiazol-4-yl)-phenoxy]-ethylamino}-1-pyridin-3-yl-ethanol;
(R)-2-{2-[4-(2-hydroxymethyl-oxazol-4-yl)-phenoxy]-ethylamino}-1-pyridin-3-yl-ethanol;
(R)-6-{4-[2-(2-hydroxy-2-pyridin-3-yl-ethylamino)-ethoxy]-phenyl}-4,5-dihydro-2H-pyridazin-3-one;
(R)-2-[2-(4-imidazol-1-yl-phenoxy)-ethylamino]-1-pyridin-3-yl-ethanol;
(R)-2-{2-[4-(2-isopropyl-1H-imidazol-4-yl)-phenoxy]-ethylamino}-1-pyridin-3-yl-ethanol;
(R)-2-{2-[4-(2-isopropyl-oxazol-4-yl)-phenoxy]-ethylamino}-1-pyridin-3-yl-ethanol;
(R)-2-{2-[4-(2-isopropyl-thiazol-4-yl)-phenoxy]-ethylamino}-1-pyridin-3-yl-ethanol;
(R)-2-{2-[4-(2-methoxymethyl-oxazol-4-yl)-phenoxy]-ethylamino}-1-pyridin-3-yl-ethanol;
(R)-2-(2-{4-[2-(4-methoxy-phenyl)-thiazol-4-yl]-phenoxy}-ethylamino)-1-pyridin-3-yl-ethanol;
(R)-2-{2-[4-(2-methyl-1H-imidazol-4-yl)-phenoxy]-ethylamino}-1-pyridin-3-yl-ethanol;
(R)-2-{2-[4-(5-methyl-[1,3,4]oxadiazol-2-yl)-phenoxy]-ethylamino}-1-pyridin-3-yl-ethanol;
(R)-2-{2-[4-(2-methyl-oxazol-4-yl)-phenoxy]-ethylamino}-1-pyridin-3-yl-ethanol;
(R)-2-{2-[4-(5-methyl-oxazol4-yl)-phenoxy]-ethylamino}-1-pyridin-3-yl-ethanol;
(R)-2-(2-{4-[2-(2-methyl-propane-2-sulfonylmethyl)-thiazol-4-yl]-phenoxy}-ethylamino)-1-pyridin-3-yl-ethanol;
(R)-2-{2-[4-(1-methyl-1H-pyrazol-3-yl)-phenoxy]-ethylamino}-1-pyridin-3-yl-ethanol;
(R)-2-{2-[4-(4-methyl-thiazol-2-yl)-phenoxy]-ethylamino}-1-pyridin-3-yl-ethanol;
(R)-2-{2-[4-(2-methyl-thiazol-4-yl)-phenoxy]-ethylamino}-1-pyridin-3-yl-ethanol;
(R)-2-{2-[4-(5-methyl-4H-[1,2,4]triazol-3-yl)-phenoxy]-ethylamino}-1-pyridin-3-yl-ethanol;
(R)-2-{2-[4-(2'-methyl-[2,4']bithiazolyl-4-yl)-phenoxy]-ethylamino}-1-pyridin-3-yl-ethanol;
(R)-2-[2-(4-oxazol-4-yl-phenoxy)-ethylamino]-1-pyridin-3-yl-ethanol;
(R)-2-[2-(4-oxazol-5-yl-phenoxy)-ethylamino]-1-pyridin-3-yl-ethanol;
(R)-2-{2-[4-(2-phenyl-1H-imidazol-4-yl)-phenoxy]-ethylamino}-1-pyridin-3-yl-ethanol;
(R)-2-{2-[4-(2-phenyl-thiazol-4-yl)-phenoxy]-ethylamino}-1-pyridin-3-yl-ethanol;
(R)-2-{2-[4-(4-phenyl-thiazol-2-yl)-phenoxy]-ethylamino}-1-pyridin-3-yl-ethanol;
(R)-2-{2-[4-(2-propyl-thiazol-4-yl)-phenoxy]-ethylamino}-1-pyridin-3-yl-ethanol;
(R)-2-{2-[4-(1H-pyrazol-3-yl)-phenoxy]-ethylamino}-1-pyridin-3-yl-ethanol;
(R)-1-pyridin-3-yl-2-{2-[4-(2-pyridin-3-yl-1H-imidazol-4-yl)-phenoxy]-ethylamino}-ethanol;
(R)-1-pyridin-3-yl-2-{2-[4-(2-pyridin-4-yl-1H-imidazol-4-yl)-phenoxy]-ethylamino}-ethanol;
(R)-1-pyridin-3-yl-2-{2-[4-(2-pyridin-3-yl-thiazol-4-yl)-phenoxyl-ethylamino}-ethanol;
(R)-1-pyridin-3-yl-2-{2-[4-(2-pyridin-4-yl-thiazol-4-yl)-phenoxyl]-ethylamino}-ethanol;
(R)-1-pyridin-3-yl-2-[2-(4-thiazol-2-yl-phenoxy)-ethylamino]-ethanol
(R)-1-pyridin-3-yl-2-[2-(4-thiazol-4-yl-phenoxy)-ethylamino]-ethanol;
(R)-1-pyridin-3-yl-2-{2-[4-(2-thiophen-2-yl-1H-imidazol-4-yl)-phenoxy]-ethylamino}-ethanol;
(R)-1-pyridin-3-yl-2-{2-[4-(2-thiophen-2-yl-thiazol-4-yl)-phenoxy]-ethylamino}-ethanol;
(R)-1-pyridin-3-yl-2-{2-[4-(4-p-tolyl-thiazol-2-yl)-phenoxy]-ethylamino}-ethanol;
(R)-1-pyridin-3-yl-2-{2-[4-(2-p-tolyl-thiazol-4-yl)-phenoxy]-ethylamino}-ethanol;
(R)-1-pyridin-3-yl-2-{2-[4-(2-trifluoromethyl-1H-imidazol-4-yl)-phenoxy]-ethylamino}-ethanol;
(R)-1-pyridin-3-yl-2-(2-{4-[2-(4-trifluoromethyl-phenyl)-thiazol-4-yl]-phenoxy}-ethylamino)-ethanol;
(R)-1-pyridin-3-yl-2-{2-[4-(4-trifluoromethyl-thiazol-2-yl)-phenoxy]-ethylamino}-ethanol; and
(R)-1-pyridin-3-yl-2-{2-[4-(2-trifluoromethyl-thiazol-4-yl)-phenoxy]-ethylamino}-ethanol.

Among the first generally preferred subgroup of the compounds of Formula (I), the stereoisomers and prodrugs thereof, and the pharmaceutically acceptable salts of the compounds, stereoisomers and prodrugs, the following compounds are especially preferred:

(R)-2-{2-[4-(ethyl-thiazol-2-yl)-phenoxy]-ethylamino}-1-pyridin-3-yl-ethanol;
(R)-2-{2-[4-(2-methoxymethyl-oxazol-4-yl)-phenoxy]-ethylamino}-1-pyridin-3-yl-ethanol;

(R)-2-{2-[4-(2-methyl-oxazol-4-yl)-phenoxy]-ethylamino}-1-pyridin-3-yl-ethanol;
(R)-2-{2-[4-(2-methyl-thiazol-4-yl)-phenoxy]-ethylamino}-1-pyridin-3-yl-ethanol;
(R)-2-[2-(4-oxazol-4-yl-phenoxy)-ethylamino]-1-pyridin-3-yl-ethanol;
(R)-2-{2-[4-(1H-pyrazol-3-yl)-phenoxy]-ethylamino}-1-pyridin-3-yl-ethanol;
(R)-1-pyridin-3-yl-2-[2-(4-thiazol-2-yl-phenoxy)-ethylamino]-ethanol;
(R)-1-pyridin-3-yl-2-[2-(4-thiazol-4-yl-phenoxy)-ethylamino]-ethanol; and
(R)-1-pyridin-3-yl-2-{2-[4-(4-trifluoromethyl-thiazol-2-yl)-phenoxy]-ethylamino}-ethanol.

A second generally preferred subgroup of the compounds of Formula (I), the stereoisomers and prodrugs thereof, and the pharmaceutically acceptable salts of said compounds, stereoisomers and prodrugs, comprises those compounds wherein Ar is phenyl; R is —NR$_9$SO$_2$R$_{10}$; R$_1$ is hydrogen, hydroxy, or halogen; R$_2$, R$_3$, R$_4$, and R$_8$, are hydrogen; X is oxygen and Y is a direct bond; and R$_5$ is a five- or six-membered ring heterocycle selected from the group consisting of dihydropyridazinonyl, imidazolyl, isothiazolyl, isoxazolyl, oxadiazolyl, oxazolinyl, oxazolyl, pyrazinyl, pyrazolyl, pyridazinonyl, pyridazinyl, pyridyl, pyrimidinonyl, pyrimidyl, thiadiazolyl, thiazolinyl, thiazolyl, triazinyl, and triazolyl.

Among the second generally preferred subgroup of the compounds of Formula (I), the stereoisomers and prodrugs thereof, and the pharmaceutically acceptable salts of the compounds, stereoisomers and prodrugs, the following compounds are particularly preferred:
(R)-N-[2-chloro-5-(2-{2-[4-(2-ethyl-oxazol-4-yl)-phenoxy]-ethylamino}-1-hydroxy-ethyl)-phenyl]-methanesulfonamide;
(R)-N-[2-chloro-5-(2-{2-[4-(2-ethyl-thiazol-4-yl)-phenoxy]-ethylamino}-1-hydroxy-ethyl)-phenyl]-methanesulfonamide;
(R)-N-[2-chloro-5-(1-hydroxy-2-{2-[4-(2-isopropyl-1H-imidazol-4-yl)-phenoxy]-ethylamino}-ethyl)-phenyl]-methanesulfonamide;
(R)-N-[2-chloro-5-(1-hydroxy-2-{2-[4-(2-isopropyl-oxazol-4-yl)-phenoxy]-ethylamino}-ethyl)-phenyl]-methanesulfonamide;
(R)-N-[2-chloro-5-(1-hydroxy-2-{2-[4-(2-methyl-oxazol-4-yl)-phenoxy]-ethylamino}-ethyl)-phenyl]-methanesulfonamide;
(R)-N-[2-chloro-5-(1-hydroxy-2-{2-[4-(2-methyl-1H-imidazol-4-yl)-phenoxy]-ethylamino}-ethyl)-phenyl]-methanesulfonamide;
(R)-N-[2-chloro-5-(1-hydroxy-2-{2-[4-(2-methyl-thiazol-4-yl)-phenoxy]-ethylamino}-ethyl)-phenyl]-methanesulfonamide;
(R)-N-(2-chloro-5-{1-hydroxy-2-[2-(4-oxazol-4-yl-phenoxy)-ethylamino]-ethyl}-phenyl)-methanesulfonamide;
(R)-N-[2-chloro-5-(1-hydroxy-2-{2-[4-(2-phenyl-1H-imidazol-4-yl)-phenoxy]-ethylamino}-ethyl)-phenyl]-methanesulfonamide;
(R)-N-[2-chloro-5-(1-hydroxy-2-{2-[4-(2-pyridin-3-yl-1H-imidazol-4-yl)-phenoxy]-ethylamino}-ethyl)-phenyl]-methanesulfonamide;
(R)-N-[2-chloro-5-(1-hydroxy-2-{2-[4-(2-pyridin-4-yl-1H-imidazol-4-yl)-phenoxy]-ethylamino}-ethyl)-phenyl]-methanesulfonamide;
(R)-N-(2-chloro-5-{1-hydroxy-2-[2-(4-thiazol-4-yl-phenoxy)-ethylamino]-ethyl}-phenyl)-methanesulfonamide; and
(R)-N-[2-chloro-5-(1-hydroxy-2-{2-[4-(2-trifluoromethyl-1H-imidazol-4-yl)-phenoxy]-ethylamino}-ethyl)-phenyl]-methanesulfonamide.

Among the second generally preferred subgroup of the compounds of Formula (I), the stereoisomers and prodrugs thereof, and the pharmaceutically acceptable salts of the compounds, stereoisomers and prodrugs, the following compounds are especially preferred:
(R)-N-[2-chloro-5-(2-{4-(2-ethyl-oxazol-4-yl)-phenoxy]-ethylamino}-1-hydroxy-ethyl)-phenyl]-methanesulfonamide;
(R)-N-[2-chloro-5-(2-{4-(2-ethyl-thiazol-4-yl)-phenoxy]-ethylamino}-1-hydroxy-ethyl)-phenyl]-methanesulfonamide;
(R)-N-[2-chloro-5-(1-hydroxy-2-{2-[4-(2-methyl-thiazol-4-yl)-phenoxy]-ethylamino}-ethyl)-phenyl]-methanesulfonamide;
(R)-N-(2-chloro-5-{1-hydroxy-2-[2-(4-thiazol-4-yl-phenoxy)-ethylamino]-ethyl}-phenyl)-methanesulfonamide;
(R)-N-[2-chloro-5-(1-hydroxy-2-{2-[4-(2-methyl-oxazol-4-yl)-phenoxy]-ethylamino}-ethyl)-phenyl]-methanesulfonamide; and
(R)-N-(2-chloro-5-{1-hydroxy-2-[2-(4-oxazol-4-yl-phenoxy)-ethylamino]-ethyl}-phenyl)-sulfonamide.

The instant invention further provides certain amine intermediates useful in the preparation of the compounds of Formula (I) which amine intermediates comprise compounds having the structural formula

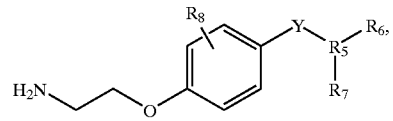

and the acid addition salts thereof, wherein:
R$_5$ is a 5- or 6-membered ring heterocycle selected from the group consisting of isothiazolyl, isoxazolyl, oxadiazolyl, oxazolinyl, oxazolyl, pyrazolyl, pyridazinyl, thiadiazolyl, thiazolyl, triazinyl;
R$_6$ and R$_7$ are, independently, hydrogen, halogen, cyano, oxo, —(C$_1$–C$_6$)acyl, —CO$_2$R$_9$, —NR$_9$R$_{10}$, hydroxy, —(C$_1$–C$_6$)alkoxy, —CONR$_9$R$_{10}$, —NR$_9$SO$_2$R$_{10}$, —SO$_2$NR$_9$R$_{10}$, or —SO$_2$R$_9$; —(C$_1$–C$_6$)alkyl, optionally substituted with —(C$_3$–C$_8$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; —(C$_3$–C$_8$)cycloalkyl, optionally substituted with —(C$_1$–C$_6$)alkyl, —(C$_3$–C$_8$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; aryl, optionally substituted with —(C$_1$–C$_6$)alkyl, —(C$_3$–C$_7$)cycloalkyl, halogen, aryl, —(C$_1$–C$_6$)alkoxy, —(C$_1$–C$_6$)haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle; or heterocycle, optionally substituted with —(C$_1$–C$_6$)alkyl, —(C$_3$–C$_8$) cycloalkyl, halogen, aryl, —(C$_1$–C$_6$)alkoxy, —(C$_1$–C$_6$) haloalkyl, alkylalkoxy, hydroxy, —NR$_9$R$_{10}$, —NR$_9$SO$_2$R$_{10}$, —SO$_2$NR$_9$R$_{10}$, —SO$_2$R$_9$, or heterocycle;
R$_8$ is hydrogen, —(C$_1$–C$_4$)alkyl, or halogen; and
Y is a direct bond, or —CH$_2$—.

Generally preferred amine intermediates of the structural formula shown hereinabove comprise those compounds selected from the group consisting of:
2-[4-(4-benzofuran-2-yl-thiazol-2-yl)-phenoxy]-ethylamine;

2-[4-(2-benzyloxymethyl-oxazol-4-yl)-phenoxy]-ethylamine;
2-[4-(2-tert-butyl-thiazol-4-yl)-phenoxy]-ethylamine;
2-[4-(2-butyl-thiazol-4-yl)-phenoxy]-ethylamine;
2-[4-(2-cyclopentyl-thiazol-4-yl)-phenoxy]-ethylamine;
2-[4-(2,5-dimethyl-oxazol-4-yl)-phenoxy]-ethylamine;
2-[4-(2-ethyl-oxazol-4-yl-4)-phenoxy]-ethylamine;
2-{4-[2-(2-ethyl-pyridin-4-yl)-thiazol-4-yl]-phenoxy}-ethylamine;
2-[4-(4-ethyl-thiazol-2-yl)-phenoxy]-ethylamine;
2-[4-(4-ethyl-thiazol-4-yl)-phenoxy]-ethylamine;
2-[4-(2-hydroxymethyl-oxazol-4-yl)-phenoxy]-ethylamine;
2-[4-(2-isopropyl-oxazol-4-yl)-phenoxy}-ethylamine;
2-[4-(2-isopropyl-thiazol-4-yl)-phenoxy]-ethylamine;
2-[4-(2-methoxymethyl-oxazol-4-yl)-phenoxy]-ethylamine;
2-{4-[2-(4-methoxy-phenyl)-thiazol-4-yl]-phenoxy}-ethylamine;
2-[4-(2-methyl-oxazol-4-yl)-phenoxy]-ethylamine;
2-[4-(5-methyl-oxazol-4-yl)-phenoxy]-ethylamine;
2-(3-methyl-4-oxazol-4-yl)-phenoxy]-ethylamine;
2-{4-[2-(2-methyl-propane-2-sulfonylmethyl)-thiazol-4-yl]-phenoxy}-ethylamine;
2-[4-(1-methyl-1H-pyrazol-3-yl)-phenoxy]-ethylamine;
2-[4-(2-methyl-thiazol-4-yl)-phenoxyl-ethylamine;
2-[4-(4-methyl-thiazol-2-yl)-phenoxyl-ethylamine;
2-[4-(2'-methyl-[2,4']bithiazolyl-4-yl)-phenoxy]-ethylamine;
2-[4-(5-methyl-[1,3,4]oxadiazol-2-yl)-phenoxy]-ethylamine;
2-(4-[1,3,5]oxadiazol-2-yl-phenoxy)-ethylamine;
2-(4-oxazol-2-yl-phenoxy)-ethylamine;
2-(4-oxazol-4-yl-phenoxy)-ethylamine;
2-(4-oxazol-5-yl-phenoxy)-ethylamine;
2-[4-(2-phenethyl-thiazol-4-yl)-phenoxy]-ethylamine;
2-[4-(5-phenyl-[1,3,4]oxadiazol-2-ylmethyl)-phenoxy]-ethylamine;
2-[4-(4-phenyl-thiazol-2-yl)-phenoxy]-ethylamine;
2-[4-(2-phenyl-thiazol-4-yl)-phenyl]-ethylamine;
2-[4-(2-propyl-thiazol-4-yl)-phenoxy]-ethylamine;
2-(4-pyrazol-1-yl-phenoxy)-ethylamine;
2-[4-(1H-pyrazol-3-yl)-phenoxy]-ethylamine;
2-[4-(2-pyridin-3-yl-thiazol-4-yl)-phenoxy]-ethylamine;
2-4-(2-pyridin-4-yl-thiazol-4-yl)-phenoxy]-ethylamine;
2-(4-[1,2,3]thiadiazol-5-yl-phenoxy)-ethylamine;
2-(4-thiazol-2-yl-phenoxy)-ethylamine;
2-(4-thiazol-4-yl-phenoxy)-ethylamine;
2-[4-(2-thiophen-2-ylthiazol-4-yl)-phenoxy]-ethylamine;
2-[4-(2-p-tolyl-thiazol-4-yl)-phenoxy]-ethylamine;
2-[4-(4-p-tolyl-thiazol-2-yl)-phenoxy]-ethylamine;
2-[4-(2-trifluoromethyl-thiazol-4-yl)-phenoxy]-ethylamine;
2-{4-[-(4-trifluoromethyl-phenyl)-thiazol-4-yl]-phenoxy-ethylamine;
2-[4-(4-trifluoromethyl-thiazol-2-yl)-phenoxy]-ethylamine; and
2-[4-(5-trifluoromethyl-2H-pyrazol-3-yl)-phenoxy]-ethylamine; and the acid addition salts thereof.

The compounds and intermediates of the present invention may be named according to either the IUPAC (International Union for Pure and Applied Chemistry) or CAS (Chemical Abstracts) nomenclature systems.

The carbon atom content of the various hydrocarbon-containing moieties may be indicated by a prefix designating the minimum and maximum number of carbon atoms in the moiety, i.e. the prefix ($C_a$–$C_b$) indicates a moiety of the integer "a" to "b" carbon atoms, inclusive. Thus, for example, ($C_1$–$C_3$)alkyl refers to alkyl of one to three carbon atoms inclusive, or methyl, ethyl, propyl, isopropyl, and all isomeric forms, and straight and branched chain forms thereof.

The term "alkyl" denotes a straight or branched chain hydrocarbon. Representative examples of alkyl groups comprise methyl, ethyl, propyl, isopropyl, butyl, isobutyl, tert-butyl, sec-butyl, pentyl, and hexyl.

The term "alkoxy" denotes an alkyl group bonded to an oxygen atom. Representative examples of alkoxy groups include methoxy, ethoxy, tert-butoxy, propoxy, and isobutoxy.

The term "halogen" or "halo" denotes a radical derived from chlorine, fluorine, bromine, or iodine.

The term "cycloalkyl" denotes a cyclic hydrocarbon. Examples of cycloalkyl groups include cyclopropyl, cyclobutyl, cyclopentyl, cyclohexyl, and cycloheptyl. It is also possible for the cycloalkyl group to have one or more double or triple bonds, or a combination of double bonds and triple bonds, but is not aromatic. Examples of cycloalkyl groups having a double or triple bond include cyclopentenyl, cyclohexenyl, cyclohexadienyl, cyclobutadienyl, and the like. It is also noted that the term cycloalkyl includes polycyclic compounds such as bicyclic or tricyclic compounds.

The term "acyl" denotes a group derived from an organic acid (—COOH) by removal of of the hydroxy group (—OH).

The term "aryl" denotes a cyclic, aromatic hydrocarbon. Examples of aryl groups include phenyl, naphthyl, and biphenyl. The aryl group can be substituted or unsubstituted.

The term "heteroatom" includes oxygen, nitrogen, sulfur, and phosphorus.

The term "heterocycle", as employed within the definitions of $R_5$, $R_6$, $R_7$, $R_9$, and $R_{10}$, denotes a cyclic, aromatic or non-aromatic hydrocarbon radical in which between one and four of the carbon atoms therein have been replaced with heteroatoms. If the heterocyclic radical contains more than one heteroatom, the individual heteroatoms may be the same or different. Representative examples of five- and six-membered aromatic, or non-aromatic, heterocyclic groups include chromenyl, dihydropyridazinonyl, dihydropyridazinyl, furyl, imidazolidinyl, imidazolyl, indazolyi, indolizinyl, indolyl, isobenzofuranyl, isoindolyl, isoquinolyl, isothiazolyl, isoxazolyl, morpholinyl, naphthyridinyl, oxadiazolyl, oxazinyl, oxazolinyl, oxazolyl, phthalazinyl, piperazinyl, piperidinyl, purinyl, pyranyl, pyrazolyl, pyridazinonyl, pyridazinyl, pyridyl, pyrimidinonyl, pyrimidyl, pyrrolidinyl, pyrrolyl, quinolizinyl, quinolyl, quinoxalinyl, thiadiazolyl, thiazolinyl, thiazolyl, thienyl, thiomorpholinyl, triazolyl, and xanthenyl. It is to be understood that the heterocyclic radical may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

Specific representative examples of five- to six-membered aromatic, or non-aromatic, heterocyclic groups are 1,4-dioxanyl, 3H-1,2,3-dioxazolyl, 1,2,4-dioxazolyl, 1,3,2-dioxazolyl, 1,3,4-dioxazolyl, 1,2-dioxinyl, 1,3-dioxinyl, 1,3-dioxolanyl, 1,4-dithianyl, 1,2-dithiolyl, 1,3-dithiolyl, 2-imidazolinyl, 2H-imidazolyl, o-isoxazinyl, p-isoxazinyl, 1,2,3-oxadiazolyl, 1,2,4-oxadiazolyl, 1,2,5-oxadiazolyl, 1,3,4-oxadiazolyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, 1,2,5-oxathiazinyl, 1,2,6-oxathiazinyl, 1,4,2-oxadiazinyl, 5H-1,2,5-oxathiazolyl, 3H-1,2-oxathiolyl, 1,3-oxathiolyl, 2H-pyranyl, 4H-pyranyl, 2-pyrazolinyl, 2-pyrrolinyl, 3-pyrrolinyl, 1,3,4-thiadiazolyl, 1,2,3-triazinyl, 1,2,4-triazinyl, 1,3,5-triazinyl, 1,2,3-triazolyl, 1,2,4-triazolyl, and 1,3,5-trithianyl.

It is also noted that the heterocyclic radical can comprise more than one ring. For example, a naphthyl group is a representative of a fused bicyclic ring system. It is also intended that the present invention include ring groups that have bridging atoms, or ring groups having a spiro-orientation. For example, the term "spirocycloalkyl" means a cycloalkyl ring having a spiro union (the union formed by a single atom which is the only common member of the rings). In addition, it is understood that, unless specifically noted otherwise, all suitable isomers of the cyclic ring groups are included herein.

Exemplary bicyclic rings consisting of two fused partially saturated, fully saturated, or fully unsaturated five- and/or six-membered rings, taken independently, optionally having one to four heteroatoms are anthranilyl, benzimidazolyl, benzofuryl, 2H-1-benzopyranyl, benzothiazolyl, benzo[b]thienyl, benzo[c]thienyl, 2H-1,3-benzoxazinyl, 2H-1,4-benzoxazinyl, 1H-2,3-benzoxazinyl, 4H-3,1-benzoxazinyl, 2H-1,2-benzoxazinyl, 4H-1,4-benzoxazinyl, benzoxazolyl, cinnolinyl, cyclopenta[b]pyridinyl, decalinyl, indazolyl, indenyl, indolinyl, indolizinyl, indolyl, 1H-indoxazinyl, isobenzofuryl, isoindenyl, isoindolyl, isoquinolinyl, naphthyl, naphthyridinyl, phthalazinyl, 1,8-pteridinyl, purinyl, pyrano[3,4-b]pyrrolyl, pyrido[3,2-b]-pyridinyl, pyrido[3,4-b]-pyridinyl, pyrido[4,3-b]-pyridinyl, quinazolinyl, quinolinyl, quinoxalinyl, and tetralinyl.

The term "substituted" means that a hydrogen atom on a molecule has been replaced with a different atom or molecule. The atom or molecule replacing the hydrogen atom is denoted as a "substituent."

The phrase "therapeutically effective amount" means an amount of a compound of Formula (I), a stereoisomer or prodrug thereof, or a pharmaceutically acceptable salt of the compound, stereoisomer, or prodrug, which amount attenuates, ameliorates, or eliminates one or more symptoms of a particular disease, condition, or disorder, or prevents or delays the onset of one or more symptoms of a particular disease, condition, or disorder.

The term "mammal" means animals including, for example, dogs, cats, cows, sheep, horses, and humans. Preferred mammals include humans, including members of both male and female sexes.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

In another aspect of the instant invention, the compounds of Formula (I), the stereoisomers and prodrugs thereof, and the pharmaceutically acceptable salts of the compounds, stereoisomers and prodrugs, can be employed in combination with an anti-obesity agent.

The anti-obesity agent is preferably selected from the group consisting of an apolipoprotein-B secretion/microsomal triglyceride transfer protein (apo-B/MTP) inhibitor, an MCR-4 agonist, a cholecystokinin-A (CCK-A) agonist, a monoamine reuptake inhibitor (such as sibutramine), a sympathomimetic agent, a serotoninergic agent (such as fenfluramine or dexfenfluramine), a dopamine agonist (such as bromocriptine), a melanocyte-stimulating hormone receptor analog, a cannabinoid receptor antagonist, a melanin concentrating hormone antagonist, leptin (the OB protein), a leptin analog, a leptin receptor agonist, a galanin antagonist, a lipase inhibitor (such as tetrahydrolipstatin, i.e. orlistat), an anorectic agent (such as a bombesin agonist), a Neuropeptide-Y antagonist, a thyromimetic agent, dehydroepiandrosterone or an analog thereof, a glucocorticoid receptor agonist or antagonist, an orexin receptor antagonist, a urocortin binding protein antagonist, a glucagon-like peptide-1 receptor agonist, a ciliary neurotrophic factor (such as Axokine), and human agouti-related protein (AGRP). Other anti-obesity agents, including the preferred agents set forth hereinbelow, are well known, or will be readily apparent in light of the instant disclosure, to one of ordinary skill in the art.

Especially preferred anti-obesity agents comprise those compounds selected from the group consisting of orlistat, sibutramine, fenfluramine, dexfenfluramine, bromocriptine, phentermine, ephedrine, leptin, phenylpropanolamine, and pseudoephedrine.

Representative anti-obesity agents for use in the combinations, pharmaceutical compositions, and methods of the invention can be prepared using methods known to one of ordinary skill in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888; and orlistat can be prepared as described in U.S. Pat. Nos. 5,274,143, 5,420,305, 5,540,917, and 5,643,874.

The present invention further provides methods of treating $\beta_3$ adrenergic receptor-mediated diseases, conditions, or disorders in a mammal in need of such treatment which methods comprise administering to the mammal a therapeutically effective amount of a compound of Formula (I), or a stereoisomer or prodrug thereof, or a pharmaceutically acceptable salt of the compound, stereoisomer, or prodrug; a combination of a compound of Formula (I), a stereoisomer or prodrug thereof, or a pharmaceutically acceptable salt of the stereoisomer or prodrug and an anti-obesity agent; a pharmaceutical composition comprising an effective amount of a compound of Formula (I), a stereoisomer or prodrug thereof, or a pharmaceutically acceptable salt of the compound, stereoisomer, or prodrug, and a pharmaceutically acceptable vehicle, carrier, or diluent; or a pharmaceutical composition comprising an effective amount of a compound of Formula (I), a stereoisomer or prodrug thereof, or a pharmaceutically acceptable salt of the compound, stereoisomer, or prodrug, and a pharmaceutically acceptable vehicle, carrier, or diluent, and an anti-obesity agent.

Preferably, the $\beta_3$ adrenergic receptor-mediated disease, condition, or disorder is selected from the group consisting of obesity, diabetes, irritable bowel syndrome, inflammatory bowel disease, esophagitis, duodenitis, Crohn's Disease, proctitis, asthma, intestinal motility disorder, ucler, gastritis, hypercholesterolemia, cardiovascular disease, urinary incontinence, depression, prostate disease, dyslipidemia, and airway inflammatory disorder.

The invention further provides methods of increasing the lean meat content in edible animals which methods comprise administering to the edible animal a lean meat increasing amount of a compound of Formula (I), a stereoisomer, or prodrug thereof, or a pharmaceutically acceptable salt of the compound, stereoisomer, or prodrug; a pharmaceutical composition comprising a lean meat increasing amount of a compound of Formula (I), a stereoisomer or prodrug thereof, or a pharmaceutically acceptable salt of the compound, stereoisomer, or prodrug, and a pharmaceutically acceptable vehicle, carrier, or diluent; or a pharmaceutical composition comprising a lean meat increasing amount of a compound of Formula (I), a stereoisomer or prodrug thereof, or a pharmaceutically acceptable salt of the compound, stereoisomer, or prodrug, and a pharmaceutically acceptable vehicle, carrier, or diluent, and an anti-obesity agent.

The compounds of Formula (I), the stereoisomers and prodrugs thereof, and the pharmaceutically acceptable salts of the compounds, stereoisomers, and prodrugs, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular anti-obesity agent being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The dosage of the anti-obesity agent will also be generally dependent upon a number of factors including the health of the subject being treated, the extent of treatment desired, the nature and kind of concurrent therapy, if any, and the frequency of treatment and the nature of the effect desired. In general, the dosage range of the anti-obesity agent is generally in the range of from about 0.001 to about 100 mg/kg body weight of the individual per day, preferably from about 0.1 to about 10 mg/kg body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of Formula (I), a stereoisomer or prodrug thereof, or a pharmaceutically acceptable salt of the stereoisomer or prodrug; or a compound of Formula (I), a stereoisomer or prodrug thereof, or a pharmaceutically acceptable salt of the stereoisomer or prodrug and an anti-obesity agent is administered to a subject in need of treatment therewith, preferably in the form of a pharmaceutical composition. In the combination aspect of the invention, the compound of Formula (I), a stereoisomer or prodrug thereof, or a pharmaceutically acceptable salt of the stereoisomer or prodrug and the anti-obesity agent may be administered either separately or in the pharmaceutical composition comprising both. It is generally preferred that such administration be oral. However, if the subject being treated is unable to swallow, or oral administration is otherwise impaired or undesirable, parenteral or transdermal administration will be appropriate.

According to the methods of the invention, when the compound of Formula (I), a stereoisomer or prodrug thereof, or a pharmaceutically acceptable salt of the stereoisomer or prodrug; or a compound of Formula (I), a stereoisomer or prodrug thereof, or a pharmaceutically acceptable salt of the stereoisomer or prodrug and an anti-obesity agent are administered together, such administration can be sequential in time or simultaneous with the simultaneous method being generally preferred. For sequential administration, the compound of Formula (I), the stereoisomer or prodrug thereof, or the pharmaceutically acceptable salt of the stereoisomer or prodrug and the anti-obesity agent can be administered in any order. It is generally preferred that such administration be oral. It is especially preferred that such administration be oral and simultaneous. When the compound of Formula (I), the stereoisomer or prodrug thereof, or the pharmaceutically acceptable salt of the stereoisomer or prodrug, and the anti-obesity agent are administered sequentially, the administration of each can be by the same or by different methods.

According to the methods of the invention, the compound of Formula (I), a stereoisomer or prodrug thereof, or a pharmaceutically acceptable salt of the stereoisomer or prodrug; or a compound of Formula (I), a stereoisomer or prodrug thereof, or a pharmaceutically acceptable salt of the stereoisomer or prodrug and an anti-obesity agent is preferably administered in the form of a pharmaceutical composition comprising a pharmaceutically acceptable carrier, vehicle, or diluent. Accordingly, the compound of Formula (I), a stereoisomer or prodrug thereof, or a pharmaceutically acceptable salt of the compound, stereoisomer, or prodrug; or a compound of Formula (I), a stereoisomer or prodrug thereof, or a pharmaceutically acceptable salt of the stereoisomer or prodrug and an anti-obesity agent can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection may comprise pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary pharmaceutical excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may further comprise suspending agents, as for example, ethoxylated isostearyl alcohols, polyoxyethylene sorbitol and sorbitan esters, microcrystalline cellulose, aluminum metahydroxide, bentonite, agar—agar, and tragacanth, or mixtures of these substances, and the like.

Compositions for rectal or vaginal administration preferably comprise suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration of the compounds of Formula (I), the stereoisomers and prodrugs thereof, and the pharmaceutically acceptable salts of the compounds, stereoisomers, and prodrugs; and the compounds of Formula (I), the stereoisomers and prodrugs thereof, and the pharmaceutically acceptable salts of the compounds, stereoisomers, and prodrugs and the anti-obesity agents, may comprise ointments, powders, sprays and inhalants. The active agent or agents are admixed under sterile condition with a pharmaceutically acceptable carrier, and any preservatives, buffers, or propellants that may be required. Opthalmic formulations, eye ointments, powders, and solutions are also intended to be included within the scope of the present invention.

The following paragraphs describe exemplary formulations, dosages, etc. useful for non-human animals. The administration of the compounds of Formula (I), the stereoisomers and prodrugs thereof, and the pharmaceutically acceptable salts of the compounds, stereoisomers, and prodrugs; and the compounds of Formula (I), the stereoisomers and prodrugs thereof, and the pharmaceutically acceptable salts of the compounds, stereoisomers, and prodrugs and the anti-obesity agents, can be effected orally or non-orally, for example, by injection.

An amount of a compound of Formula (I), or a stereoisomer or prodrug thereof, or a pharmaceutically acceptable salt of the compound, stereoisomer, or prodrug; or a compound of Formula (I), a stereoisomer or prodrug thereof, or a pharmaceutically acceptable salt of the compound, stereoisomer, or prodrug and an anti-obesity agent, is administered such that an effective dose is received, generally a daily dose which, when administered orally to an animal is usually between about 0.01 and about 1,000 mg/kg of body weight, preferably between about 0.01 and about 300 mg/kg of body weight.

Conveniently, the compound can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, the compound can also be added directly to the feed, as such, or in the form of an animal feed supplement, also referred to as a premix or concentrate. A premix or concentrate of the compound in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. It is important that the compound be thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of active compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the invention with a sufficient amount of animal feed to provide from about $10^{-3}$ to 500 ppm of the compound in the feed or water.

The preferred medicated swine, cattle, sheep and goat feed generally contain from 1 to 400 grams of active ingredient per ton of feed, the optimum amount for these animals usually being about 50 to 300 grams per ton of feed.

The preferred poultry and domestic pet feeds usually contain about 1 to 400 grams and preferably 10 to 400 grams of active ingredient per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of a compound of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

Paste formulations can be prepared by dispersing the active compound in a pharmaceutically acceptable oil such as peanut oil, sesame oil, corn oil or the like.

Pellets containing an effective amount of a compound, pharmaceutical composition, or combination of the present invention can be prepared by admixing a compound of the present invention with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry and swine breeders, utilization of the method of the present invention yields leaner animals which command higher sale prices from the meat industry.

The terms pharmaceutically acceptable salts, esters, amides, or prodrugs mean the carboxylate salts, amino acid addition salts, esters, amides, and prodrugs of a compound that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible.

The term "salts" refers to inorganic and organic salts of a compound of Formula (I), or a stereoisomer, or prodrug thereof. These salts can be prepared in situ during the final isolation and purification of a compound, or by separately reacting a compound Formula (I), or a stereoisomer or prodrug thereof with a suitable organic or inorganic acid and isolating the salt thus formed. Representative salts include the hydrobromide, hydrochloride, sulfate, bisulfate, nitrate, acetate, oxalate, besylate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, Berge, et al., J. Pharm. Sci., 66, 1–19 (1977).

The term "prodrug" means a compound that is transformed in vivo to yield a compound of Formula (I), a stereoisomer thereof, or a pharmaceutically acceptable salt of the compound or stereoisomer. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I), a stereoisomer thereof, or a pharmaceutically acceptable salt of the compound or stereoisomer, contains a carboxylic acid functional group, a prodrug can comprise an ester formed by the replacement of the hydrogen atom of the acid group with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound of Formula (I), or a stereoisomer thereof, comprises an alcohol functional group, a prodrug can be formed by the replacement of the hydrogen atom of the alcohol group with a group such as $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N-$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate).

If a compound of Formula (I), or a stereoisomer thereof, incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy$(C_1-C_6)$alkyl, amino$(C_1-C_4)$alkyl or mono-N- or di-N,N-$(C_1-C_6)$alkylaminoalkyl, —C(Y$_2$)Y$_3$ wherein Y$_2$ is H or methyl and Y$_3$ is mono-N- or di-N,N-$(C_1-C_6)$ alkylamino, morpholino, piperidin-1-yl or pyrrolidin-1-yl.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond, both the cis- and trans-forms, as well as mixtures, are embraced within the scope of the invention.

Diasteromeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention.

The compounds of Formula (I) may exist in unsolvated as well as solvated forms with pharmaceutically acceptable solvents such as water, ethanol, and the like, and it is intended that the invention embrace both solvated and unsolvated forms.

It is also possible that the compounds of Formula (I) may exist in different tautomeric forms, and all such forms are embraced within the scope of the invention. For example, all of the tautomeric forms of the imidazole moiety are included in the invention. Also, for example, all keto-enol or imine-enamine forms of the compounds are included in the invention.

It is also intended that the invention disclosed herein encompass compounds of Formula (I) that may be synthesized in vitro using laboratory techniques, such as those well known to the synthetic organic chemist of ordinary skill, or synthesized using in vivo techniques, such as through metabolism, fermentation, digestion, and the like. It is also intended that the compounds of Formula (I) may be synthesized using a combination of in vitro and in vivo techniques.

The present invention also embraces isotopically-labelled compounds of Formula (I), which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. The compounds of Formula (I), the stereoisomers and prodrugs thereof, and the pharmaceutically acceptable salts of the compounds, stereoisomers, or prodrugs which contain the aforementioned isotopes and/or other isotopes of other atoms are intended to be within the scope of this invention.

Certain isotopically-labelled compounds of Formula (I), for example those into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, may afford certain therapeutic advantages resulting from greater metabolic stability, for example increased in vivo half-life or reduced dosage requirements and, hence, may be preferred in some circumstances. Isotopically labelled compounds of Formula (I) can generally be prepared by carrying out the procedures analogous to those disclosed in the Schemes and/or in the Examples hereinbelow, by substituting an isotopically labelled reagent for a non-isotopically labelled reagent.

The compounds of Formula (I) may be prepared by processes which include those known, or those analogous to those known, in the chemical arts. Such processes for the preparation of the compounds of Formula (I) as defined hereinabove are illustrated according to the exemplary synthetic sequences set forth hereinbelow in Schemes I through III. Furthermore, Schemes IV through VI illustrate exemplary synthetic routes to the intermediates useful in the production of the compounds of Formula (I). Unless otherwise qualified, the meanings of the generic radicals are as indicated hereinabove.

In the synthetic sequence designated Scheme I, an appropriately substituted oxirane derivative (III) is condensed with an appropriately substituted amine (II) to produce a compound of Formula (I).

The amine derivatives (II) may be conveniently prepared as depicted in general Schemes IV, V, and VI hereinbelow, however, other methods of preparing such amine derivatives will be known to one of ordinary skill in the art having benefit of the teachings of the instant disclosure.

The oxirane derivatives (III) may be prepared according to known methods, including those set forth in, for example, U.S. Pat. Nos. 5,541,197, 5,561,142, 5,705,515, and 6,037,362, the disclosures of which are all incorporated herein by reference. Where available, such oxirane derivates may also be obtained from commercial sources.

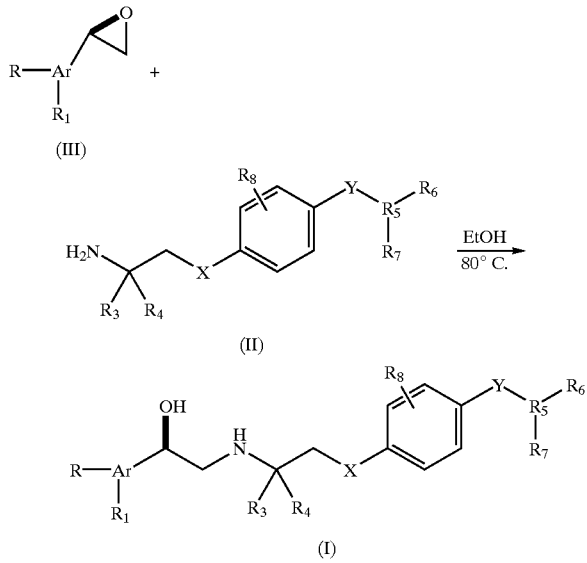

Scheme I

The condensation of oxirane (III) and amine (II) is most conveniently performed at an elevated temperature in a polar, protic solvent, for example, an alcohol such as methanol or ethanol. Alternatively, a co-solvent system may also be employed, for example, by adding a polar, aprotic co-solvent such as dimethylsulfoxide to the protic solvent. Isolation and purification of the compound of Formula (I) thus formed may then be effected according to known methods. An example of such condensation and purification is disclosed hereinbelow in the general preparative method denoted Method A.

Alternatively, as depicted in Scheme II, the compounds of Formula (I) may also be prepared by condensing an appropriately substituted protected alcohol (IV) with an amine (II). The protected alcohol (IV) incorporates a suitable leaving group that is susceptible to displacement by nucleophilic attack of the nitrogen atom of amine (II). Suitable leaving groups that may be employed in protected alcohol (IV) may comprise, for example, mesylates, tosylates, and nosylates, or halides, for example, chlorides, bromides, or iodides. The protected alcohol derivatives (IV) may be prepared according to known methods, including, for example, those methods disclosed in commonly-assigned U.S. Pat. No. 6,008,361, the disclosure of which is hereby incorporated by reference. However, other methods of preparing such protected alcohols will be known, or apparent in light of the instant disclosure, to one of ordinary skill in the art. See, for example, T. W. Greene, Protective Groups in Organic Synthesis, John Wiley & Sons, New York, (1991), and the references cited therein.

Scheme II

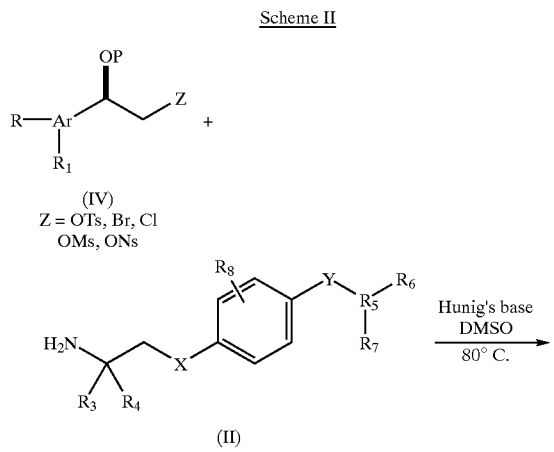

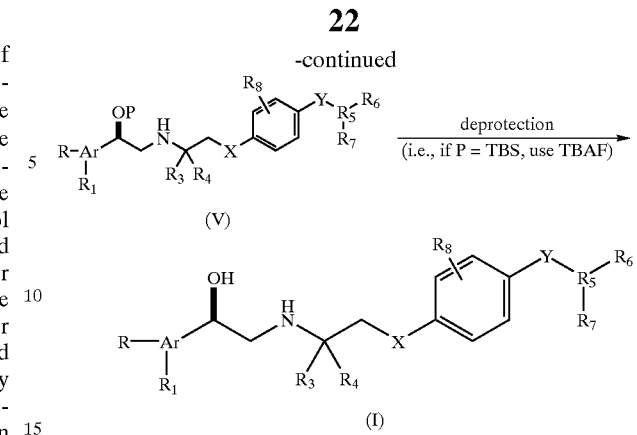

The condensation of protected alcohol (IV) and amine (II) is typically effected in the presence of an appropriate, sterically-hindered base, for example, N,N-diisopropylethylamine (Hunig's Base) in a polar, aprotic solvent, such as dimethylsulfoxide, at elevated termperature. The protected amino alcohol (V) thus formed may then be deprotected according to well-known preparative methods, for example, where (V) is a silylated derivative, preferably by treatment with tetrabutylammonium fluoride. An example of such condensation and deprotection is disclosed hereinbelow in the general preparative method denoted as Method B.

Alternatively, as shown in Scheme III, the compounds of Formula (I) may also be prepared by dehalogenation of a compound of Formula (Ia), wherein the Ar group represents an appropriately substituted 6-chloropyridine derivative.

Scheme III

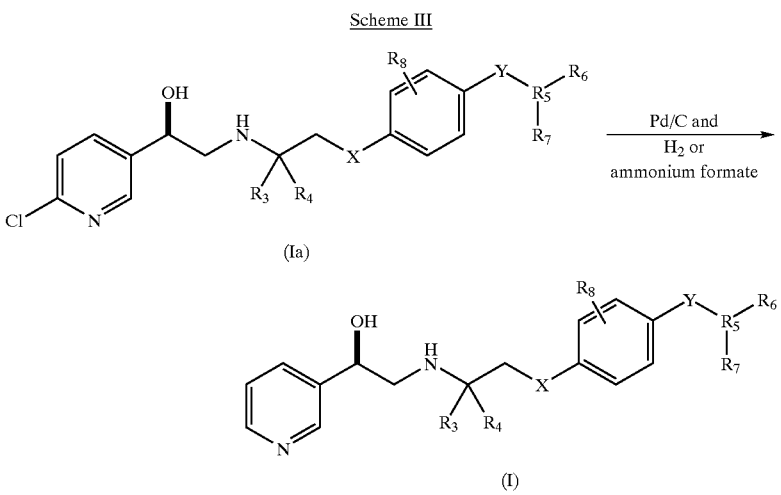

The dehalogenation of the above-mentioned 6-chloropyridine derivative (Ia) may be effected according to known methods. Most conveniently, such dehalogenation is performed using a metal catalyst, preferably palladium on carbon, in a polar solvent, such as methanol. The reaction is preferably conducted at room temperature over a period of several hours, i.e. overnight. Other methods of effecting dehalogenation reactions of this kind will be known to one of ordinary skill in the art. An example of such dehalogenation reaction is disclosed hereinbelow in the general preparative method denoted Method C.

With reference to Schemes I and II, the aforementioned amine derivatives of formula (II) may be prepared according to the exemplary synthetic sequences depicted hereinbelow in Schemes IV, V, and VI. It is to be understood, however, that such examples are offered for purposes of illustration of these embodiments of the instant invention and are not to be construed in any manner as limitations thereof, as other methods of preparing such amine derivatives will be known, or apparent, to one of ordinary skill in the art having benefit of the instant disclosure.

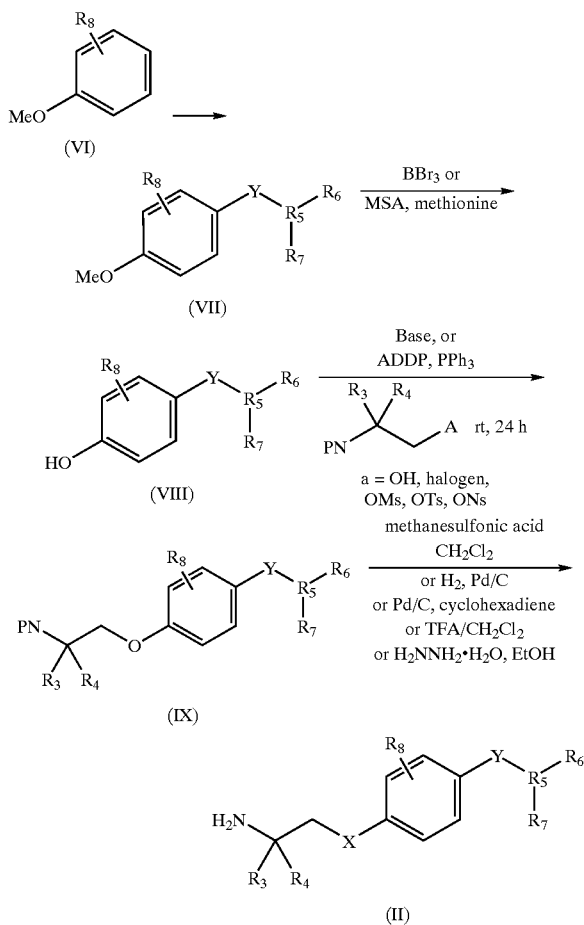

General Scheme IV hereinabove depicts a convenient, exemplary synthetic route to amine derivatives (II) in which an appropriately substituted anisole derivative (VI) serves as the synthetic platform upon which the heterocyclic moiety $R_5$ may be constructed. Such anisole derivatives will be well known to one of ordinary skill in the art and may either be prepared according to known methods or obtained commercially. The anisole derivatives (VI) may be functionalized as illustrated hereinbelow in Schemes IVa to IVc to produce heteroaryl derivatives (VII). Although general Scheme IV, and the synthetic schemes related thereto that are shown below, depict the use of an anisole derivative (VI), it is to be understood that an appropriately substituted phenol derivative may also be employed in place of the anisole derivative, where such phenol is chemically compatible with other functional groups and/or reagents that may be present or utilized in subsequent synthetic steps. The heteroaryl derivatives (VIII) so produced are then demethylated, for example, with methanesulfonic acid or boron tribromide, to form an appropriately substituted phenol derivative (VIII). The phenol derivative (VIII) so produced is then coupled with a protected amino alcohol to form the amine-protected derivative (IX). An example of such coupling reaction is provided hereinbelow in Example 1. The ability to select an appropriate amine-protecting group to form the amine-protected alcohol (IX) is well within the purview of one of ordinary skill in the art. For examples of typical amine protecting groups, see, for example, T. W. Greene, supra, and the references cited therein. The coupling reaction between the phenol derivative (VIII) and the amine-protected derivative (IX) may be effected according to methodologies that will be well-known to one of ordinary skill in the art, however, such coupling is preferably effected via a so-called Mitsunobu reaction. This reaction is typically performed with stirring at room temperature (or at elevated temperature if required) in the presence of a dehydrating agent, for example, a stoichiometric amount of a diazocarboxyl compound, such as 1,1'-(azodicarbonyl)-dipiperidine (ADDP), and a phosphine, for example, triphenylphosphine. The reaction can be carried out in any reaction-inert solvent such as tetrahydrofuran, dimethylformamide, or a hydrocarbon, or halogenated hydrocarbon solvent. The amine-protected derivative (IX) so formed is then deprotected in a conventional manner, for example, by treatment with methanesulfonic acid, or various other deprotecting agents under conditions that will be well known to one of ordinary skill in the art, including hydrogenoloysis in the presence of a suitable metal catalyst, such as palladium on carbon in an inert solvent. The hydrogenolysis reaction is typically effected anywhere from room temperature up to about 90° C. An example of such a deprotection reaction is provided hereinbelow in Example 2.

The following specific schemes, designated Schemes IVa to IVe, exemplify the syntheses of various synthetic precursors to the various amine derivatives (II) depicted in Schemes I, II, and IV wherein the heterocyclic moiety $R_5$ is as shown hereinbelow. As before, it is to be understood that these examples are offered for purposes of illustration, and not of limitation.

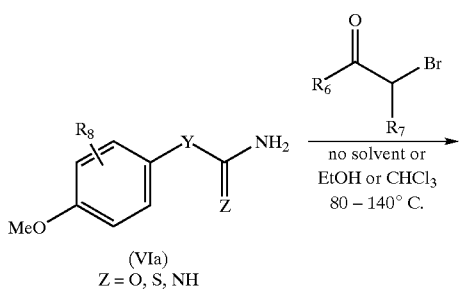

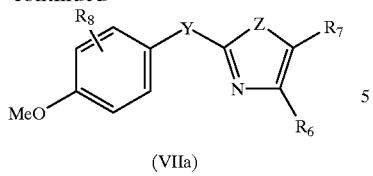

(VIIa)

The thiazole, oxazole, and imidazole-functionalized anisole derivatives (VIIa) may be produced according to the exemplary route depicted in Scheme IVa, beginning with an appropriately substituted thioamide, amide, or amidine derivative (VIa). Such thioamide, amide, or amidine derivatives will be well known to one of ordinary skill in the art and may either be obtained commercially or prepared by known preparative methods. The thioamide, amide, or amidine derivative (VIa) is cyclized with an appropriate α-bromoketone to form the desired derivative (VIIa). Such α-bromoketones will also be well known to one skilled in the art and may also be obtained commercially or prepared by one of ordinary skill in the art according to known methods.

Scheme IVb

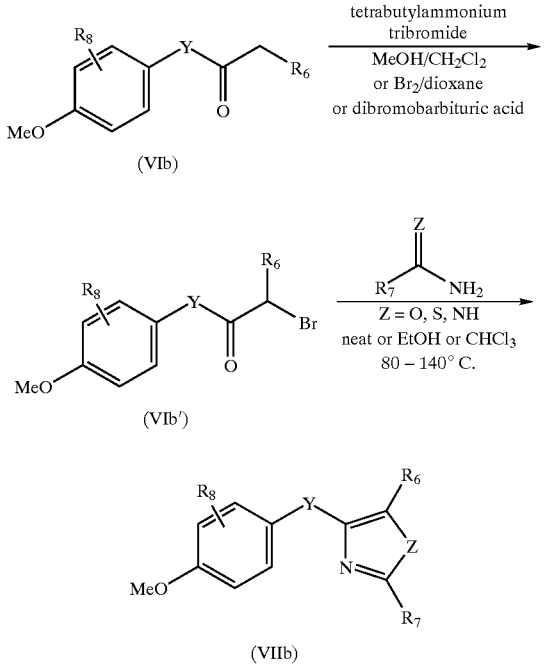

(VIb)

(VIb')

(VIIb)

Alternatively, regioisomeric thiazole, oxazole, and imidazole derivatives (VIIb) can be synthesized according to the exemplary synthetic route shown in Scheme IVb. In Scheme IVb, an appropriately substituted acylated anisole derivative (VIb) is α-halogenated, preferably α-brominated, according to conventional methods, for example, by the reaction of (VIb) with tetrabutylammonium tribromide (TBABBr$_3$), or dibromobarbituric acid (DBBA). The substituted α-bromoketone (VIb') so produced is then condensed with an appropriate thioamide, amide, or amidine derivative to form the thiazole, oxazole, or imidazole derivative (VIIb). Such condensation may be effected neat, or, preferably, in the presence of a polar solvent, such as an alcohol, or a halogenated hydrocarbon, such as chloroform.

Scheme IVc

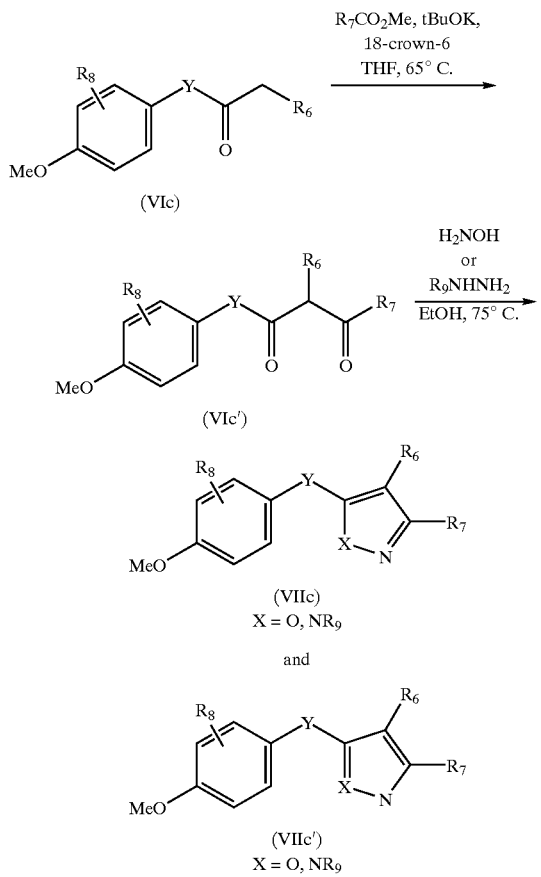

(VIc)

(VIc')

(VIIc)
X = O, NR$_9$ and (VIIc')
X = O, NR$_9$

The intermediate isoxazole or pyrazole derivatives (VIIc) may be synthesized according to the exemplary route depicted in Scheme IVc. In Scheme IVc, an acylated anisole derivative (VIc) is reacted with an appropriately substituted ester and a crown ether, for example, 18-crown-6, in the presence of an organic base, such as potassium tert-butoxide, in a non-protic solvent, such as tetrahydrofuran, at elevated temperature. The diketo derivative (VIc') thus formed is then cyclized with an appropriately substituted hydrazine derivative or hydroxylamine in a polar solvent, such as ethanol, at elevated temperature to produce pyrazole derivative (VIIc), and the regioisomer thereof (VIIc').

Scheme IVd

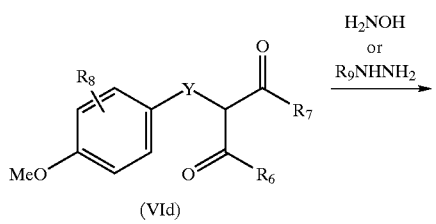

(VId)

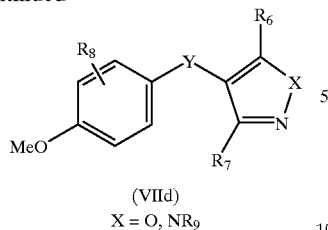

(VIId)
X = O, NR₉

The intermediate isoxazole or pyrazole derivatives (VIId) may be synthesized according to the exemplary route depicted in Scheme IVd. In Scheme IVd, an appropriately substituted diketo derivative (IVd) is condensed with an appropriately substituted hydrazine derivative or hydroxylamine to furnish phenol derivatives (VIId). The intermediate diketo derivative (VId) may be obtained from commercial sources or prepared according to known methods. The condensation reaction is preferably effected in a polar solvent, such as ethanol, at elevated temperature. An exemplary preparation of a compound of formula (VIIId) is provided in Example 35 hereinbelow.

Scheme IVe

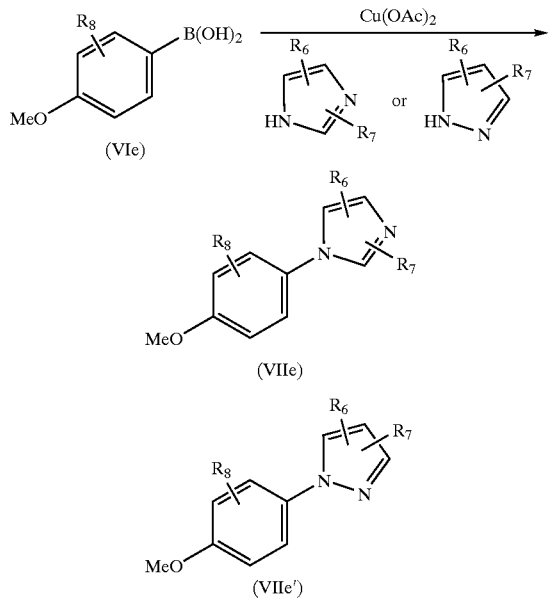

The intermediate imidazole derivatives (VIIe) or pyrazole derivatives (VIIe') may be prepared as outlined hereinabove in exemplary Scheme (IVe). As depicted in Scheme (IVe), an appropriately substituted boronic acid derivative (VIe) is reacted with an appropriately substituted imidazole or pyrazole derivative in the presence of a suitable catalyst, preferably copper (II) acetate, in a halogenated hydrocarbon solvent, preferably dichloromethane, to form imidazole derivative (VIIe) or pyrazole derivative (VIIe') respectively. The boronic acid derivatives (VIe), as well as the appropriately substituted imidazole or pyrazole derivatives, may be either obtained commercially or prepared according to known methods. An exemplary preparation of a compound of formula (VIIe') is provided in Example 30 hereinbelow.

Scheme V

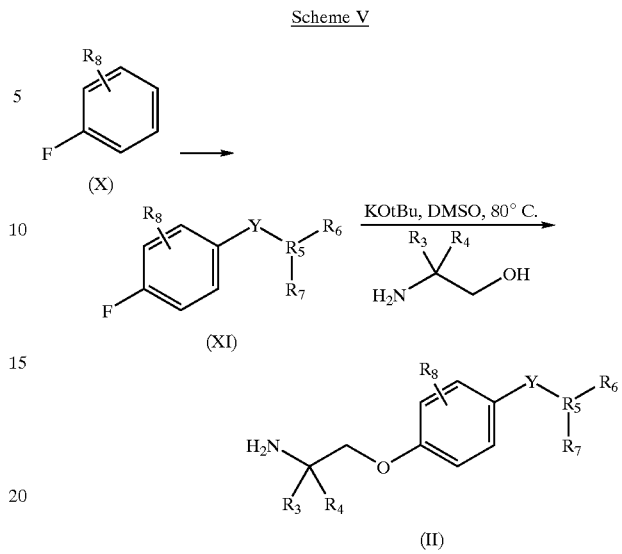

Scheme V hereinabove depicts an exemplary, alternative route to a formula (II) amine beginning with an appropriately substituted fluorobenzene derivative (X). Such fluorobenzene derivatives (X) may be obtained commercially, or, in the alternative, may be prepared by known methods. The fluorobenzene derivative (X), which serves as a synthetic scaffold from which the heterocyclic moiety $R_5$ is assembled, is reacted with an appropriately functionalized amino alcohol to furnish amine (II). The reaction between the amino alcohol and the fluorobenzene derivative (XI) is typically effected in a polar, aprotic solvent, preferably dimethylsulfoxide, at an elevated temperature in the presence of an organic or inorganic base, preferably potassium tert-butoxide. A representative synthesis of an amine (II) as depicted in Scheme V is provided hereinbelow in Examples 28 and 29.

Scheme Va

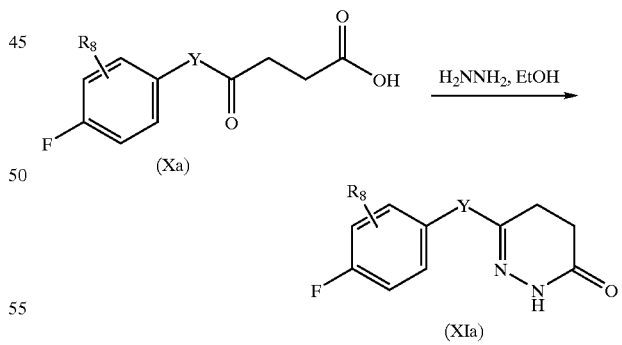

Scheme Va above illustrates a convenient, generally applicable synthetic approach to the heterocyclic amine precursor of formula (XI) shown in Scheme V, wherein $R_5$ represents a pyridazin-3-one moiety. Here, the fluorobenzene starting material (Xa) is condensed with hydrazine hydrate in a polar, protic solvent, such as ethanol, at elevated temperature, to form amine precursor (XIa). An exemplary synthesis of precursor (XIa) as shown in Scheme Va is disclosed hereinbelow in Example 28.

Scheme VI

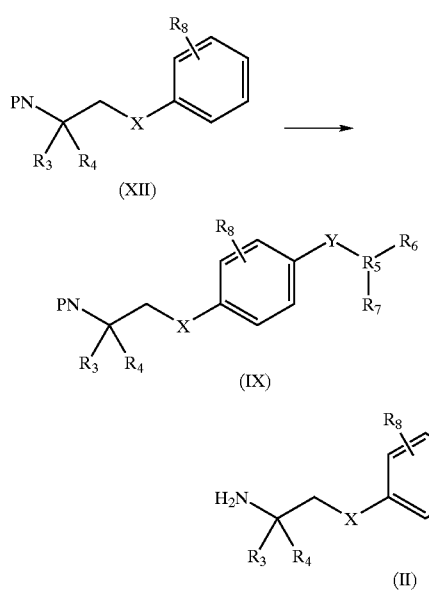

A generally applicable, alternative synthesis of an amine intermediate (II) is shown in Scheme VI beginning with protected amine (XII). The protected amine (XII), which may be prepared by known methods, is functionalized so as to form amine (IX) which subsequently serves as a synthetic basis for the preparation of protected amine (IX) which incorporates the substituted heterocyclic moiety $R_5$. Representative preparations of such heterocyclic moieties are illustrated hereinbelow in Schemes VIa to VId. Typically, the protected amine starting material (XII), wherein X is a direct bond, is prepared by appropriate derivatization of a commercially available phenalkylamine starting material. An example of such derivatization is disclosed hereinbelow in Example 11. Where X represents oxygen, such protected amine derivatives (XII) are typically derived from an aforementioned Mitsunobu coupling reaction between an appropriately substituted, commercially available phenol and an ethanolamine derivative. An example of such a coupling reaction is provided hereinbelow in Example 20.

Scheme VIa

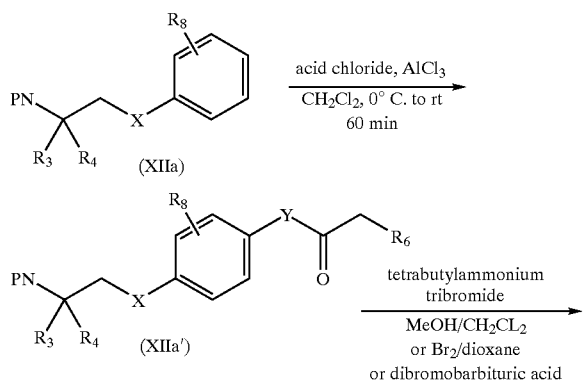

In Scheme VIa, the amine-protected derivative (XIIa) is acylated under standard Friedel-Crafts reaction conditions to form the acyl derivative (XIIa'). Such acylation will be well known to one of ordinary skill in the art and is typically effected by treating (XIIa) with an appropriately substituted acyl chloride in the presence of a Lewis acid, i.e. aluminum (III) chloride in a reaction-inert solvent, such as dichloromethane or similar halogenated hydrocarbon solvent at, or below, room temperature. The acylated derivate (XIIa) so produced is then α-halogenated relative to the keto group of the acyl moiety to form α-haloketone (XIIa''). Such α-halogenation, preferably α-bromination, may be effected according to conventional methods, preferably by the reaction of (XIIa) with tetrabutylammonium tribromide (TBABBr$_3$), or dibromobarbituric acid (DBBA). An example of such an α-bromination reaction is provided hereinbelow in Example 21. The preferred α-bromoketone (XIIa'') so produced is then condensed with an appropriate thioamide, amide, or amidine derivative to form a protected thiazole, oxazole, or imidazole derivative (IXa) respectively. Although the condensation reaction may be effected in the absence of a solvent, i.e. neat, for purposes of product purity and ease in reaction work-up and purification, it is generally preferred that the condensation reaction be performed in a reaction-inert solvent, including, for example, ethanol, chloroform, or similar solvent. An example of such condensation reaction is provided in Example 22 hereinbelow. The protected amine derivative (IXa) so produced may then be deprotected according to the methodologies described hereinabove in Scheme IV. An example of such deprotection reaction is provided hereinbelow in Example 23.

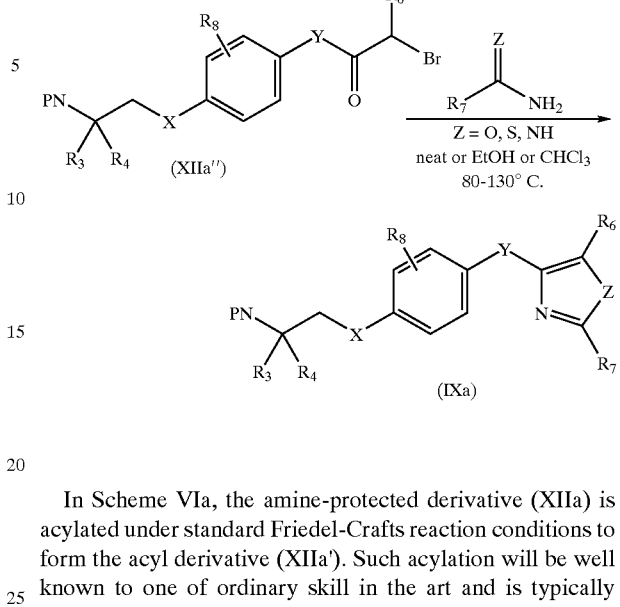

Scheme VIb

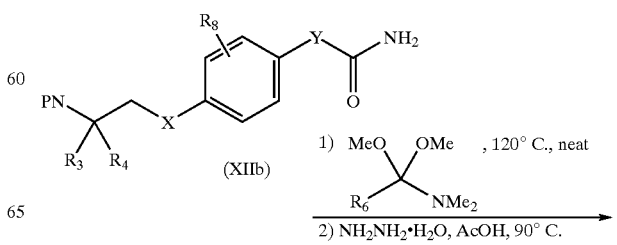

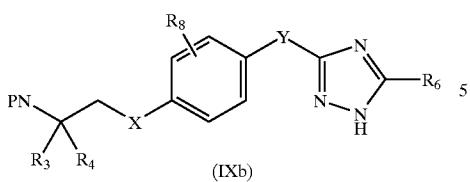

(IXb)

The protected triazole derivatives (IXb) shown in Scheme VIb may be produced by reaction of an amine-protected amide derivative (XIIb) with an appropriately substituted dimethylaminodimethylacetal at elevated temperature under neat conditions followed by treatment with hydrazine hydrate in glacial acetic acid, also at elevated temperature. The protected amine derivative (IXb) thus formed may then be deprotected as shown and described hereinabove in Scheme IV.

Scheme VIc

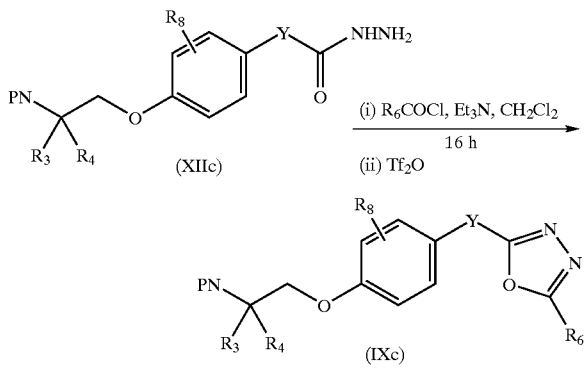

The oxadiazole derivatives (IXc) shown in Scheme VIc may be synthesized by reacting an appropriately substituted hydrazide (XIIc) with an acyl chloride under standard conditions, i.e., in the presence of a base, preferably an organic base such as triethylamine, in a reaction-inert solvent such as dichloromethane. If necessary, the resulting diacyl hydrazide intermediate may then be treated with a cyclizing agent, such as triflic anhydride, to effect ring closure. The protected amine derivative (IXc) thus produced may then be deprotected as shown and described hereinabove in Scheme IV. An exemplary synthetic sequence, which illustrates the preparation of a protected amine derivative (IXc), as well as the subsequent deprotection thereof, is provided in Examples 24 to 27 hereinbelow, wherein Y represents —CH$_2$—.

Scheme VId

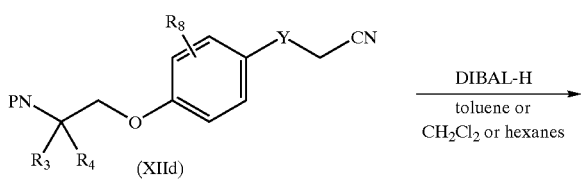

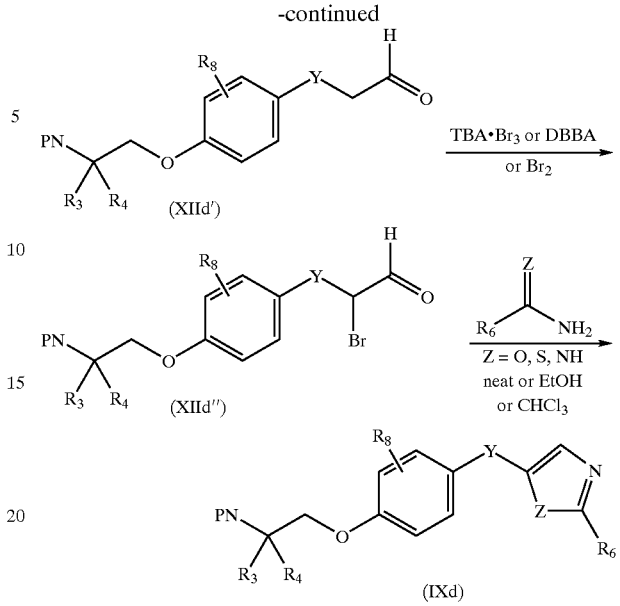

The protected thiazole, oxazole, or imidazole derivates (IXd) depicted in Scheme VId may be prepared beginning with nitrile (XIId). Typically, nitrile (XIId) is prepared via the aforementioned Mitsunobu coupling reaction between commercially available phenol and ethanolamine derivatives. Reduction of nitrile (XIId) with, for example, a metal hydride such as diisobutylaluminum hydride (DIBAL-H) in a reaction-inert, hydrocarbon solvent such as toluene or hexanes, or a halogenated hydrocarbon solvent such as dichloromethane furnishes aldehyde (XIId'). The aldehyde (XIId') so produced is then α-halogenated to form α-haloaldehyde (XIId''). Such α-halogenation is preferably effected as set forth hereinabove in Scheme VIa. The preferred α-bromoaldehyde (XIIa'') is then condensed with an appropriate thioamide, amide, or amidine derivative to form the protected thiazole, oxazole, or imidazole derivative (IXd), preferably also according to the method disclosed hereinabove in Scheme VIa. The protected amine derivative (IXd) so formed may then be deprotected as shown and described hereinabove in Scheme IV.

Conventional methods and/or techniques of separation and purification known to one of ordinary skill in the art can be used to isolate the compounds of Formula (I), as well as the various intermediates related thereto. Such techniques will be well-known to one of ordinary skill in the art and may include, for example, all types of chromatography (HPLC, column chromatography using common adsorbents such as silica gel, and thin-layer chromatography), recrystallization, and differential (i.e., liquid—liquid) extraction techniques.

EXPERIMENTAL

Chemical Syntheses

The embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

Example 1

{2-[4-(4-Methyl-oxazol-2-yl)-phenoxyl-ethyl}-Carbamic Acid Benzyl Ester

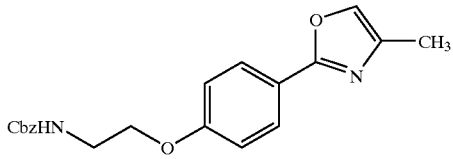

[2-(4-Carbamoyl-phenoxy)-ethyl]-carbamic acid benzyl ester (322 mg, 1.02 mmol) and 1-bromo-2,2-dimethoxypropane (3.8 g, 20.4 mmol) were combined in a round-bottomed flask and heated to about 130° C. for about thirty minutes. The reaction mixture was then cooled to room temperature and poured into water. The mixture was extracted with ethyl acetate, the combined extracts dried over magnesium sulfate, filtered, and concentrated in vacuo. The resulting crude material was purified by column chromatography (1:1 hexanes/ethyl acetate) to afford the desired oxazole product (167 mg, 47% yield). LRMS ([M+H]$^+$)= 353.1.

Example 2

2-[4-(4-Methyl-oxazol-2-yl)-phenoxyl-ethylamine

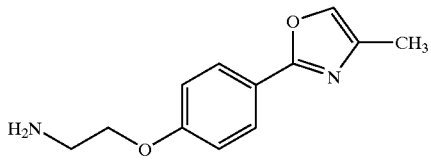

The title compound of Example 1, {2-[4-(4-Methyl-oxazol-2-yl)-phenoxy]-ethyl}-carbamic acid benzyl ester, (166 mg, 0.47 mmol) was dissolved in methanol (5 ml) and 10% Pd/C (50 mg) and 1,4-cyclohexadiene (192 mg, 2.4 mmol) were added to the resulting solution. The mixture was allowed to stir for about sixteen hours, and then it was filtered through diatomaceous earth, and the filter pad was washed with methanol. The filtrate was concentrated in vacuo to dryness, and the resulting material (92 mg, 90% yield), which was determined to be pure by $^1$H NMR, was used directly without further purification. LRMS ([M+H]$^+$)= 219.2.

Example 3

4-Hydroxy-thiobenzamide

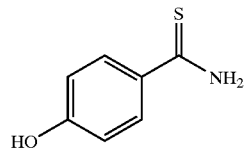

In a round bottomed flask, 4-hydroxybenzonitrile (5.00 g, 41.9 mmol), diethylthiophosphoric acid (7.02 g, 41.9 mmol), and water (8 ml) were heated with stirring to about 80° C. for about thirty minutes. An additional 10 ml of water was then added to the suspension, and the reaction was heated for about another one hour. The mixture was then allowed to stir for about sixteen hours at room temperature and was then extracted with water and 1:1 ether/ethyl acetate. The combined organic extracts were dried over magnesium sulfate, filtered, and concentrated in vacuo. The resulting solid was purified by column chromatography (silica gel; hexanes to ethyl acetate). The product was isolated as a yellow solid (5.54 g, 87% yield). $^1$H NMR (CD$_3$OD): δ6.74 (d, 2H, J=9.1 Hz), 7.83 (d, 2H, J=8.7 Hz).

Example 4

4-(4-Phenyl-thiazol-2-yl)-phenol

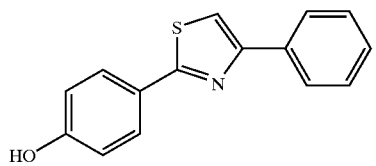

In a round-bottomed flask, 2-bromoacetophenone (520 mg, 2.61 mmol) and 4-hydroxy-thiobenzamide (400 mg, 2.61 mmol) were dissolved in ethanol (10 ml), and the resulting solution was heated to reflux. After about one hour, the reaction was cooled to about 35° C. and was allowed to stir for about an additional twelve hours. The reaction mixture was then concentrated in vacuo to an oil, the residue redissolved in ethyl acetate and methylene chloride, and extracted with saturated aqueous sodium bicarbonate. The combined extracts were then extracted with brine, dried over magnesium sulfate, filtered, and concentrated in vacuo to an oil. The crude product was purified by column chromatography (silica gel; methylene chloride to 2% methanol/methylene chloride). The title product was isolated as a white solid (516 mg, 78% yield). LRMS ([M+H]$^+$)=254.1.

Example 5

Benzyl-{2-[4-(4-phenyl-thiazol-2-yl)-phenoxyl-ethyl}-carbamate

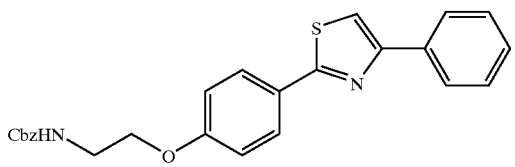

4-(4-Phenyl-thiazol-2-yl)-phenol (516 mg, 2.03 mmol) was dissolved in toluene (6.8 ml), and triphenylphosphine (786 mg, 3.00 mmol) and benzyl N-(2-hydroxyethyl)-carbamate (585 mg, 3.00 mmol) were added. The solution was cooled to about 0° C. and 1,1-(azodicarbonyl)-dipiperidine (757 mg, 3.00 mmol) was added. The mixture was allowed to stir for about 10 minutes at about 0° C. and was then allowed to warm to room temperature. An additional 6.8 ml of toluene and 6.8 ml of tetrahydrofuran were added to the viscous solution. The reaction mixture was stirred for about forty-eight hours, and then the solids were filtered off and rinsed with a minimum volume of 1:1 toluene/tetrahydrofuran. The filtrate was concentrated in vacuo to a semisolid which was then purified by column chromatography (silica gel; methylene chloride to 2% methanol/methylene chloride) to give 396 mg of pure product (45% yield). LRMS ([M+H]$^+$)=430.9.

Example 6

2-[4-(4-Phenyl-thiazol-2-yl)-phenoxyl-ethylamine

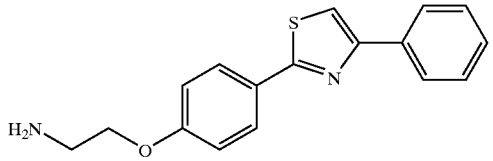

Benzyl-{2-[4-(4-phenyl-thiazol-2-yl)-phenoxy]-ethyl}-carbamate (396 mg, 0.92 mmol) was dissolved in methylene chloride (4.6 ml) and methanesulfonic acid (0.895 ml, 13.8 mmol) was added dropwise to give a homogenous yellow solution. The reaction mixture was allowed to stir for about sixteen hours, diluted with methylene chloride, and was brought to basic pH (12–13) with 1M sodium hydroxide. The mixture was then extracted with methylene chloride, and the combined organic extracts were dried over magnesium sulfate, filtered, and concentrated in vacuo. The resulting crude material was purified by column chromatography (silica gel; methylene chloride to 2% methanol/methylene chloride) to afford the product in 78% yield (213 mg). LRMS ([M+H]$^+$)=297.2.

Example 7

Benzyl-{2-[4-(2-methyl-1H-imidazol-4-yl)-phenoxyl-ethyl}-carbamate

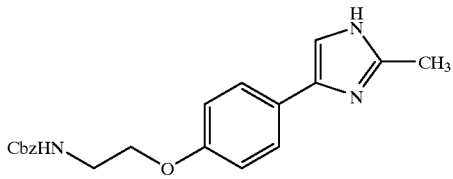

Acetamidine hydrochloride (112 mg, 1.18 mmol), benzyl-[2-(4-bromoacetyl-phenoxy)-ethyl]-carbamate (160 mg, 0.39 mmol), and sodium ethoxide (80.3 mg, 1.18 mmol) were combined in a round-bottomed flask, dissolved in ethanol, and heated to about 80° C. for about two hours. The reaction mixture was then allowed to cool to room temperature, and the resulting heterogenous mixture was filtered. The filtrate was then concentrated in vacuo to an oil which was purified by column chromatography (silica gel; 5% methanol/methylene chloride to 10% methanol/methylene chloride) to afford 92 mg (64% yield) of the desired product. LRMS ([M+H]$^+$)=352.2.

Example 8

2-[4-(2-Methyl-1H-imidazol-4-yl)-phenoxyl-ethylamine

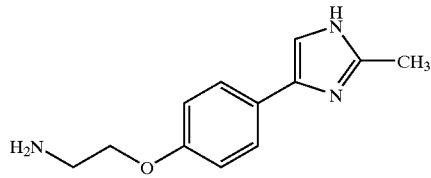

In a nitrogen-purged Parr flask, benzyl-{2-[4-(2-methyl-1H-imidazol-4-yl)-phenoxy]-ethyl}-carbamate (78 mg, 0.22 mmol) was dissolved in methanol (15 ml), and 10% Pd/C (20 mg) was added in one portion. The material was then hydrogenated at about 45 psi for about four hours. The reaction mixture was then filtered through a pad of diatomaceous earth and the filter pad was washed with methanol. The filtrate was concentrated in vacuo, and the resulting material (49 mg, 100% yield) was carried on without further purification. LRMS ([M+H]$^+$)=218.2.

Example 9

N-[2-(4-Acetyl-phenyl)-ethyl]-acetamide

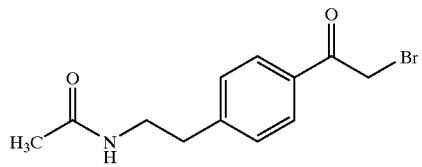

In a 500 ml flame-dried flask, N-phenethyl-acetamide (6.53 g, 40.0 mmol) was dissolved in methylene chloride (65 ml), and acetyl chloride (7.22 g, 92.0 mmol) was added in one portion. The resulting solution was cooled to about 0° C., and aluminum chloride (18.1 g, 136 mmol) was added in portions over about thirty minutes. The solution was stirred for about five minutes at about 0° C., and the ice bath was then removed and the mixture was heated to reflux for about thirty minutes. After cooling to room temperature, the reaction mixture was poured over ice water, stirred for about ten minutes, and then extracted with methylene chloride (2×100 ml). The combined organic extracts were then washed sequentially with water and brine, dried over magnesium sulfate, filtered, and concentrated in vacuo. The resulting white solid (7.52 g, 92% yield) was ascertained to be about 90% pure by NMR, and was employed directly without further purification. LRMS ([M+H]$^+$)=206.2.

Example 10

N-[2-(4-Bromoacetyl-phenyl)-ethyl]-acetamide

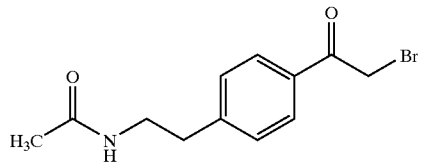

In a round-bottomed flask, N-[2-(4-acetyl-phenyl)-ethyl]-acetamide (7.23 g, 35.2 mmol) was dissolved in methylene chloride (120 ml), and methanol (60 ml). Tetrabutylammonium tribromide (17.0 g, 35.2 mmol) was added to this solution in one portion, and the mixture was allowed to stir overnight at room temperature. The volatiles were then removed in vacuo to afford an oil, which was then resuspended in 100 ml of methylene chloride and extracted with 125 ml of saturated aqueous sodium bicarbonate. The aqueous extracts were reextracted with methylene chloride (3×100 ml), and the combined organic extracts were then washed with water, dried over magnesium sulfate, filtered, and concentrated in vacuo. The crude oil was purified by column chromatography (silica gel; methylene chloride to 7% methanol/methylene chloride), and the resulting material was washed with 110 ml of water to afford 8.27 g (83% yield) of pure product as a white solid. LRMS ([M−1]$^-$)=283.0, 284.9.

Example 11

N-[2-[4-(2-Phenyl-thiazol-4-yl)-phenyl]-ethyl]-acetamide

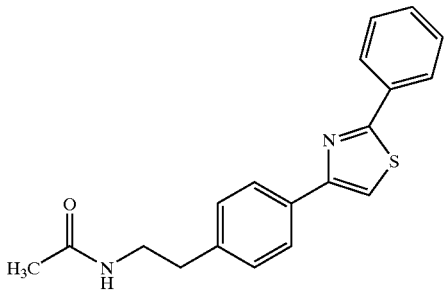

In a round-bottomed flask, thiobenzamide (357 mg, 2.60 mmol) and N-[2-(4-bromoacetyl-phenyl)-ethyl]-acetamide (740 mg, 2.60 mmol) were combined in ethanol (30 ml) and heated to about 80° C. for about three hours. The reaction mixture was then concentrated in vacuo to yield an off-white solid. The resulting material (838 mg, 100% yield) was ascertained to be pure by NMR and was carried into the next step directly without further purification. LRMS ([M+H]$^+$)= 323.2.

Example 12

2-[4-(2-Phenyl-thiazol-4-yl)-phenyl]-ethylamine

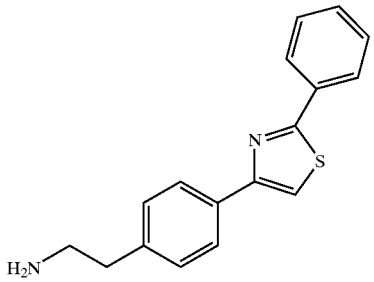

In a round-bottomed flask, N-{2-[4-(2-phenyl-thiazol-4-yl)-phenyl]-ethyl}-acetamide (838 mg, 2.60 mmol) was added to 5.0 ml of concentrated HCl and the resulting solution was heated to about 120° C. for about sixteen hours. The solution was then cooled to about 0° C., brought to pH 12 with 5M sodium hydroxide, and extracted with four portions of methylene chloride. The combined organic extracts were then washed with brine, dried over magnesium sulfate, and concentrated in vacua. The crude material was purified by column chromatography (silica gel; methylene chloride to 20% methanol/methylene chloride) to afford the product (617 mg, 85% yield). LRMS ([M+H]$^+$)=281.2.

Example 13

N-(1,1-Dimethyl-2-phenyl-ethyl)-2,2,2--trifluoroacetamide

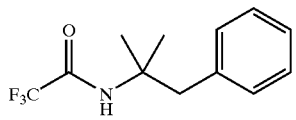

In a 500 ml flame-dried flask, phentermine hydrochloride (5.0 g, 26.9 mmol) and pyridine (7.0 ml, 86.2 mmol) were dissolved in methylene chloride (100 ml). The resulting solution was cooled to about 0° C., and trifluoroacetic anhydride (7.6 ml, 53.9 mmol) was added dropwise over about four minutes. The solution was stirred for about five minutes at about 0° C., and the ice bath was then removed. After stirring for about ninety minutes at room temperature, the reaction mixture was recooled to about 0° C. and 100 ml of saturated aqueous ammonium chloride was added. The organic and aqueous layers were then separated, and the aqueous layer was reextracted with another 100 ml portion of methylene chloride. The combined organic extracts were washed with brine, dried over magnesium sulfate, filtered, and concentrated in vacuo. The resulting white solid (6.35 g, 96% yield) was used without further purification. LRMS ([M−1]$^−$)=244.2.

Example 14

N-[2-(4-Acetyl-phenyl)-1,1-dimethyl-ethyl]-2,2,2-trifluoroacetamide

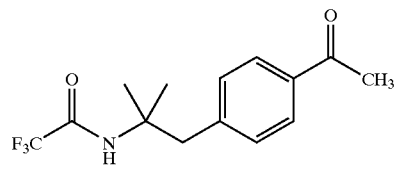

A flame-dried 250 ml flask was charged with N-(1,1-dimethyl-2-phenyl-ethyl)-2,2,2-trifluoroacetamide (5.93 g, 24.2 mmol), acetyl chloride (4.00 g, 55.6 mmol), and methylene chloride. The resulting solution was cooled to about 0° C., and aluminum (III) chloride (11.0 g, 82.2 mmol) was added in portions over about thirty minutes. Over the course of the addition, the solution changed from colorless to greenish-brown. After the addition was complete, the solution was heated to reflux for about thirty minutes, and was then cooled to room temperature and poured over 300 ml of ice water. After stirring for about ten minutes, the mixture was diluted with 125 ml of methylene chloride, and the layers were separated. The aqueous layer was extracted with an additional 125 ml of methylene chloride. The combined organic extracts were then washed with water and brine, sequentially, and then dried over magnesium sulfate, filtered, and concentrated in vacuo. The resulting oil, (6.9 g, 99% yield) which was ascertained to be about 85% pure by NMR, was carried into the subsequent reaction without further purification. LRMS ([M+1]$^+$)=288.2.

Example 15

N-[2-(Bromoacetyl-phenyl)-1,1-dimethyl-ethyl]-2,2,2-trifluoroacetamide

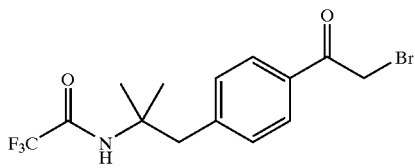

In a round-bottomed flask, N-(1,1-dimethyl-2-phenyl-ethyl)-2,2,2-trifluoroacetamide (6.90 g, 21.0 mmol) was dissolved in methylene chloride (66 ml) and methanol (33 ml). Tetrabutylammonium tribromide (10.6 g, 22.0 mmol) was added to this solution in one portion, and the mixture was allowed to stir at room temperature overnight. The volatiles were then removed in vacuo to an oil, which was then resuspended in 100 ml of methylene chloride and extracted with 125 ml of saturated aqueous sodium bicarbonate. The aqueous extracts were reextracted with methylene chloride (3×10 ml), and the combined organic extracts were then washed with water and dried over magnesium sulfate, filtered, and concentrated in vacuo. The crude oil was purified by column chromatography (silica gel; 60% methylene chloride/hexanes to 10% ethyl acetate/methylene chloride), and the resulting material (5.18 g) was recrystalized from hexanes to afford 3.14 g (41% yield) of pure product as a fluffy white solid.

Example 16

N-{1,1-Dimethyl-2-[4-(2-methyl-thiazol-4-yl)-phenyl]-ethyl}-2,2,2-trifluoroacetamide

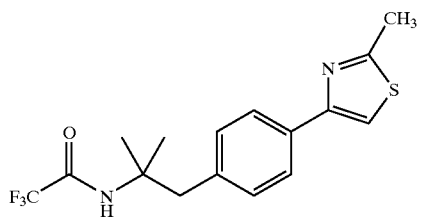

In a round-bottomed flask, N-[2-(bromoacetyl-phenyl)-1,1-dimethyl-ethyl]-2,2,2-trifluoroacetamide (388 mg, 1.06 mmol) and thioacetamide (80 mg, 1.06 mmol) were dissolved in ethanol (10 ml), and the mixture was heated to about 80° C. for about two and one-half hours. The reaction mixture was then concentrated in vacuo to an oil which was carried into the next reaction without further purification. LRMS ([M+1]$^+$)=343.2.

Example 17

1,1-Dimethyl-2-[4-(2-methyl-thiazol-4-yl)-phenyl]-ethylamine

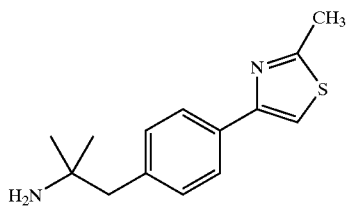

In a round-bottomed flask, N-{1,1-dimethyl-2-[4-(2-methyl-thiazol-4-yl)-phenyl]-ethyl}-2,2,2-trifluoroacetamide (~362 mg, 1.06 mmol) was suspended in 7.5 ml of 2:1 (v:v) methanol/tetrahydrofuran, and 5M sodium hydroxide (3.2 ml, 15 equiv.) was added dropwise. The solution turned from colorless to golden brown, and was then allowed to stir at room temperature overnight. The reaction mixture was then concentrated in vacuo to remove volatiles, and the residue was partitioned between ethyl acetate and saturated aqueous sodium bicarbonate. The aqeuous layer was removed and was washed twice more with ethyl acetate. The combined organic extracts were then washed with brine, dried over magnesium sulfate, filtered, and concentrated in vacuo to afford the product (242 mg, 93% yield for both steps), which was used directly without further purification. LRMS ([M+1]$^+$)=247.3.

Example 18 tert-Butyl-{2-[4-(5-methyl-4H-[1,2,4]-triazol-3-ylmethyl)-phenoxyl-ethyl}-carbamate

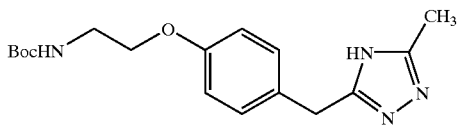

tert-Butyl-[2-(4-carbamoylmethyl-phenoxy)-ethyl]-carbamate (605 mg, 2.05 mmol) and N,N-dimethylacetamide dimethylacetal (5 ml) were combined and heated to about 120° C. for about ninety minutes. The orange solution was then allowed to cool to room temperature and was concentrated in vacuo. The resulting oil was then dissolved in acetic acid (6 ml), and hydrazine hydrate (0.20 ml, 4.10 mmol) was added to the solution. The mixture was heated to about 90° C. for about ninety minutes and was then poured into water and brought to pH 7 by adding 5M sodium hydroxide. The material was then partitioned between ethyl acetate and saturated aqueous sodium bicarbonate, and extracted with ethyl acetate. The combined organic extracts were washed with brine, dried over magnesium sulfate, filtered, and concentrated in vacuo. The crude material was purified by column chromatography (silica gel; chloroform to 4% methanol/chloroform) to afford 403 mg (59% yield) of the desired product. LRMS ([M+H]$^+$)=333.2.

Example 19

2-[4-(5-Methyl-4H-[1,2,4]triazol-3-ylmethyl)-phenoxy]-ethylamine

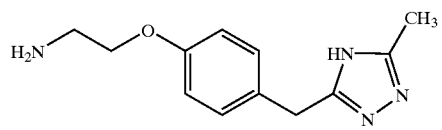

To a solution of tert-butyl-{2-[4-(5-methyl-4H-[1,2,4]triazol-3-ylmethyl)-phenoxy]-ethyl}-carbamate (380 mg, 1.14 mmol) in methylene chloride (10 ml) was added trifluoroacetic acid (1.7 ml). The resulting mixture was stirred for about thirty minutes and was then concentrated in vacuo. The resulting crude oil was then dissolved in ethyl acetate and brought to pH 10 with aqueous sodium hydroxide. The aqueous layer was extracted with ethyl acetate, and the combined organic extracts were washed with brine, dried over magnesium sulfate, filtered, and concentrated in vacuo to afford 120 mg (45% yield) of the amine product. LRMS ([M+H]$^+$)=233.1.

Example 20

Benzyl-[2-(4-acetyl-phenoxy)-ethyl]-carbamate

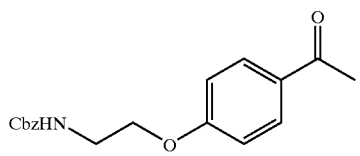

In around-bottomed flask equipped with a mechanical stirrer, 4-hydroxyacetophenone (5.00 g, 36.7 mmol) was dissolved in toluene (122 ml), and triphenylphosphine (14.4 g, 55.1 mmol), and benzyl N-(2-hydroxyethyl)carbamate (10.8 g, 55.1 mmol) were added. The reaction mixture was cooled to about 0° C., and 1,1'-(azodicarbonyl)dipiperidine (13.9 g, 55.1 mmol) was added in one portion. The mixture was allowed to warm to room temperature, and after stirring for about ten minutes, an additional 122 ml of toluene and 122 ml of tetrahydrofuran were added to the thick orange solution. The mixture was stirred for an additional twenty-four hours, and the solids were filtered off. The filtrate was concentrated in vacuo and the resulting solid was purified by column chromatography (silica gel; hexanes to 2:1 hexanes/ethyl acetate) to afford 9.68 g (84% yield) of the desired product as a white solid. LRMS ([M−1]⁻)=312.2.

Example 21

Benzyl-[2-(4-bromoacetylphenoxy)-ethyl]-carbamate

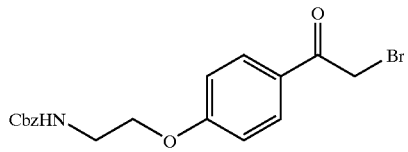

Benzyl-[2-(4-acetyl-phenoxy)-ethyl]-carbamate (10.2 g, 32.5 mmol) was dissolved in methylene chloride (100 ml) and methanol (50 ml), and tetrabutylamonium tribromide (15.7 g, 32.5 mmol) was added in one portion. The reaction mixture was stirred for about sixteen hours, and then quenched with water. The aqueous phase was extracted with ethyl acetate and then washed with saturated aqeous sodium bicarbonate, and saturated Na$_2$S$_2$O$_3$. The combined organic extracts were dried over magnesium sulfate, filtered, and concentrated in vacuo, and the resulting crude material was purified by column chromatography (silica gel; hexanes to 2:1 hexanes/ethyl acetate) to afford a colorless oil which solidified upon standing. (11.5 g, 90% yield).

Example 22

Benzyl-[2-[4-(2-methyl-oxazol-4-yl)-phenoxyl-ethyl]-carbamate

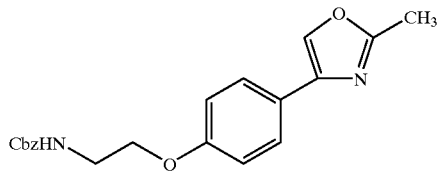

Acetamide (2.95 g, 50.0 mmol) and benzyl-[2-(4-bromoacetylphenoxy)-ethyl]-carbamate (1.20 g, 3.06 mmol) were combined in a round-bottomed flask and heated to about 130° C. for about ninety minutes. The reaction mixture was then allowed to cool to room temperature, and the resulting orange solid was partitioned between ethyl acetate and water and extracted three times with ethyl acetate. The combined organic extracts were washed with brine, dried over magnesium sulfate, filtered, and concentrated in vacuo. The resulting crude solid was purified by column chromatography (silica gel; methylene chloride to 10% ethyl acetate/methylene chloride) to afford 621 mg (58% yield) of the product as a white solid. LRMS ([M+H]⁺)=353.3.

Example 23

2-[4-(2-Methyl-oxazol-4-yl)-phenoxyl-ethylamine

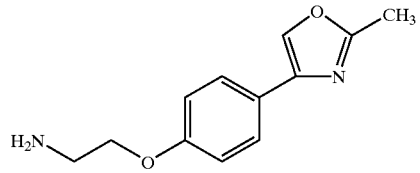

A round-bottomed flask containing benzyl-{2-[4-(2-methyl-oxazol-4-yl)-phenoxy]-ethyl}-carbamate (788 mg, 2.07 mmol) was purged with nitrogen, and 10% Pd/C (200 mg, 20 wt %), ethyl acetate (15 ml), and methanol (5 ml) were added. 1,4-cyclohexadiene (0.90 ml, 9.60 mmol) was then added to the mixture, and the solution was allowed to stir at room temperature for about one hour. The reaction mixture was then filtered through a pad of diatomaceous earth and the filter cake was washed with methanol. The filtrate was concentrated in vacuo and the residue purified by column chromatography (silica gel; methylene chloride to 20% methanol/methylene chloride) to afford 456 mg (89% yield) of the desired product. LRMS ([M+H]⁺)=247.2.

Example 24

Imidodicarbonic Acid, [2-[4-[2-[[(1,1-dimethylethoxy)carbonyl]methylamino]-2-oxoethyl]phenoxy]ethyl]-,bis(1,1-dimethylethyl)ester

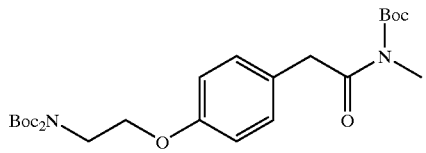

In a round-bottomed flask, 2-[4-(2-amino-ethoxy)-phenyl]-N-methyl-acetamide (7.78 g, 37.3 mmol) was dissolved in dimethylsulfoxide (30 ml), and di-tert-butyl dicarbonate (12.2 g, 55.9 mmol) was added in one portion at room temperature. After the reaction was stirred for about ninety minutes, dimethylaminopyridine (4.56 g, 37.3 mmol) and an additional 8.14 g (37.3 mmol) of di-tert-butyl dicarbonate were added. After a total of about four hours, an additional portion of dimethylaminopyridine (12.2 g, 55.9 mmol) was added, and the reaction was allowed to stir overnight. The mixture was then diluted with ether (150 ml) and poured into water (150 ml). The aqueous phase was extracted twice with ether, and the combined organic extracts were washed with brine, dried over magnesium sulfate, filtered, and concentrated in vacuo. The resulting crude material was then purified by column chromatography (silica gel; 5% ethyl acetate/hexanes to 35% ethyl acetate/hexanes) to afford the desired material (11.5 g, 22.6 mmol).

Example 25

Benzeneacetic acid, 4-[2-(bis[(1,1-dimethylethoxy)carbonyl]amino]ethoxy]-, Hydrazide

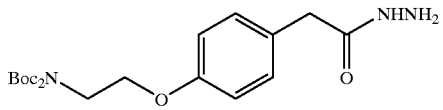

To a round-bottomed flask containing imidodicarbonic acid, [2-[4-[2-[[(1,1-dimethylethoxy)carbonyl]methylamino]-2-oxoethyl]phenoxy]ethyl]-, bis(1,1-dimethylethyl)ester (3.10 g, 6.09 mmol) in methanol (30 ml) was added hydrazine monohydrate (1.03 ml, 21.3 mmol) dropwise. The resulting solution was allowed to stir at room temperature overnight, and was then concentrated in vacuo to an oil. The residue was partitioned between methylene chloride and saturated aqueous sodium bicarbonate, and extracted with methylene chloride. The crude material was purified by column chromatography (silica gel; methylene chloride to 5% methanol/methylene chloride) to afford 1.63 g (65% yield) of the desired product as an oil which crystallized upon standing.

Example 26

Benzeneacetic acid, 4-[2-(bis[(1,1-dimethylethoxy)carbonyl]amino]ethoxy]-, 2-benzoylhydrazide

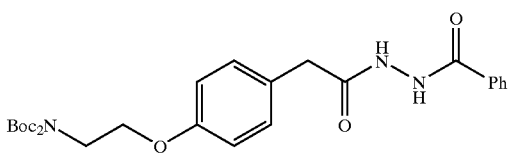

To a solution of benzeneacetic acid, 4-[2-(bis[(1,1-dimethylethoxy)carbonyl]amino]ethoxy]-, hydrazide (760 mg, 1.86 mmol) in dichloromethane (20 ml) was added benzoyl chloride (0.258 ml, 2.22 mmol) and triethylamine (0.310 ml, 2.22 mmol). The resulting solution was stirred for about twenty-four hours, quenched with saturated aqueous sodium bicarbonate, and extracted with methylene chloride. The combined organic extracts were dried over magnesium sulfate, filtered, and concentrated in vacuo to afford a crude solid. This material was purified by column chromatography (silica gel; hexanes to 50% ethyl acetate/hexanes) to afford 451 mg (47% yield) of the product as a white solid. LRMS ([M−H]⁻)=512.1.

Example 27

2-[4-(5-Phenyl-[1,3,4]oxadiazol-2-ylmethyl)-phenoxy]-ethylamine

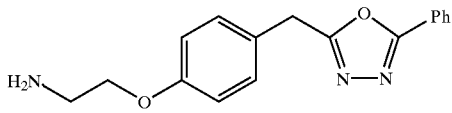

To a solution of benzeneacetic acid, 4-[2-(bis[(1,1-dimethylethoxy)carbonyl]amino]ethoxy]-, 2-benzoylhydrazide (435 mg, 0.847 mmol) in methylene chloride (12 ml) was added pyridine (0.150 ml, 1.86 mmol). The mixture was cooled to about −10° C., and triflic anhydride (0.299 ml, 1.78 mmol) was added dropwise. After the addition was complete, the cold bath was removed and the reaction mixture was stirred for about an additional one hour. The reaction was then quenched with saturated aqueous sodium bicarbonate and extracted three times with methylene chloride. The combined extracts were washed with brine, dried over magnesium sulfate, filtered, and concentrated in vacuo. The crude material was purified by column chromatography (silica gel; methylene chloride to 20% methanol/methylene chloride) to afford 60 mg (25% yield) of the product amine. LRMS ([M+H]⁺)=296.1.

Example 28

6-(4-Fluoro-phenyl)-4,5-dihydro-2H-pyridazin-3-one

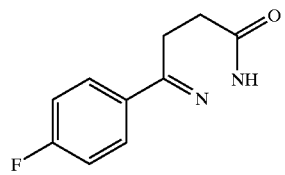

In a round-bottomed flask, 4-(4-fluoro-phenyl)-4-oxo-butyric acid (4.90 g, 25.0 mmol) and hydrazine hydrate (1.70 ml, 35.0 mmol) were dissolved in ethanol (50 ml), and the reaction mixture was heated to about 80° C. for about ninety minutes. The mixture was allowed to cool to room temperature and then concentrated in vacuo. The resulting solids were suspended and stirred in ethanol (10 ml) for ten minutes and the mixture was then filtered to give pure product (4.14 g, 21.5 mmol, 86% yield). LRMS ([M+H]⁺)= 193.2; m.p. 191–193° C.

Example 29

6-[4(2-Amino-ethoxy)-phenyl]-4,5-dihydro-2H-pyridazin-3-one

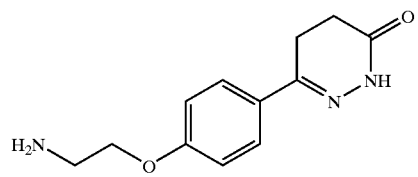

In a flame-dried, round-bottomed flask, ethanolamine (1.7 ml, 28.1 mmol) was dissolved in dimethylsulfoxide (9.5 ml), and potassium tert-butoxide (95%, 3.3 g, 28.1 mmol) was added to the solution. This mixture was stirred at about 65° C. for about ten minutes, and then 6-(4-fluorophenyl)-4,5-dihydro-2H-pyridazine-3-one (3.6 g, 18.7 mmol) was added. This dark-colored solution was heated to about 80° C. for about twelve hours, and was then cooled to room temperature. Water was added, and the resulting tan solid was removed by filtration. This crude solid was then purified by column chromatography (silica gel; 5% methanol/dichloromethane to 15% methanol/dichloromethane) to afford the product as a white solid (1.5 g, 34% yield). LRMS ([M+H]⁺)=234.2.

Example 30

1-(4-Methoxy-phenyl)-1H-pyrazole

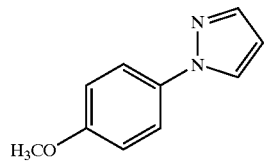

Copper (II) acetate (960 mg, 5.28 mmol) was added to a flame-dried flask charged with pyrazole (240 mg, 3.52 mmol), 4-methoxyphenylboronic acid (1.07 g, 7.04 mmol), 4 A molecular sieves (1.35 activated powder), and pyridine (570 µl, 7.04 mmol) in methylene chloride. The reaction was stirred for approximately two days at room temperature and then filtered through diatomaceous earth. The filtrate was concentrated in vacuo and purified by column chromatography (silica gel; isocratic 8% ethyl acetate/hexanes) to yield 381 mg (2.18 mmol, 62% yield) of the title compound. LRMS ([M+H]$^+$)=175.2.

Example 31

4 Pyrazole-1-yl-phenol

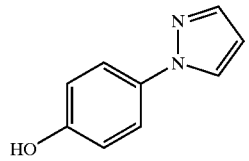

The title compound of Example 30, 1-(4-Methoxy-phenyl)-1H-pyrazole (400 mg, 2.30 mmol), was dissolved in methylene chloride (8 ml) and the solution was cooled to −78° C. Boron tribromide (1.0 M in methylene chloride, 5.05 ml) was added dropwise to the solution over about five minutes to afford a brown-colored solution. The reaction mixture was allowed to stir for about thirty minutes, the cooling bath was removed, and the mixture was allowed to stir at room temperature for about an additional three hours. The mixture was poured into water, and the resulting mixture was adjusted to about pH 8. The mixture was extracted with methylene chloride (3×25 ml), and the combined organic layers were dried over magnesium sulfate, filtered and concentrated in vacuo. The resulting crude material was purified by column chromatography (25% ethyl acetate/hexanes) to afford 183 mg (50% yield) of the desired product as an oil. LRMS ([M+H]$^+$)=161.1.

Example 32

2-(4-Pyrazole-1-yl-phenoxy)-ethylamine

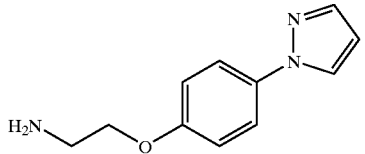

A round-bottomed flask was charged with 4-pyrazole-1-yl-phenol (175 mg, 1.09 mmol), and 3.6 ml of toluene, triphenylphosphine (430 mg, 1.64 mmol), and benzyl N-(2-hydroxyethyl)carbamate (320 mg, 1.64 mmol) were then added. The solution was cooled to 0° C. and 1,1′-(azodicarbonyl)-dipiperidine (414 mg, 1.64 mmol) was added. The mixture was allowed to stir for about ten minutes at about 0° C. and was then allowed to warm to room temperature. An additional 3.6 ml of toluene and 3.6 ml of tetrahydrofuran were added to the viscous solution. The reaction mixture was stirred for about forty-eight hours, and the precipitated solids were filtered off and washed with a minimum volume of 1:1 toluene/tetrahydrofuran. The filtrate was concentrated in vacuo to afford the intermediate [2-(4-pyrazole-1-yl-phenoxy)-ethyl]-carbamic acid benzyl ester as an oil which was used directly in the next step.

The crude benzyl ester above (1.23 g) was dissolved in methanol (5 ml), and 10% Pd/C (350 mg) and ammonium formate (315 mg, 5.0 mmol) were added to the resulting mixture. The mixture was allowed to stir for about sixteen hours, and was then filtered through diatomaceous earth. The filtrate was concentrated to dryness in vacuo, and the residue was then suspended in water and extracted with ethyl acetate. The combined extracts were dried over magnesium sulfate, filtered, and concentrated in vacuo. The resulting crude material was purified by column chromatography (15% methanol/methylene chloride) to afford 130 mg (57% yield for both steps) of desired product.

Example 33

2-[4-(5-Trifluoromethyl-1H-pyrazol-3-yl)-phenoxy]-ethylamine

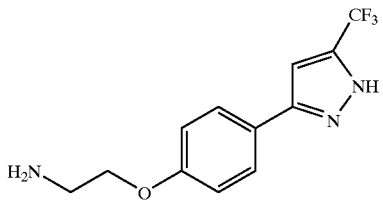

In a flame-dried, round-bottomed flask, ethanolamine (836 mg, 13.7 mmol) was dissolved in dimethylsulfoxide (2.7 ml), and potassium tert-butoxide (95%, 1.54 g, 13.7 mmol) was added to the solution. This mixture was stirred at about 65° C. for about ten minutes, and then 5-(4-fluoro-phenyl)-3-trifluoromethyl-1H-pyrazole (630 mg, 2.74 mmol) was added. The dark-colored solution was heated to about 85° C. for about eighteen hours, and was then allowed to cool to room temperature. Water was added, and the resulting tan-colored solid was collected by filtration. This crude product was purified by column chromatography (5% methanol/dichloromethane to 20% methanol/dichloromethane) to afford the product as a white solid (255 mg, 25% yield). LRMS ([M+H]$^+$)=272.2.

Example 34

4-[1,2,3]Thiadiazol-4-yl-phenol

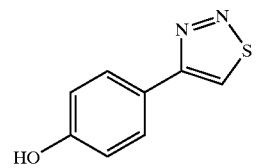

4-(4-methoxy-phenyl)-[1,2,3]thiadiazole (1.06 g, 5.50 mmol) was dissolved in methylene chloride (20 ml) and the solution was cooled to about −78° C. Boron tribromide (1.0 M in methylene chloride, 12.1 ml) was added dropwise to the solution to afford a brown-colored solution. The reaction mixture was allowed to stir for about fifteen minutes, the cooling bath was removed, and the mixture was allowed to stir at room temperature for about an additional twelve hours. The mixture was poured into water, and the resulting mixture was adjusted to about pH 6. The mixture was extracted with methylene chloride (3×100 ml), and the combined organic layers were dried over sodium sulfate, filtered, and concentrated in vacuo to afford 924 mg (94% yield) of the desired title compound as a tan solid. LRMS ([M+H]$^+$)=179.1.

Example 35

2-(4-[1,2,3]Thiadiazol-4-yl-phenoxy)-ethylamine

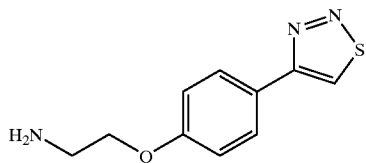

A round-bottomed flask was charged with 4-[1,2,3]thiadiazol-4-yl-phenol (875 mg, 4.90 mmol), and 16 ml of toluene, triphenylphosphine (1.93 g, 7.36 mmol), and benzyl N-(2-hydroxyethyl) carbamate (1.44 g, 7.36 mmol) were added. The solution was cooled to 0° C. and 1,1'-(azodicarbonyl)-dipiperidine (1.86 g, 7.36 mmol) was added. The mixture was allowed to stir for about ten minutes at about 0° C. and was then allowed to warm to room temperature. An additional 16 ml of toluene and 16 ml of tetrahydrofuran were added to the viscous solution. The reaction mixture was stirred for about forty-eight hours, and the precipitated solids were filtered off and washed with a minimum volume of 1:1 toluene/tetrahydrofuran. The filtrate was concentrated in vacuo to afford crude product which was purified by column chromatography (50% hexanes/ethyl acetate) to provide [2-(4-[1,2,3]thiadiazol-4-phenoxy)-ethyl]-carbamic acid benzyl ester (3.0 g, 57% yield).

The purified benzyl ester above was dissolved in methylene chloride (7 ml), and methanesulfonic acid (1.35 ml, 20.9 mmol) was added to the solution. The resulting solution was heated to about 35° C. for about two hours, and was then diluted with methylene chloride and water. The pH was adjusted to about 12 with 5N sodium hydroxide, and the mixture was extracted with methylene chloride. The combined organic extracts were dried over magnesium sulfate, filtered, and concentrated in vacuo. The resulting crude material was purified by column chromatography (20% methanol/methylene chloride) to afford 168 mg (59% yield) of desired amine product. LRMS ([M+H]$^+$)=222.2.

Example 36

4-(4-Methoxy-phenyl)-isoxazole

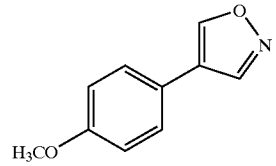

A round-bottomed flask was charged with potassium carbonate (1.45 g, 10.5 mmol) and ethanol (14 ml). To this mixture was added hydroxylamine hydrochloride (730 mg, 10.5 mmol), and 2-(4-methoxyphenyl)-malondialdehyde (1.25 g, 7.00 mmol). The reaction mixture was heated at about 80° C. for about three hours. The reaction mixture was then concentrated in vacuo to approximately one-quarter volume and partitioned between water and ethyl acetate. The mixture was extracted with ethyl acetate and the combined organic extracts were dried over magnesium sulfate, filtered, and concentrated in vacuo to a dark oil. This crude material was purified by column chromatography (10% ethyl acetate/hexanes) to afford 1.06 g (86% yield) of the desired product. LRMS ([M−H]$^-$)=174.1.

Example 37

4-Isoxazol-4-yl-phenol

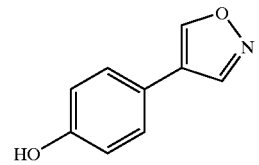

To a round-bottomed flask was added D,L-methionine (1.30 g, 8.73 mmol), 4-(4-methoxy-phenyl)-isoxazole (1.02 g, 5.82 mmol), and methanesulfonic acid (24 ml). The resulting solution was heated to about 70° C. for about eighteen hours, and was then allowed to cool to room temperature and poured onto ice water. The mixture was adjusted to about pH 4, and the heterogenous mixture was filtered. The solid was washed with water and then dried to yield the title compound as an off-white solid (640 mg, 68% yield). LRMS ([M−H]$^-$)=160.0.

Example 38

[2-(4-Isoxazol-4-yl-phenoxy)-ethyl]-Carbamic Acid Benzyl Ester

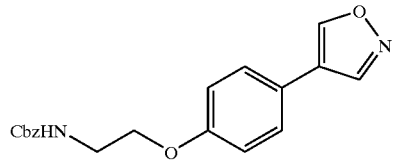

A round-bottomed flask was charged with 4-isoxazole-4-yl-phenol (570 mg, 3.54 mmol), and 12 ml of toluene, triphenylphosphine (1.39 g, 5.30 mmol), and benzyl N-(2-hydroxyethyl) carbamate (1.04 g, 5.30 mmol) were added. The solution was cooled to about 0° C. and 1,1'-(azodicarbonyl)-dipiperidine (1.34 g, 5.30 mmol) was added. The mixture was allowed to stir for about ten minutes at about 0° C., and the solution was then allowed to warm to room temperature. An additional 12 ml of toluene and 12 ml of tetrahydrofuran were added to the viscous solution. The reaction mixture was stirred for about twenty-four hours, and then the precipitated solids were filtered off and washed with a minimum volume of 1:1 toluene/tetrahydrofuran. The filtrate was concentrated to afford the crude product which was purified by column chromatography (30% ethyl acetate/hexanes) to afford the desired product as a white solid (1.06 g, 88% yield).

Example 39

2(4-Isoxazol-4-yl-phenoxy)-ethylamine

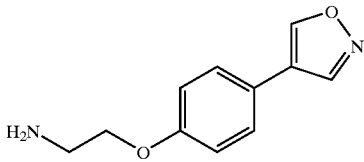

[2-(4-Isoxazol-4-yl-phenoxy)-ethyl]-carbamic acid benzyl ester (1.00 g, 2.81 mmol) was dissolved in methylene chloride (14 ml) and methanesulfonic acid (2.73 ml, 42.2 mmol) was added. The resulting mixture was heated to about 35° C. for about two hours, and was then diluted with methylene chloride and water. The pH of the mixture was adjusted to about 12 with 5N sodium hydroxide, and the mixture was extracted with methylene chloride. The combined extracts were dried over magnesium sulfate, filtered, and concentrated in vacuo. The resulting crude product was purified by column chromatography (20% methanol/methylene chloride) to afford 202 mg (53% yield) of the desired amine. LRMS ([M+H]$^+$)=205.3.

The compounds of Formula (I) may be prepared according to the three general preparative methods outlined hereinabove in Schemes I, II and III, denoted hereinbelow as Method A, Method B, and Method C, respectively, using appropriate synthetic precursors, including those precursors disclosed hereinabove in Examples 1 through 38, or those analogous thereto.

Method A (Scheme I)

(R)-1-(6-Chloro-pyridin-3-yl)-2-{2-[4-(4-phenyl-thiazol-2-yl)-phenoxy]-ethylamino}-ethanol

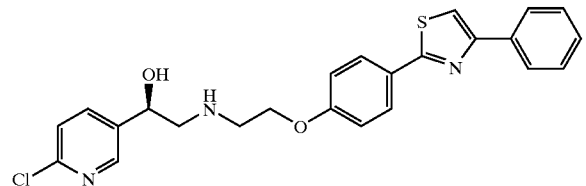

In a round-bottomed flask, (R)-2-chloro-5-oxiranyl-pyridine (U.S. Pat. No. 5,541,197) (73.0 mg, 0.477 mmol) and the title compound of Example 4 (2-[4-(4-phenyl-thiazol-2-yl)-phenoxy]-ethylamine) (212 mg, 0.716 mmol) were dissolved in 5 ml of ethanol, and the mixture was heated to about 80° C. for about sixteen hours. The solution was then concentrated in vacuo to an oil, and the crude material was purified by column chromatography (methylene chloride to 2% methylene chloride/methanol) to afford 107 mg (0.236 mmol, 50%) of the title compound as a white solid. LRMS ([M+H]$^+$)=452.2.

Utilizing appropriate starting materials, the following compounds were prepared in a manner analogous to that employed for the preparation of the title compound of Method A:

(R)-2-{2-[4-(4-benzofuran-2-yl-thiazol-2-yl)-phenoxy]-ethylamino}-1-(6-chloro-pyridin-3-yl)-ethanol;

(R)-2-{2-[4-(4-biphenyl-4-yl-thiazol-2-yl)-phenoxy]-ethylamino}-1-(6-chloro-pyridin-3-yl)-ethanol;

(R)-2-{2-[4-(2-butyl-thiazol-4-yl)-phenoxy]-ethylamino}-1-(6-chloro-pyridin-3-yl)-ethanol;

(R)-2-{2-[4-(2-tert-butyl-thiazol-4-yl)-phenoxy]-ethylamino}-1-(6-chloro-pyridin-3-yl)-ethanol;

(R)-N-[2-chloro-5-(2-{1,1-dimethyl-2-[4-(2-methyl-thiazol-4-yl)-phenyl]-ethylamino}-1-hydroxy-ethyl)-phenyl]-methanesulfonamide;

(R)-N-[2-chloro-5-(2-{1,1-dimethyl-2-[4-(2-phenyl-thiazol-4-yl)-phenyl]-ethylamino}-1-hydroxy-ethyl)-phenyl]-methanesulfonamide;

(R)-N-(2-chloro-5-(2-{2-[4-(2-ethyl-oxazol-4-yl)-phenoxy]-ethylamino}-1-hydroxy-ethyl)-phenyl]-methanesulfonamide;

(R)-N-[2-chloro-5-(2-{2-[4-(2-ethyl-thiazol-4-yl)-phenoxy]-ethylamino}-1-hydroxy-ethyl)-phenyl]-methanesulfonamide;

(R)-N-[2-chloro-5-(2-{2-[4-(2-ethyl-thiazol-4-yl)-phenyl]-1,1-dimethyl-ethylamino}-1-hydroxy-ethyl)-phenyl]-methanesulfonamide;

(R)-N-[2-chloro-5-(1-hydroxy-2-{2-[4-(2-isopropyl-1H-imidazol-4-yl)-phenoxy]-ethylamino}-ethyl)-phenyl]-methanesulfonamide;

(R)-N-(2-chloro-5-{1-hydroxy-2-{2-[4-(2-isopropyl-oxazol-4-yl)-phenoxy]-ethylamino}-ethyl)-phenyl]-methanesulfonamide;

(R)-N-[2-chloro-5-(1-hydroxy-2-{2-[4-(2-methyl-1H-imidazol-4-yl)-phenoxy]-ethylamino}-ethyl)-phenyl]-methanesulfonamide;

(R)-N-(2-chloro-5-(1-hydroxy-2-{2-[4-(2-methyl-oxazol-4-yl)-phenoxy]-ethylamino}-ethyl)-phenyl]-methanesulfonamide;

(R)-N-[2-chloro-5-(1-hydroxy-2-{2-[4-(2-methyl-thiazol-4-yl)-phenoxy]-ethylamino}-ethyl)-phenyl]-methanesulfonamide;

(R)-N-(2-chloro-5-{1-hydroxy-2-[2-(4-oxazol-4-yl-phenoxy)-ethylamino]-ethyl}-phenyl)-methanesulfonamide;

(R)-N-[2-chloro-5-(1-hydroxy-2-{2-[4-(2-phenyl-1H-imidazol-4-yl)-phenoxy]-ethylamino}-ethyl)-phenyl]-methanesulfonamide;

(R)-N-[2-chloro-5-(1-hydroxy-2-{2-[4-(2-pyridin-3-yl-1H-imidazol-4-yl)-phenoxy]-ethylamino}-ethyl)-phenyl]-methanesulfonamide;

(R)-N-[2-chloro-5-(1-hydroxy-2-{2-[4-(2-pyridin-4-yl-1H-imidazol-4-yl)-phenoxy]-ethylamino}-ethyl)-phenyl]-methanesulfonamide;

(R)-N-(2-chloro-5-{1-hydroxy-2-[2-(4-thiazol-4-yl-phenoxy)-ethylamino]-ethyl}-phenyl)-methanesulfonamide;

(R)-N-[2-chloro-5-(1-hydroxy-2-{2-[4-(2-trifluoromethyl-1H-imidazol-4-yl)-phenoxy]-ethylamino}-ethyl)-phenyl]-methanesulfonamide;

(R)-1-(6-chloro-pyridin-3-yl)-2-{2-[4-(2-cyclopentyl-thiazol-4-y)-phenoxy]-ethylamino}-ethanol;

(R)-1-(6-chloro-pyridin-3-yl)-2-{1,1-dimethyl-2-[4-(2-methyl-thiazol-4-yl)-phenyl]-ethylamino}-ethanol;

(R)-1-(6-chloro-pyridin-3-yl)-2-[1,1-dimethyl-2-(4-oxazol-4-yl-phenoxy)-ethylamino]-ethanol;

(R)-1-(6-chloro-pyridin-3-yl)-2-{2-[4-(2,5-dimethyl-oxazol-4-yl)-phenoxy]-ethylamino}-ethanol;

(R)-1-(6-chloro-pyridin-3-yl)-2-[1,1-dimethyl-2-(4-oxazol-5-yl-phenoxy)-ethylamino]-ethanol;

(R)-1-(6-chloro-pyridin-3-yl)-2-{1,1-dimethyl-2-[4-(2-phenyl-thiazol-4-yl)-phenyl]-ethylamino}-ethanol;

(R)-1-(6-chloro-pyridin-3-yl)-2-{2-[4-(2-ethyl-oxazol-4-yl)-phenoxy]-ethylamino}-ethanol;

(R)-1-(6-chloro-pyridin-3-yl)-2-(2-{4-[2-(2-ethyl-pyridin-4-yl)-thiazol-4-yl]-phenoxy}-ethylamino)-ethanol;

(R)-1-(6-chloro-pyridin-3-yl)-2-2-[3-(2-ethyl-thiazol-4-yl)-phenoxy]-ethylamino}-ethanol;

(R)-1-(6-chloro-pyridin-3-yl)-1-2-{2-[4-(4-ethyl-thiazol-2-yl)-phenoxy]-ethylamino}-ethanol;

(R)-1-(6-chloro-pyridin-3-yl)-2-{2-[4-(2-ethyl-thiazol-4-yl)-phenoxy]-ethylamino}-ethanol;

(R)-1-(6-chloro-pyridin-3-yl)-2-{2-[4-(2-ethyl-thiazol-4-yl)-phenyl]-ethylamino}-ethanol;

(R)-1-(6-chloro-pyridin-3-yl)-2-{2-[4-(2-ethyl-thiazol-4-yl)-phenyl]-1,1-dimethyl-ethylamino}-ethanol;

(R)-1-(6-chloro-pyridin-3-yl)-2-{2-[4-(2-isopropyl-1H-imidazol-4-yl)-phenoxy]-ethylamino}-ethanol;

(R)-1-(6-chloro-pyridin-3-yl)-2-{2-[4-(2-isopropyl-oxazol-4-yl)-phenoxy]-ethylamino}-ethanol;

(R)-1-(6-chloro-pyridin-3-yl)-2-{2-[4-(2-isopropyl-thiazol-4-yl)-phenoxy]-ethylamino}-ethanol;

(R)-1-(6-chloro-pyridin-3-yl)-2-(2-{4-[2-(4-methoxy-phenyl)-thiazol-4-yl-phenoxy}-ethylamino)-ethanol;

(R)-1-(6-chloro-pyridin-3-yl)-2-{2-[4-(2'-methyl-[2,4']bithiazolyl-4-yl)-phenoxy]-ethylamino}-ethanol;

(R)-1-(6-chloro-pyridin-3-yl)-2-{2-[4-(2-methyl-1H-imidazol-4-yl)-phenoxy]-ethylamino}-ethanol;

(R)-1-(6-chloro-pyridin-3-yl)-2-{2-[4-(2-methyl-oxazol-4-yl)-phenoxy]-]-ethylamino}-ethanol;

(R)-1-(6-chloro-pyridin-3-yl)-2-{2-[4-(5-methyl-oxazol-4-yl)-phenoxy]-ethylamino}-ethanol;

(R)-1-(6-chloro-pyridin-³-yl)-2-(2-{4-[2-(2-methyl-propane-2-sulfonylmethyl)-thiazol-4-yl]-phenoxy}-ethylamino)-ethanol;

(R)-1-(6-chloro-pyridin-3-yl)-2-{2-[4-(4-methyl-thiazol-2-yl)-phenoxy-ethylamino}-ethanol;

(R)-1-(6-chloro-pyridin-3-yl)-2-{2-[3-(2-methyl-thiazol-4-y)-phenoxy]-ethylamino}-ethanol;

(R)-1-(6-chloro-pyridin-3-yl)-2-{2-[4-(2-methyl-thiazol-4-yl)-phenoxy]-ethylamino}-ethanol;

(R)-1-(6-chloro-pyridin-3-yl)-2-{2-[4-(2-methyl-thiazol-4-yl)-phenyl]-ethylamino}-ethanol;

(R)-1-(6-chloro-pyridin-3-yl)-2-{2-[4-(5-methyl-1H-[1,2,4]triazol-3-ylmethyl)-phenoxy]-ethylamino}-ethanol;

(R)-1-(6-chloro-pyidin-3-yl)-2-[2-(4-oxazol-4-yl-phenoxy)-ethylamino]-ethanol;

(R)-1-(6-chloro-pyridin-3-yl)-2-[2-(4-oxazol-5-yl-phenoxy)-ethylamino]-ethanol;

(R)-1-(6-chloro-pyridin-3-yl)-2-{2-[4-(2-phenethyl-thiazol-4-yl)-phenoxy]-ethylamino}-ethanol;

(R)-1-(6-chloro-pyridin-3-yl)-2-{2-[4-(2-phenyl-1H-imidazol-4-yl)-phenoxy]-ethylamino}-ethanol;

(R)-1-(6-chloro-pyridin-3-yl)-2-{2-[4-(5-phenyl-[1,3,4]oxadiazol-2-ylmethyl)-phenoxy]-ethylamino}-ethanol;

(R)-1-(6-chloro-pyridin-3-yl)-2-{2-[4-(4-phenyl-thiazol-2-yl)-phenoxy]-ethylamino}-ethanol;

(R)-1-(6-chloro-pyridin-3-yl)-2-{2-[3-(2-phenyl-thiazol-4-yl)-phenoxy]-ethylamino}-ethanol;

(R)-1-(6-chloro-pyridin-3-yl)-2-{2-[4-(2-phenyl-thiazol-4-yl)-phenoxy]-ethylamino}-ethanol;

(R)-1-(6-chloro-pyridin-3-yl)-2-{2-[4-(2-phenyl-thiazol-4-yl)-phenyl]-ethylamino}-ethanol;

(R)-1-(6-chloro-pyridin-3-yl)-2-{2-[4-(2-propyl-thiazol-4-yl)-phenoxy]-ethylamino}-ethanol;

(R)-1-(6-chloro-pyridin-3-yl)-2-{2-[4-(1H-pyrazol-3-yl)-phenoxy]-ethylamino}-ethanol;

(R)-1-(6-chloro-pyridin-3-yl)-2-{2-[4-(2-pyridin-3-yl-1H-imidazol-4-yl)-phenoxy]-ethylamino}-ethanol;

(R)-1-(6-chloro-pyridin-3-yl)-2-{2-[4-(2-pyridin-4-yl-1H-imidazol-4-yl)-phenoxy]-ethylamino}-ethanol;

(R)-1-(6-chloro-pyridin-3-y)-2-{2-[3-(2-pyridin-3-yl-thiazol-4-yl)-phenoxy]-ethylamino}-ethanol;

(R)-1-(6-chloro-pyridin-3-yl)-2-{2-[3-(2-pyridin-4-yl-thiazol-4-yl)-phenoxy]-ethylamino}-ethanol;

(R)-1-(6-chloro-pyridin-3-yl)-2-{2-[4-(2-pyridin-3-yl-thiazol-4-yl)-phenoxy]-ethylamino}-ethanol;

(R)-1-(6-chloro-pyridin-3-yl)-2-{2-[4-(2-pyridin-4-yl-thiazol-4-yl)-phenoxy-ethylamino}-ethanol;

(R)-1-(6-chloro-pyridin-3-yl)-2-{2-[4-(2-pyridin-3-yl-thiazol-4-yl)-phenyl]-ethylamino}-ethanol;

(R)-1-(6-chloro-pyridin-3-y)-2-[2-(4-thiazol-2-yl-phenoxy)-ethylamino]-ethanol;

(R)-1-(6-chloro-pyridin-3-yl)-2-[2-(4-thiazol-4-yl-phenoxy)-ethylamino]-ethanol;

(R)-1-(6-chloro-pyridin-3-yl)-2-{2-[4-(2-thiophen-2-yl-1H-imidazol-4-yl)-phenoxy]-ethylamino}-ethanol;

(R)-1-(6-chloro-pyridin-3-yl)-2-{2-[4-(2-thiophen-2-yl-thiazol-4-yl)-phenoxy]-ethylamino}-ethanol;

(R)-1-(6-chloro-pyridin-3-yl)-2-{2-[4-(2-p-tolyl-thiazol-4-yl)-phenoxy]-ethylamino}-ethanol;

(R)-1-(6-chloro-pyridin-3-yl)-2-{2-[4-(4-p-tolyl-thiazol-2-yl)-phenoxy]-ethylamino}-ethanol;

(R)-1-(6-chloro-pyridin-3-yl)-2-{2-[4-(2-trifluoromethyl-1H-imidazol-4-yl)-phenoxy]-ethylamino}-ethanol;

(R)-1-(6-chloro-pyridin-3-yl)-2-(2-{3-[2-(4-trifluoromethyl-phenyl)-thiazol-4-yl]-phenoxy}-ethylamino)-ethanol;

(R)-1-(6-chloro-pyridin-3-yl)-2-(2-{4-[2-(4-trifluoromethyl-phenyl)-thiazol-4-yl]-phenoxy}-ethylamino)-ethanol;

(R)-1-(6-chloro-pyridin-3-yl)-2-{2-[4-(2-trifluoromethyl-thiazol-4-yl)-phenyl]-ethylamino}-ethanol;

(R)-1-(6-chloro-pyridin-3-yl)-2-{2-[4-(2-trifluoromethyl-thiazol-4-yl)-phenoxy]-ethylamino}-ethanol; and (R)-1-(6-chloro-pyridin-3-yl)-2-{2-[4-(4-trifluoromethyl-thiazol-2-yl)-phenoxy]-ethylamino}-ethanol.

Method B (Scheme II)

(R)-N-[5-(1-(tert-Butyl-dimethyl-silanyloxy)-2-{2-[4-(2-methyl-thiazol-4-yl)-phenoxy]-ethylamino}-ethyl)-pyridin-2-yl]-acetamide

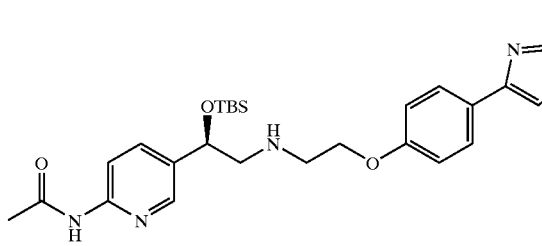

In a round-bottomed flask, 2-[4-(2-methyl-thiazol-4-yl)-phenoxy]-ethylamine (175 mg, 0.747 mmol) and toluene-4-sulfonic acid 2-(6-acetylamino-pyridin-3-yl)-2-(tert-butyl-dimethyl-silanyloxy)-ethyl ester (231 mg, 0.498 mmol) were dissolved in dimethylsulfoxide (0.50 mL), and diisopropyl ethyl amine (0.105 mL, 0.600 mmol) was added in one portion. The resulting mixture was heated to about 80° C. for about sixteen hours, and was then partitioned between diethyl ether and water. The aqueous phase was extracted with diethyl ether four times, and the combined organic extracts were then washed with brine, dried over magnesium sulfate, filtered, and concentrated in vacuo. The resulting white solid was purified by column chromatography (methylene chloride to 10% methanol/methylene chloride) to afford 117 mg (45%) of the desired product. LRMS ([M+1]$^+$): 527.1.

(R)-N-[5-(1-Hydroxy-2-{2-[4-(2-methyl-thiazol-4-yl)-phenoxy]-ethylamino}-ethyl)-pyridin-2-yl]-acetamide

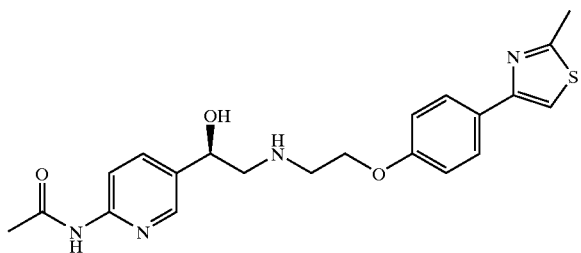

To a solution of (R)-N-[5-(1-(tert-butyl-dimethyl-silanyloxy)-2-{2-[4-(2-methyl-thiazol-4-yl)-phenoxy]-ethylamino}-ethyl)-pyridin-2-yl]-acetamide (115 mg, 0.218 mmol) in tetrahydrofuran (1.5 mL) was added tetrabutylammonium fluoride (1.0 M in tetrahydrofuran, 0.65 mL, 0.65 mmol) at room temperature. The resulting solution was allowed to stir for about two and one-half hours, and the reaction mixture was then partitioned between ethyl acetate and water. The pH of the mixture was adjusted to about 10–11, and the aqueous phase was then extracted with ethyl acetate. The combined organic extracts were washed with brine, dried over magnesium sulfate, filtered, and concentrated in vacuo. The resulting crude material was purified by column chromatography (methylene chloride to 20% methanol/methylene chloride) to afford 75 mg (83%) of the desired product. LRMS ([M+1]$^+$): 413.2.

(R)-1-(6-Amino-pyridin-3-yl)-2-{2-[4-(2-methyl-thiazol-4-yl)-phenoxy]-ethylamino}-ethanol

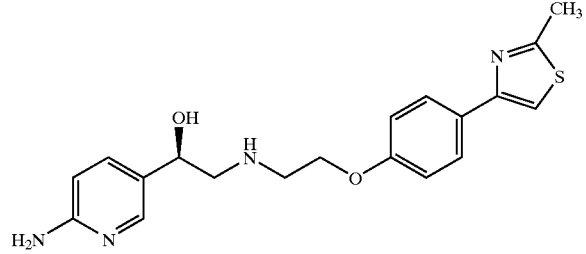

In a round-bottomed flask, (R)-N-[5-(1-hydroxy-2-{2-[4-(2-methyl-thiazol-4-yl)-phenoxy]-ethylamino}-ethyl)-pyridin-2-yl]-acetamide (74 mg, 0.18 mmol) was dissolved in 1.0 mL of ethanol, and 1.0 mL of 2 M sodium hydroxide was added to the solution. The reaction mixture was then heated to about 80° C. for about twenty minutes, and was then diluted with water and adjusted to about pH 11. The aqueous phase was extracted with four portions of methylene chloride, and the combined organic extracts were dried over magnesium sulfate, filtered, and concentrated in vacuo. The resulting crude material was purified by column chromatography (methylene chloride to 20% methanol/methylene chloride) to afford 49 mg (74%) of the desired product. LRMS ([M+1]$^+$): 371.2.

Method C (Scheme III)

2-{2-[4-(4-Phenyl-thiazol-2-yl)-phenoxyl-ethylamino}-1-pyridin-3-yl-ethanol

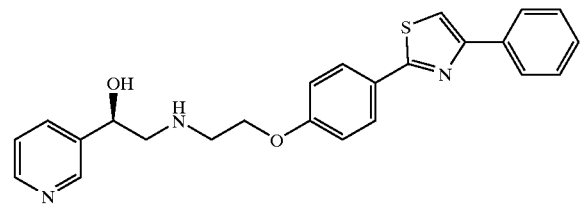

In a nitrogen-purged round-bottomed flask, 1-(6-chloro-pyridin-3-yl)-2-{2-(4-phenyl-thiazol-2-yl)-phenoxy]-ethylamino}-ethanol (107 mg, 236 mmol) was dissolved in a mixture of methanol (2.3 ml), THF (0.5 ml), and ethyl acetate (0.5 ml). Palladium on carbon (10%, 107 mg, 100 wt %) and ammonium formate (149 mg, 2.36 mmol) were then added sequentially. The reaction mixture was stirred overnight, filtered through diatomaceous earth, and the filter cake rinsed with ethyl acetate. The filtrate was concentrated to a white solid, which was purified by column chromatography (methylene chloride to 4% methanol/methylene chloride) to afford a pale yellow solid (44 mg, 44%). LRMS ([M+H]$^+$)=418.3.

Utilizing appropriate starting materials, the following compounds were prepared in a manner analogous to that employed for the preparation of the title compound of Method C:

(R)-1-(6-amino-pyridin-3-yl)-2-{2-[4-(2-methyl-thiazol-4-yl)-phenoxy]-ethylamino}-ethanol;

(R)-1-pyridin-3-yl-2-{2-[4-(2-pyridin-3-yl-1H-imidazol-4-yl)-phenoxy]-ethylamino}-ethanol;

(R)-1-pyridin-3-yl-2-{2-[4-(2-pyridin-4-yl-1H-imidazol-4-yl)-phenoxy]-ethylamino}-ethanol;

(R)-1-pyridin-3-yl-2-{2-[3-(2-pyridin-3-yl-thiazol-4-yl)-phenoxy]-ethylamino}-ethanol;

(R)-1-pyridin-3-yl-2-{2-[3-(2-pyridin-4-yl-thiazol-4-yl)-phenoxy]-ethylamino}-ethanol;

(R)-1-pyridin-3-yl-2-{2-[4-(2-pyridin-3-yl-thiazol-4-yl)-phenoxy]-ethylamino}-ethanol;

(R)-1-pyridin-3-yl-2-{2-[4-(2-pyridin-3-yl-thiazol-4-yl)-phenyl]-ethylamino}-ethanol;

(R)-1-pyridin-3-yl-2-{2-[4-(2-pyridin-4-yl-thiazol-4-yl)-phenoxy]-ethylamino}-ethanol;

(R)-1-pyridin-3-yl-2-[2-(4-[1,2,3]thiadiazol-5-ylphenoxy)-ethylamino]-ethanol;

(R)-1-pyridin-3-yl-2-[2-(4-thiazol-2-yl-phenoxy)-ethylamino]-ethanol;

(R)-1-pyridin-3-yl-2-[2-(4-thiazol-4-yl-phenoxy)-ethylamino]-ethanol;

(R)-1-pyridin-3-yl-2-{2-[4-(2-thiophen-2-yl-1H-imidazol-4-yl)-phenoxy]-ethylamino}-ethanol;

(R)-1-pyridin-3-yl-2-{2-[4-(2-thiophen-2-yl-thiazol-4-yl)-phenoxy]-ethylamino}-ethanol;

(R)-1-pyridin-3-yl-2-{2-[4-(4-p-tolyl-thiazol-2-yl)-phenoxy]-ethylamino}-ethanol;

(R)-1-pyridin-3-yl-2-{2-[4-(2-p-tolyl-thiazol-4-yl)-phenoxy]-ethylamino}-ethanol;

(R)-1-pyridin-3-yl-2-{2-[4-(4H[1,2,4-]triazol-3-yl)-phenoxy]-ethylamino}-ethanol;

(R)-1-pyridin-3-yl-2-{2-[4-(2-trifluoromethyl-1H-imidazol-4-yl)-phenoxy]-ethylamino}-ethanol;

(R)-1-pyridin-3-yl-2-(2-{3-[2-(4-trifluoromethyl-phenyl)-thiazol-4-yl]-phenoxy}-ethylamino)-ethanol;

(R)-1-pyridin-3-yl-2-(2-{4-[2-(4-trifluoromethyl-phenyl)-thiazol-4-yl]-phenoxy}-ethylamino)-ethanol;

(R)-1-pyridin-3-yl-2-{2-[4-(5-trifluoromethyl-2H-pyrazol-3-yl)-phenoxy]-ethylamino}-ethanol;

(R)-1-pyridin-3-yl-2-{2-[4-(4-trifluoromethyl-thiazol-2-yl)-phenoxy]-ethylamino}-ethanol; ethanol;

(R)-1-pyridin-3-yl-2-{2-[4-(2-trifluoromethyl-thiazol-4-yl)-phenyl]-ethylamino}-ethanol;

(R)-2-{2-[4-(2-yl-thiazol-2-yl)-phenoxy]-ethylamino}-1-pyridin-3-yl-ethanol;

(R)-2-{2-[4-(2-benzyloxymethyl-oxazol-4-yl)-phenoxy]-ethylamino}-1-pyridin-3-yl-ethanol;

(R)-2-{2-[4-(2-butyl-thiazol-4-yl)-phenoxy]-ethylamino}-1-pyridin-3-yl-ethanol;

(R)-2-{2-[4-(2-tert-butyl-thiazol-4-yl)-phenoxy]-ethylamino}-1-pyridin-3-yl-ethanol;

(R)-2-{2-[4-(2-cyclopentyl-thiazol-4-yl)-phenoxy]-ethylamino}-1-pyridin-3-yl-ethanol;

(R)-2-{1,1-dimethyl-2-[4-(2-methyl-thiazol-4-yl)-phenyl]-ethylamino}-1-pyridin-3-yl-ethanol;

(R)-2-{2-[4-(2,5-dimethyl-oxazol-4-yl)-phenoxy]-ethylamino}-1-pyridin-3-yl-ethanol;

(R)-2-[1,1-dimethyl-2-(4-oxazol-4-yl-phenoxy)-ethylamino]-1-pyridin-3-yl-ethanol;

(R)-2-[1,1-dimethyl-2-(4-oxazol-5-yl-phenoxy)-ethylamino]-1-pyridin-3-yl-ethanol;

(R)-2-{1,1-dimethyl-2-[4-(2-phenyl-thiazol-4-yl)-phenyl]-ethylamino}-1-pyridin-3-yl-ethanol;

(R)-2-{2-[4-(2-ethyl-oxazol-4-yl)-phenoxy]-ethylamino}-1-pyridin-3-yl-ethanol;

(R)-2-(2-{4-[2-(2-ethyl-pyridin-4-yl)-thiazol-4-yl]-phenoxy}-ethylamino)-1-pyridin-3-yl-ethanol;

(R)-2-{2-[3-(2-ethyl-thiazol-4-yl)-phenoxy]-ethylamino}-1-pyridin-3-yl-ethanol;

(R)-2-{2-[4-(4-ethyl-thiazol-2-yl)-phenoxy]-ethylamino}-1-pyridin-3-yl-ethanol;

(R)-2-{2-[4-(2-ethyl-thiazol-4-yl)-phenoxy]-ethylamino}-1-pyridin-3-yl-ethanol;

(R)-2-{2-[4-(2-ethyl-thiazol-4-yl)-phenyl]-1,1-dimethyl-ethylamino}-1-pyridin-3-yl-ethanol;

(R)-2-{2-[4-(2-ethyl-thiazol-4-yl)-phenyl]-ethylamino}-1-pyridin-3-yl-ethanol;

(R)-2-{2-[4-(2-hydroxymethyl-oxazol-4-yl)-phenoxy]-ethylamino}-1-pyridin-3-yl-ethanol;

(R)-6-{4-[2-(2-hydroxy-2-pyridin-3-yl-ethylamino)-ethoxy]-phenyl}-4,5-dihydro-2H-pyridazin-3-one;

(R)-2-{2-[4-(2-isopropyl-1H-imidazol-4-yl)-phenoxy]-ethylamino}-1-pyridin-3-yl-ethanol;

(R)-2-{2-[4-(2-isopropyl-oxazol-4-yl)-phenoxy]-ethylamino}-1-pyridin-3-yl-ethanol;

(R)-2-{2-[4-(2-isopropyl-thiazol-4-yl)-phenoxy]-ethylamino}-1-pyridin-3-yl-ethanol;

(R)-2-{2-[4-(2-methoxymethyl-oxazol-4-yl)-phenoxy]-ethylamino}-1-pyridin-3-yl-ethanol;

(R)-2-(2-{4-[2-(4-methoxy-phenyl)-thiazol-4-yl]-phenoxy}-ethylamino)-1-pyridin-3-yl-ethanol;

(R)-2-{2-[4-(2-methyl-1H-imidazol-4-yl)-phenoxy]-ethylamino}-1-pyridin-3-yl-ethanol;

(R)-2-{2-[4-(2'-methyl-[2,4']bithiazolyl-4-yl)-phenoxy]-ethylamino}-1-pyridin-3-yl-ethanol;

(R)-2-{2-[4-(5-methyl-[1,3,4]oxadiazol-2-yl)-phenoxy]-ethylamino}-1-pyridin-3-yl-ethanol;

(R)-2-[2-(3-methyl-4-oxazol-4-yl-phenoxy)-ethylamino]-1-pyridin-3-yl-ethanol;

(R)-2-{2-[4-(2-methyl-oxazol4-yl)-phenoxy]-ethylamino}-1-pyridin-3-yl-ethanol;

(R)-2-{2-[4-(5-methyl-oxazol-4-yl)-phenoxyl-ethylamino}-1-pyridin-3-yl-ethanol;

(R)-2-(2-{4-[2-(2-methyl-propane-2-sulfonylmethyl)-thiazol-4-yl]-phenoxy}-ethylamino)-1-pyridin-3-yl-ethanol;

(R)-2-{2-[4-(1-methyl-1H-pyrazol-3-yl)-phenoxy]-ethylamino}-1-pyridin-3-yl-ethanol;

(R)-2-{2-[4-(5-methyl-1H-[1,2,4]triazol-3-ylmethyl)-phenoxy]-ethylamino}-1-pyridin-3-yl-ethanol;

(R)-2-{2-[4-(4-methyl-thiazol-2-yl)-phenoxy]-ethylamino}-1-pyridin-3-yl-ethanol;

(R)-2-{2-[3-(2-methyl-thiazol-4-yl)-phenoxy]-ethylamino}-1-pyridin-3-yl-ethanol;

(R)-2-{2-[4-(2-methyl-thiazol-4-yl)-phenoxy]-ethylamino}-1-pyridin-3-yl-ethanol;

(R)-2-{2-[4-(2-methyl-thiazol-4-yl)-phenyl]-ethylamino}-1-pyridin-3-yl-ethanol;

(R)-2-{2-[4-(5-methyl-4H-[1,2,4]triazol-3-yl)-phenoxy]-ethylamino}-1-pyridin-3-yl-ethanol;

(R)-2-[2-(4-[1,3,4]oxadiazol-2-yl-phenoxy)-ethylamino]-1-pyridin-3-yl-ethanol;

(R)-2-[2-(4-oxazol-2-yl-phenoxy)-ethylamino]-1-pyridin-3-ylethanol;

(R)-2-[2-(4-oxazol-4-yl-phenoxy)-ethylamino]-1-pyridin-3-yl-ethanol;

(R)-2-[2-(4-oxazol-5-yl-phenoxy)-ethylamino]-1-pyridin-3-yl-ethanol;

(R)-2-{2-[4-(2-phenethyl-thiazol-4-yl)-phenoxyl-ethylamino}-1-pyridin-3-yl-ethanol;

(R)-2-{2-[4-(2-phenyl-1H-imidazol-4-yl)-phenoxy]-ethylamino}-1-pyridin-3-yl-ethanol;

(R)-2-{2-[3-(2-phenyl-thiazol-4-yl)-phenoxy]-ethylamino}-1-pyridin-3-yl-ethanol;

(R)-2-{2-[4-(2-phenyl-thiazol-4-yl)-phenoxy]-ethylamino}-1-pyridin-3-yl-ethanol;

(R)-2-{2-[4-(2-phenyl-thiazol-4-yl)-phenyl]-ethylamino}-1-pyridin-3-yl-ethanol;

(R)-2-{2-[4-(4-phenyl-thiazol-2-yl)-phenoxy]-ethylamino}-1-pyridin-3-yl-ethanol;

(R)-2-{2-[4-(5-phenyl-[1,3,4]oxadiazol-2-ylmethyl)-phenoxy]-ethylamino}-1-pyridin-3-yl-ethanol;

(R)-2-{2-[4-(2-propyl-thiazol-4-yl)-phenoxy]-ethylamino}-1-pyridin-3-yl-ethanol;

(R)-2-[2-(4-pyrazol-3-yl-phenoxy)-ethylamino]-1-pyridin-3-yl-ethanol; and (R)-2-{2-[4-(1H-pyrazol-3-yl)-phenoxy]-ethylamino}-1-pyridin-3-yl-ethanol.

Salt Formation

The hydrochloride salt forms of the compounds of Formula (I) may be prepared according to the following example.

The compound (R)-2-{2-[4-(4-phenyl-thiazol-2-yl)-phenoxy]-ethylamino}-1-pyridin-3-yl-ethanol (40 mg, 0.095 mmol) was dissolved in about 3 ml of methylene chloride, and 1.0 M HCl in diethylether (0.28 ml, 0.28 mmol) was added to the solution dropwise. The resulting cloudy suspension was concentrated in vacuo to afford 47 mg of a white solid.

Biological Assays

The utility of the compounds of Formula (I), the stereoisomers and prodrugs thereof, and the pharmaceutically acceptable salts of the compounds, stereoisomers, and prodrugs in the practice of the instant invention, can be evidenced by activity in at least one of the protocols described hereinbelow.

Assay 1

$\beta_3$ Receptor Selectivity Over $\beta_1$ and $\beta_2$ Adrenergic Receptors In vitro $\beta_3$ receptor agonist activity and selectivity over $\beta_1$ and $\beta_2$ adrenergic receptors may be determined by measurement of cyclic adenosine monophosphate (cAMP) accumulation in Chinese hamster ovary cells.

Chinese hamster ovary cells uniquely transfected with the cDNA for the human $\beta_1$, $\beta_2$, or $\beta_3$ adrenergic receptor are grown to confluence in Ham's F12 media (Gibco BRL, Life Technologies, Inc., Grand Island, N.Y.) containing 10% fetal bovine serum, 500 mg/ml geneticin, 100 U/ml penicillin, 100 mg/ml streptomycin, and 250 ng/ml fungizone according to the procedure described in American Type Culture Catalog of Cell Lines and Hybridomas, Seventh Edition, 1992, p. 36, ATCC CCL 61 CHO-K1. Compounds are prepared as 25 mM stock solutions in DMSO (0.1% DMSO final concentration), diluted in Ham's F12 media and added to the cells at $10^{-10}$ to $10^{-5}$ M along with $10^{-5}$ M isobutyl-methylxanthine to inhibit phosphodiesterase activity. The media and cells are then incubated for sixty minutes at 37° C. At the end of the incubation period, the media is aspirated and the cells lysed in 0.01 N HCl. The cellular content of cAMP is then determined by radioimmunoassay (RIA) using a kit from New England Nuclear (Burlington, Mass.). There is a direct correlation between the cellular content of cAMP and the agonism of the $\beta_1$, $\beta_2$, or $\beta_3$ adrenergic receptor. The non-selective, full $\beta$-adrenergic agonist isoproterenol is included as a positive control at $10^{-5}$ M.

Assay 2

Many G protein-coupled receptors (GPCRs) exhibit at least two agonist affinity states. High affinity agonist binding to GPCRs requires the association or coupling of the receptor with the GDP-bound heterotrimeric G protein complex. In general, the low affinity agonist binding site is indicative of the uncoupled receptor state. The high affinity agonist binding site can be converted to the low affinity site by addition of GTP or its analogs. In the absence of agonist, G proteins display high affinity for GDP. In the presence of agonist, G proteins display high affinity for GTP. Thus, when agonist and GTP are added to the receptor/G protein complex, GTP displaces GDP and uncouples the receptor from the G protein. Two affinity states for agonists can be detected in radioligand comptetetion binding assays. A two-site fit is generally observed for agonists for many GPCRs and can be calculated using commercially available software. The high affinity site ($K_{iH}$) corresponds to the G protein-coupled state and, in the case of $\beta_3$-adrenergic receptors correlates well with the functional $ED_{50}$ for stimulation of cAMP accumulation.

In order to identify compounds that attenuate the binding of [$^{125}$I]cyanopindolol (ICYP) to $\beta_3$ adrenergic receptors, the following radioligand binding assay can be used.

Radioligand Binding Assays

ICYP $\beta_3$ Adrenergic Receptor Competition Binding Assay

The specific activity of [$^{125}$I]CYP is 2000 Ci/mmole. ICYP undergoes catastrophic decay upon radiolysis. Therefore, the specific activity always remains at 2000 Ci/mmole, but the concentration will decrease over time. The final concentration of ICYP is 250 pM. Therefore, a 2.5 nM (10×) stock needs to be made. [$^{125}$I]CYP can be obtained from New England Nuclear, Boston, Mass.

Competitors

Up to four compounds can be tested in thirteen competition curves in a 96 well format. An example for a single compound is outlined below.

[Comp 1]

A 1,2 −10

B 1,2 −9.3

C 1,2 −9

D 1,2 −8.3

E 1,2 −8

F 1,2 −7.3

G 1,2 −7

H 1,2 −6.3

A 3,4 −6

B 3,4 −5

C 3,4 −4

D 1,3 pindolol

E 3,4 TOTAL

The next compound would begin in F 3,4. Two pairs of totals and non-specific binding are added to the plates.

Wells E 3,4 and G 7,8 are for total cpm bound.

Wells D 3,4 and H 7,8 are for 100 $\mu$M pindolol to determine non-specific binding.

To each well in order add:

20 µl buffer to "total" wells

20 µl 1 mM pindolol to pindolol wells

20 µl of each concentration of compound to the appropriate wells

20 µl of 2.5 nM ICYP to all wells

160 µl membranes diluted to 15 µg/160 µl

Procedure

1. Set up assay for Packard 96 well Unifilter with GF/C filters (Packard; Meriden, Conn.) using a 96 well microtiter plate.

2. Incubate 90–120 minutes with shaking at room temperature

3. Using Packard cell harvester (Packard; Meriden, Conn.), aspirate samples into processing head. Use a pre-soaked (0.3% PEI) filter.

4. Wash four times with cold wash buffer.

5. Dry plate, and add 25 µl Microscint (ICN Manufacturers; Costa Mesa, Calif.) to each well.

6. Count samples in Wallac beta plate reader (Wallac; Turku, Finland).

Binding Buffer 50 mM Hepes/10 mM $MgCl_2$, pH 7.4 (prepared from 10× stock solution) 0.2% BSA (fraction V)

Protease inhibitors (prepared as 100×stock solution)

100 µg/ml bacitracin

100 µg/ml benzamidine

5 µg/ml aprotin

5 µg/ml leupeptin

Wash Buffer 50 nM Hepes/10 mM $MgCl_2$, pH 7.4, ice cold (prepared from 10×stock solution)

Assay 3

Oxygen Consumption

As will be well known to one of ordinary skill in the art, during increased energy expenditure, animals generally consume increased amounts of oxygen. In addition, metabolic fuels such as, for example, glucose and fatty acids, are oxidized to $CO_2$ and $H_2O$ with the concomitant evolution of heat, an effect commonly referred to in the art as thermogenesis. Accordingly, the measurement of oxygen consumption in animals, including humans and companion animals, is an indirect measure of thermogenesis, and indirect calorimetry may be commonly used in animals, e.g., humans, by one of ordinary skill in the art, to measure such energy expenditures.

The ability of the compounds of Formula (I), the stereoisomers and prodrugs thereof, and the pharmaceutically acceptable salts of the compounds, stereoisomers, and prodrugs, to generate a thermogenic response may be demonstrated according to the following protocol using male Sprague-Dawley rats (Charles River, Wilmington, Mass.).

Whole animal oxygen consumption may be measured using an open circuit, indirect calorimeter (Oxymax™, Columbus Instruments, Columbus, Ohio). The gas sensors are calibrated with nitrogen gas and gas mixture (0.5% carbon dioxide, 20.5% oxygen, 79% nitrogen; Abco Industrial Supplies, Waterford, Conn.) before each experiment. Male Sprague-Dawley rats (300–380 g body weight) are placed in sealed chambers (43×43×10 cm) of the calorimeter and the chambers placed in activity monitors. Air flow rate through the chambers is set at 1.6–1.7 l/min. The calorimeter software calculates the oxygen consumption (ml/kg/hour) based on the flow rate of air through the chambers and the difference in oxygen content at inlet and outlet ports. The activity monitors have fifteen infrared light beams spaced one inch apart on each axis; ambulatory activity is recorded when two consecutive beams are broken (repeated interruptions of the same beam are not registered) and the results are recorded as counts. Basal oxygen consumption and ambulatory activity are measured every ten minutes for two and one-half to three hours. At the end of the basal period, the chambers are opened and the test compound (0.01–20 mg/kg, prepared in water, 0.5% methyl cellulose, or other suitable vehicle) or an equivalent amount of vehicle is administered by oral gavage. Oxygen consumption and amulatory activity are measured every ten minutes for an additional two to six hours post-dosing. Percent change in oxygen consumption is calculated by averaging the post-dosing values and dividing by basal oxygen consumption (average of the pre-dosing values except the first hour). Oxygen consumption values obtained during time periods where ambulatory activity exceeds 100 counts are excluded from the calculation. Thus, the values represent % change in resting oxygen consumption.

Assay 4

Hypoglycemic Activity

The compounds of Formula (I) may be tested for hypoglycemic activity accoprding to the following procedure, and as an aid in determining dosages when compared to other test compounds and standards.

Five to eight-week old C57 BL/6J-ob/ob mice (Jackson Laboratory, Bar Harbor, Me.) are housed five animals per cage at an ambient temperature of 66° C. under standard animal care practices. After a one week acclimation period, the animals are weighed and 25 microliters of blood is collected via an occular bleed prior to any treatment. The blood sample is immediately diluted 1:5 with saline containing 2% sodium heparin, in tubes held on ice. Blood samples are centrifuged for two minutes to remove red blood cells and the supernatant is analyzed for glucose concentration using a clinical autoanalyzer (Abbott Spectrum® CCx; Abbott Laboratories, Abbott Park, Ill.). Animals are then regrouped, in groups of five animals per cage, such that the mean glucose values of the groups are similar. The mice are then dosed once or twice daily for five days with test compound (0.01–20 mg/kg), with a positive control such as englitazone or ciglitazone (50 mg/kg p.o.) (U.S. Pat. No. 4,467,902; Sohda et al., Chem. Pharm. Bull., 32, 4460–4465, (1984)), or with vehicle. All compounds are administered by oral gavage in a vehicle consisting of 0.5% w/v methyl cellulose, or with other suitable vehicle. On Day 5, the animals are weighed again and bled (via the occular route) for blood glucose levels as described hereinabove. Plasma glucose is then calculated by the equation:

Plasma Glucose (mg/dl)=Sample Value×5×1.67=8.35×Sample Value where 5 is the dilution factor and 1.67 is the plasma hematocrit adjustment (assuming the hematocrit is 40%).

The animals dosed with vehicle maintain substantially unchanged hyperglycemic glucose levels (e.g. 300 mg/dl), while positive control animals have depressed glucose levels (e.g. 130 mg/dl). The glucose lowering activity of test compounds is expressed in terms of % glucose normalization. For example, a glucose level which is the same as the positive control is expressed as 100%.

Assay 5

β₁ and β₂ Receptor Selectivity

In vivo selectivity for $\beta_1$ and $\beta_2$ receptors may be determined by measurements of heart rate, blood pressure, and plasma potassium concentration gathered on conscious catheterized rats (male, Sprague-Dawley, 300–400 g body weight). To implant catheters, rats are anesthetized with pentobarbital (50–60 mg/kg i.p.) and the left carotid artery is cannulated with PE50 tubing. The catheter is tunneled subcutaneously, exteriorized at the back of the neck, filled with a solution of polyvinylpyrrolidone in heparinzied saline, flame sealed, and taped. Experiments are performed seven days after surgery. On the day of the experiment, the catheters are untaped and flushed with saline. After at least thirty minutes, basal values for heart rate and blood pressure are measured by attaching the catheter to a pressure transducer, the results recorded on a Grass Model 7 polygraph (Grass Medical Instruments, Quincy, Mass.), and a basal blood sample (0.5 ml) is obtained from the arterial catheter. After obtaining basal values, the test compound or vehicle is administered by oral gavage and blood pressure (measure of $\beta_2$ activity) and heart rate (measure of $\beta_1$ activity) measurements are taken at 15, 30, 45, and 60 minutes, and blood samples for potassium determination ($\beta_2$) are obtained at 30 and 60 minutes. Isoproterenol, a non-selective β-agonist, can be tested as a positive control at doses ranging from 0.001 to 1 mg/kg (injected s.c. in saline vehicle). Plasma potassium is determined by flame spectrophotometry. To determine changes, basal values are subtracted from the average of the post-dosing values.

Assay 6

Reducing Intestinal Motility

The compounds of Formula (I) have the effect of reducing intestinal motility and thus have utility in aiding in the treatment of various gastrointestinal disorders such as irritable bowel syndrome, peptic ulceration, esophagitis, gastritis, duodenitis (including that induced by *Helicobacter pylori*), intestinal ulcerations (including inflammatory bowel disease, ulcerative colitis, Crohn's Disease and proctitis), and gastrointestinal ulcerations. It has been proposed that the motility of non-sphincteric smooth muscle contraction is mediated by activity at $\beta_3$ adrenergic receptors. The availability of a $\beta_3$ specific agonist, with little activity at $\beta_1$ and $\beta_2$ receptors, will assist in the pharmacologic control of intestinal motility without concurrent cardiovascular effects.

In vivo activity of the compounds of Formula (I) for the treatment or prevention of intestinal motility disorders can be determined according to the following procedures. Eighteen-hour fasted male Sprague-Dawley derived (CD) rats (175–225 g) are dosed with 0.01–20 mg/kg p.o. of test compound or vehicle (distilled water). Thirty minutes after administration of test compound, the rats are orally dosed with 0.25 ml of a solution of sodium chromate in 0.9% saline containing about 20,000 cpm of $^{51}$Cr (specific activity 350 mCi/mg Cr). Twenty minutes later, the rats are sacrificed, the gastroesophageal, pyloric, and ileocecal junctions are then ligated, and the stomachs and small intestines are removed. The small intestines are then divided into ten equal lengths, and the stomach and each length of intestine assayed for radioactivity with a gamma counter. Gastric emptying rate may then be determined for each rat by comparing the amount of radioactivity in the intestine relative to the total in the intestine plus stomach. In addition, the geometric center of the distribution of the radioactive marker is then used as a measure of the overall transit rate through the stomach and intestine. The geometric center is calculated by summing the products of the fractions of $^{51}$Cr in each segment times the segments number: geometric center=S ((fraction of $^{51}$Cr per segment)×(segment number)). For these calculations, the stomach is considered segment number 0, and and the ten intestinal segments as numbers 1 to 10. Thus, a geometric center of 0.0 indicates that the entire load of $^{51}$Cr remains in the stomach. Data from the two experiments are pooled, and statistical evaluations are made using Dunnett's multiple comparison test.

Alternatively, in groups of eight, overnight-fasted male Sprague-Dawley (CD) rats (175–225 g) may be anesthetized with methoxyflurane. A small abdominal incision is then made, and the pylorus ligated. Immediately after the ligation, a solution of the test compound or vehicle (distilled water) is injected into the proximal duodenum. The doses of test compound used should be 0.01–20 mg/kg body weight. The incisions are then closed and the rats allowed to recover from the anesthesia. Two hours after the ligation, the rats are sacrificed and the gastric fluid collected and cleared by centrifugation. Total volume of secretion is determined by weight, and acidity is determined by titration to pH 7.0 with 0.1 N sodium hydroxide using an automatic titrator. The data from two experiments are then pooled. A group of rats treated with 10 mg/kg of of the anti-secretory histamine $H_2$-receptor antagonist cimetidine may be included as a positive control. Statistical evaluations can be made using Student's t-test.

In vitro activity for relaxation of contracted ileum from isolated guinea pig ileum is determined according to the following procedures. Fresh, isolated segments of guinea pig ileum (about 1.5 cm in length) are mounted in tissue baths containing Tyrode's physiological salt solution at about 30° C. and aerated continuously with oxygen:carbon dioxide (95%:5%). Tissues are then equilibrated for 60–90 minutes under 4.0 gm tension in order to achieve stable baselines. Histamine is then added to the baths and in a cumulative fashion in concentrations ranging from 1 nM to 10 mM. The maximum tension generated after each addition of histamine is recorded on a Grass Physiograph (Grass Medical Instruments, Quincy, Mass.). The tissues are then washed with several changes of Tyrode's solution, basal tension is readjusted to 4.0 gm, and a stable baseline is then again obtained. Each tissue is then exposed to a single concentration of a test compound (1 nM-10 mM) or vehicle and, after a thirty minute equilibration period, the histamine dose response curve is then repeated. Results from multiple experiments are standardized (0–100%) to the maximum response of the control tissues and plotted as percent maximum tension vs. the log of the histamine concentration in the absence and presence of the test compound.

Assay 7

Protection Against Gastric Ulceration

Food (but not water) is withheld from female Sprague-Dawley rats (Charles River, Wilmington, Mass.) weighing 70–120 g. Access is then permitted to food for ninety minutes. A single dose of test compound is then administered p.o. (0.01–20 mg/kg in a dosing volume of 1 ml/100 g), and indomethacin (Sigma Chemical Co., St. Louis, Mo.) (60 mg/kg, 1 ml/100 g body weight) is then injected subcutaneously. Control rats receive the subcutaneous injection of indomethacin and oral administration of vehicle (0.5% methyl cellulose in distilled water) for the β-adrenoceptor agonist. The animals are then allowed continued access to food but water is withdrawn. The animals are then sacrificed by cervical dislocation six hours after dosing with indomethacin. The stomach are then removed, opened along the greater curvature and washed in 0.9% saline. An assessment of gastric damage is carried out by an observer who is unaware of the dosing regimen. A transparent plastic grid divided into 1 mm² sections is placed over the antrum and the area of macroscopic damage assessed as the total area of visible lesions in mm². This value is then expressed as a percentage of the total antral area.

Assay 8

Anti-Depressant Activity

Male CD1 mice weighing between 20 and 25 g, and Sprague-Dawley rats weighing between 200 and 250 g are obtained from Charles River, Wilmington, Mass. Test compounds of Formula (I) are dissolved in water. The compounds are administered to mice in a volume of 10 ml/kg, and to rats in a volume of 2 ml/kg. Control animals receive the vehicle. Positive test results for the following parameters indicate anti-depressant activity.

(1) Antagonism of Hypothermia Induced by Reserpine

Mice are administered reserpine (2.5 mg/kg i.p. dissolved in 1% citric acid). Their rectal temperatures are measured three and one-half hours later. The mice are then divided into different groups so as to obtain the same mean rectal temperature in each group. One-half hour later, (i.e., four hours after reserpine administration), the mice are given the vehicle or test compound. Rectal temperature is measured again ninety minutes later (i.e., five hours and thirty minutes after reserpine administration) (Bourin, et al., The Value of the Reserpine Test in Psychopharmacology, Arzneim. Forsch., 33, 1173, (1983)).

(2) Antagonism of Hypothermia Induced by Apomorphine

One-half hour after the mice are placed in individual cages, their rectal temperatures are recorded. The animals are allocated so as to obtain the same mean rectal temperature in each group. Apomorphine (16 mg/kg s.c.) is given thirty minutes after the test compound or vehicle. Rectal temperature is then measured again thirty minutes after the apomorphine treatment (Puech, et al., Antagonism of Hypothermia and Behavioral Response to Apomorphine; A Simple, Rapid, and Discriminating Test for Screening Anti-Depressants and Neuroleptics, Psychopharmacology, 75, 84, (1981)).

(3) Effect on Learned Helplessness Behavior

This test is performed essentially as described by Giral, et al., Reversal of Helpless Behavior in Rats by Putative 5-HT$_{1A}$ Agonists, Biol. Psychiat., 23, 237 (1988). Electric footshocks are delivered to male albino Sprague-Dawley rats placed in chambers (20×10×10) with Plexiglass® walls and covers. The floors are made of stainless-steel grids (1.5 cm mesh). A constant-current shock is delivered as sixty scrambled, randomized inescapable shocks (15 sec. duration, 0.8 mA, every 60+15 sec.) to the grid floor. Control rats are then placed in identical chambers, but no shock is administered. All preconditioning trials are performed on Day 1 between 9 and 11 a.m. Avoidance training is initiated 48 h (Day 3) after inescapable shock in automated two-way shuttle boxes (60×21×30 cm) with Plexiglass® walls and a floor consisting of stainless-steel rods spaced 1.0 cm apart in order to evaluate escape deficits. Each shuttle box is divided into two chambers of equal size by a stainless-steel partition with a gate providing access to the adjacent compartment through a 7×7 cm space. Shuttle box sessions are performed for three consecutive days (Days 3, 4, and 5). The animals are placed individually in the shuttle box and allowed to habituate to the environment for five minutes (for the first session only) and then subjected to thirty trials. The intertrial interval should be thirty seconds. A light signal, used as a conditioned stimulus, is presented during the first three seconds of each trial. Crossing the gate into the other compartment of the box during this "conditioned stimulus only" period (referred to as avoidance response) allows rats to avoid shocks. A period with conditioned stimulus plus foot-shock (0.8 mA) may be presented if an avoidance response does not occur. Crossing the gate into the other compartment during this conditioned stimulus plus shock period is referred to as an escape response. Absence of escape response during the three-second duration conditioned stimulus plus shock is considered to be an escape failure.

The rats (n=10 per group) are treated randomly according to one of the following protocols: the control sample, which receives no shock, and is given only vehicle, or experimental animals with inescapable shock are treated daily with vehicle or test compound. Animals are treated orally over five consecutive days, i.e. six hours after shock pretreatment on Day 1, and then twice per day, a half dose in the morning (30 minutes before shuttle box session) and half a dose in the afternoon (except on day 5). Statistical analysis is performed on the mean number of escape failures using a two-way analysis of variance (subjects×sessions) followed by Dunnett's test.

Assay 9

Bronchial Relaxation and Ciliary Motility

In vitro activity of the compounds of Formula (I) for the treatment of airway inflammatory disorders, such as asthma and obstructive lung disease, may be determined by measurement of guinea pig bronchial ring relaxation according to the following procedure.

Guniea pig bronchial rings are obtained from tricolored guinea pigs of either sex (250–350 g), anesthized with urethane (1.25 g/kg) and suspended under an initial tension of 2.0 g in Krebs solution at 37° C. gassed with 95% oxygen:5% carbon dioxide. After about one hour of equilibration, the guinea pig bronchial rings are contracted with acetylcholine (10–3 M), relaxed to maximal relaxation with theophylline (10–3 M), and then allowed to equilibrate for a further sixty minutes while they are washed with Krebs solution every fifteen minutes.

Changes in tension are measured isometrically with strain guages and amplifiers and displayed on a recorder. The composition of the Krebs solution is (mM):NaCl 118.0, FCl 5.4, CaCl$_2$, 2.5, KHPO$_4$ 1.2, MgSO$_4$ 1.2, NaHCO$_3$ 25.0, and glucose 11.7.

To test effects of test compounds on resting tension, cumulative concentration-response curves are obtained by addition of the test compounds ($10^{-9}$–$10^{-6}$ M) every ten to twenty minutes until a plateau is reached. The relaxant effects of the test compounds are expresed as percentages of the maximal relaxations induced by theophylline ($3\times10^{-3}$ M).

Assay 10

Prostate Disease

Ventral prostates of male Sprague-Dawley rats (300–400 g) anesthetized with diethyl ether are quickly excised and placed in oxygenated Krebs solution. While maintained at room temperature in this buffer, adherent fatty and connective tissues are removed. The prostates are then suspended in 10 ml organ baths containing Krebs solution warmed to 37° C. and aerated with a mixture of 95% oxygen and 5% carbon dioxide. The composition of the Krebs solution is 118.4 mM NaCl, 4.7 mM KCl, 1.2 mM $MgSO_4$, 2.5 mM $CaCl_2$, 11.1 mM dextrose, 25.0 mM $NaHCO_3$ and 1.2 mM $KH_2PO_4$, dissolved in distilled and demineralized water. The tissues are attached to isometric force-displacement transducers and isometric contraction is recorded under a loading tension of 0.5 g. Equilibration is undertaken for one or two hours before the addition of test compounds. Submaximal contractions are first elicited by repeated concentrations of $1\times10^{-6}M$ phenylephrine until constant responses are obtained. The control and test compound-treated experiments are performed in different preparations. A concentration-response curve to cumulate concentrations of phenylephrine or acetylcholine ($10^{-9}$ to $10^{-4}M$) is determined. For testing compounds, a concentration response curve to phenylephrine or acetylcholine is determined in the presence of the compounds.

In vitro activity of compounds of Formula (I) can also be determined for specific efficacy in human prostate as follows.

Prostatic tissue specimens are obtained from patients with symptomatic BPH, who are undergoing open prostatectomy. Isolated human prostatic tissue is cut into five to eight strips (3 mm wide, 3 mm thick and 15 mm long in each strip). The strips are mounted vertically in organ baths containing 20 ml Krebs-Henseleit solution of the following composition (mM): NaCl 112, KCl 5.9, $MgCl_2$ 1.2, $CaCl_2$ 2, $NaHCO_3$ 25, $NaHPO_4$ 1.2, glucose 11.5. The medium is maintained at 37° C. and at pH 7.4, and is equilibrated with a gas mixture consisting of 95% oxygen and 5% carbon dioxide. A resting tension of 0.5 g is applied and the responses are recorded isometrically through a force-displacement transducer. The preparations are equilibrated for ninety minutes before starting the experiments.

Concentration-response curves for phenylephrine or acetylcholine ($10^{-9}$ to $10^{-4}M$) are determined by adding the compound directly to the bathing media in a cumulative fashion. For testing compounds, the prostate strips are incubated in the presence of compound (1 or 10 $\mu M$) for thirty minutes before and then phenylephrine or acetylcholine are added to the medium in a cumulative fashion to obtain to the concentration-response curve in the presence of the compound.

Assay 11

Effect on Triglyceride Levels and Dyslipidemia

Compounds of the Formula (I) lower triglyceride levels and cholesterol levels and raise high density lipoprotein levels and are therefore of use in combating medical conditions wherein such lowering (and raising) is thought to be beneficial. Thus, the compounds of Formula (I) can be used in the treatment of hypertriglyceridaemia, hypercholesterolemia, and conditions of low HDL (high density lipoprotein) levels in addition to the treatment of atherosclerotic disease such as of coronary, cerebrovascular and peripheral arteries, cardiovascular disease and related conditions.

Activity of compounds of Formula (I) for dyslipidemia can be determined according to the following procedure. C57BL/6J ob/ob mice (male, 30–40 g body weight, Jackson Lab, Bar Harbor, Me.), housed 5 mice per cage in an environmentally controlled room, are dosed once or twice daily for three weeks with test compound (0.01–20 mg/kg, n=15 per group) or vehicle (0.5% w/v methyl cellulose/distilled water, water, or other suitable vehicle) by oral gavage. At the end of the study, twenty-four hours after giving the final dose of compound, the mice are sacrificed by decapitation and blood collected. Plasma concentrations of free fatty acids and triglyceride are determined using a clinical autoanalyzer (Abbott Spectrum® CCx; Abbott Laboratories, Abbott Park, Ill.).

Assay 12

Decrease in Body Fat

Activity of compounds of Formula (I) for decrease in body fat can be determined according to the following procedure. C57BL/6J ob/ob mice (male, 30–40 g body weight, Jackson Lab, Bar Harbor, Me.) are housed five mice per cage in an environmentally controlled room with food (pelleted rodent chow) and water available ad libitum. The compound or vehicle (0.5% w/v methyl cellulose/distilled water, water, or other suitable vehicle) is dosed once or twice daily for three weeks (0.01–20 mg/kg, n=15 per group) by oral gavage. Body weight of each mouse is measured daily and food intake per cage determined by weighing the amount of food left in the trough. At the end of the study, twenty-four hours after giving the final dose of compound, the mice are weighed and then sacrificed by cervical dislocation. The epididymal fat pads from each mouse are excised and weighed. The fat versus body weight ratio is determined for each mouse using the absolute body weights and the fat pad weights. A reduction in fat pad weight is indicative of a reduction in total body fat.

What is claimed is:

1. A compound of Formula (I)

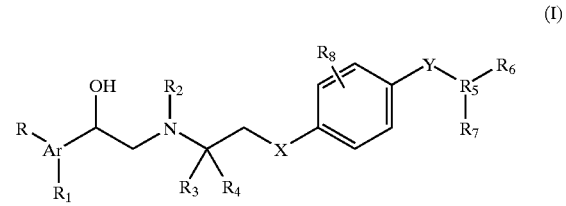

the stereoisomers thereof, and the pharmaceutically acceptable salts of said compounds, stereoisomers, wherein:

Ar is pyridyl;

R is hydrogen, hydroxy, halogen, —$CF_3$, —($C_1$–$C_6$)alkyl, —($C_1$–$C_6$)alkoxy, —($C_3$–$C_8$)cycloalkyl, —$NR_9R_{10}$, —$NR_9SO_2R_{10}$, —$NR_9COR_{10}$, or —$SO_2R_9$;

$R_1$ is hydrogen, —($C_1$–$C_6$)alkyl, halogen, —($C_1$–$C_6$)alkoxy, or hydroxy;

$R_2$, $R_3$, $R_4$ are, independently, hydrogen, or —($C_1$–$C_6$)alkyl;

$R_5$ is a aromatic 5-membered ring heterocycle having from 1 to 4 heteroatoms selected from the group consisting of oxygen, sulfur, or nitrogen;

$R_6$ and $R_7$ are, independently, hydrogen, halogen, cyano, oxo, —($C_1$–$C_6$)acyl, —$CO_2R_9$, —$NR_9R_{10}$, hydroxy, —($C_1$–$C_6$)alkoxy, —$CONR_9R_{10}$, —$NR_9SO_2R_{10}$, —$SO_2NR_9R_{10}$, or —$SO_2R_9$; —($C_1$–$C_6$)alkyl, optionally substituted with —($C_3$–$C_8$)cycloalkyl, halogen, aryl, —($C_1$–$C_6$)alkoxy, —($C_1$–$C_6$)haloalkyl, alkylalkoxy, hydroxy, —$NR_9R_{10}$, —$NR_9SO_2R_{10}$, —$SO_2NR_9R_{10}$, —$SO_2R_9$, or heterocycle; —($C_3$–$C_8$) cycloalkyl, optionally substituted with —($C_1$–$C_6$)alkyl, —($C_3$–$C_8$)cycloalkyl, halogen, aryl, —($C_1$–$C_6$)alkoxy, —(C₁–C₆)haloalkyl, alkylalkoxy, hydroxy, —NR₉R₁₀, —NR₉SO₂R₁₀, —SO₂NR₉R₁₀, —SO₂R₉, or heterocycle; aryl, optionally substituted with —(C₁–C₆)alkyl, —(C₃–C₇)cycloalkyl, halogen, aryl, —(C₁–C₆)alkoxy, —(C₁–C₆)haloalkyl, alkylalkoxy, hydroxy, —NR₉R₁₀, —NR₉SO₂R₁₀, —SO₂NR₉R₁₀, —SO₂R₉, or heterocycle; or heterocycle, optionally substituted with —(C₁–C₆)alkyl, —(C₃–C₈)cycloalkyl, halogen, aryl, —(C₁–C₆)alkoxy, —(C₁–C₆)haloalkyl, alkylalkoxy, hydroxy, —NR₉R₁₀, —NR₉SO₂R₁₀, —SO₂NR₉R₁₀, —SO₂R₉, or heterocycle;

R₈ is hydrogen, —(C₁–C₄)alkyl, or halogen; and

R₉ and R₁₀ are, independently, hydrogen, —(C₁–C₆)alkyl, alkylalkoxy, —(C₃–C₈)cycloalkyl, —(C₁–C₆)haloalkyl, —(C₁–C₆)alkoxy, aryl, or heterocycle;

X is a direct bond or oxygen; and

Y is a direct bond, —(C₁–C₆)alkyl, —OCH₂—, —CH₂O—, or oxygen.

2. A compound according to claim 1, wherein Ar is pyridyl; R, R₁, R₂, R₃, R₄, and R₈ are hydrogen; X is oxygen; Y is a direct bond; and R₅ is an aromatic 5-membered ring heterocycle selected from the group consisting of imidazolyl, isothiazolyl, isoxazolyl, oxadiazolyl, oxazolyl, pyrazolyl, thiadiazolyl, thiazolinyl, and triazolyl.

3. A compound according to claim 2 selected from the group consisting of:

(R)-2-{2-[4-(4-benzofuran-2-yl-thiazol-2-yl)-phenoxy]-ethylamino}-1-pyridin-3-yl-ethanol;

(R)-2-{2-[4-(2-benzyloxymethyl-oxazol-4-yl)-phenoxy]-ethylamino}-1-pyridin-3-yl-ethanol;

(R)-2-{2-[4-(2-butyl-thiazol-4-yl)-phenoxy]-ethylamino}-1-pyridin-3-yl-ethanol;

(R)-2-{2-[4-(2-tert-butyl-thiazol-4-yl)-phenoxy]-ethylamino}-1-pyridin-3-yl-ethanol;

(R)-2-{2-[4-(2-cyclopentyl-thiazol-4-yl)-phenoxy]-ethylamino}-1-pyridin-3-yl-ethanol;

(R)-2-{2-[4-(2,5-dimethyl-oxazol-4-yl)-phenoxy]-ethylamino}-1-pyridin-3-yl-ethanol;

(R)-2-(2-{4-[2-(2-ethyl-pyridin-4-yl)-thiazol-4-yl]-phenoxy}-ethylamino)-1-pyridin-3-yl-ethanol;

(R)-2-{2-[4-(2-ethyl-oxazol-4-yl)-phenoxy]-ethylamino}-1-pyridin-3-yl-ethanol;

(R)-2-{2-[4-(4-ethyl-thiazol-2-yl)-phenoxy]-ethylamino}-1-pyridin-3-yl-ethanol;

(R)-2-{2-[4-(2-ethyl-thiazol-4-yl)-phenoxy]-ethylamino}-1-pyridin-3-yl-ethanol;

(R)-2-{2-(4-(2-hydroxymethyl-oxazol-4-yl)-phenoxy]-ethylamino}-1-pyridin-3-yl-ethanol;

(R)-2-[2-(4-imidazol-1-yl-phenoxy)-ethylamino]-1-pyridin-3-yl-ethanol;

(R)-2-{2-[4-(2-isopropyl-1H-imidazol-4-yl)-phenoxy]-ethylamino}-1-pyridin-3-yl-ethanol;

(R)-2-{2-[4-(2-isopropyl-oxazol-4-yl)-phenoxy]-ethylamino}-1-pyridin-3-yl-ethanol;

(R)-2-{2-(4-(2-isopropyl-thiazol-4-yl)-phenoxy]-ethylamino}-1-pyridin-3-yl-ethanol;

(R)-2-{2-[4-(2-methoxymethyl-oxazol-4-yl)-phenoxy]-ethylamino}-1-pyridin-3-yl-ethanol;

(R)-2-(2-{4-[2-(4-methoxy-phenyl)-thiazol-4-yl]-phenoxy}ethylamino)-1-pyridin-3-yl-ethanol;

(R)-2-{2-[4-(2-methyl-1H-imidazol-4-yl)-phenoxy]-ethylamino}-1-pyridin-3-yl-ethanol;

(R)-2-{2-[4-(5-methyl-[1,3,4]oxadiazol-2-yl)-phenoxy]-ethylamino}-1-pyridin-3-yl-ethanol;

(R)-2-{2-[4-(2-methyl-oxazol-4-yl)-phenoxy]-ethylamino}-1-pyridin-3-yl-ethanol;

(R)-2-{2-[4-(5-methyl-oxazol-4-yl)-phenoxy]-ethylamino}-1-pyridin-3-yl-ethanol;

(R)-2-(2-{4-[2-(2-methyl-propane-2-sulfonylmethyl)-thiazol-4-yl]phenoxy}-ethylamino)-1-pyridin-3-yl-ethanol;

(R)-2-{2-[4-(1-methyl-1H-pyrazol-3-yl)-phenoxy]-ethylamino}-1-pyridin-3-yl-ethanol;

(R)-2-{2-[4-(4-methyl-thiazol-2-yl)-phenoxy]-ethylamino}-1-pyridin-3-yl-ethanol;

(R)-2-{2-[4-(2-methyl-thiazol-4-yl)-phenoxy]-ethylamino}-1-pyridin-3-yl-ethanol;

(R)-2-{2-[4-(5-methyl-4H-[1,2,4]triazol-3-yl)-phenoxy]-ethylamino}-1-pyridin-3-yl-ethanol;

(R)-2-{2-[4-(2'-methyl-(2,4']bithlazolyl-4-yl)-phenoxy]-ethylamino}-1-pyridin-3-yl-ethanol;

(R)-2-[2-(4-oxazol-4-yl-phenoxy)-ethylamino]-1-pyridin-3-yl-ethanol;

(R)-2-[2-(4-oxazol-5-yl-phenoxy)-ethylamino]-1-pyridin-3-yl-ethanol;

(R)-2-{2-[4-(2-phenyl-1H-imidazol-4-yl)-phenoxy]-ethylamino}-1-pyridin-3-yl-ethanol;

(R)-2-{2-[4-(2-phenyl-thiazol-4-yl)-phenoxy]-ethylamino}-1-pyridin-3-yl-ethanol;

(R)-2-{2-[4-(4-phenyl-thiazol-2-yl)-phenoxy]-ethylamino}-1-pyridin-3-yl-ethanol;

(R)-2-{2-[4-(2-propyl-thiazol-4-yl)-phenoxy]-ethylamino}-1-pyridin-3-yl-ethanol;

(R)-2-{2-[4-(1H-pyrazol-3-yl)-phenoxy]-ethylamino}-1-pyridin-3-yl-ethanol;

(R)-1-pyridin-3-yl-2-{2-[4-(2-pyridin-3-yl-1H-imidazol-4-yl)-phenoxy]-ethylamino}-ethanol;

(R)-1-pyridin-3-yl-2-{2-[4-(2-pyridin-4-yl-1H-imidazol-4-yl)-phenoxy]-ethylamino}-ethanol;

(R)-1-pyridin-3-yl-2-{2-[4-(2-pyridin-3-yl-thiazol-4-yl)-phenoxy]-ethylamino}-ethanol;

(R)-1-pyridin-3-yl-2-{2-[4-(2-pyridin-4-yl-thiazol-4-yl)-phenoxy]-ethylamino}-ethanol;

(R)-1-pyridin-3-yl-2-(2-(4-thiazol-2-yl-phenoxy)-ethylamino]-ethanol (R)-1-pyridin-3-yl-2-[2-(4-thiazol-4-yl-phenoxy)-ethylamino]-ethanol;

(R)-1-pyridin-3-yl-2-{2-[4-(2-thiophen-2-yl-1H-imidazol-4-yl)-phenoxy]-ethylamino}-ethanol;

(R)-1-pyridin-3-yl-2-{2-[4-(2-thiophen-2-yl-thiazol-4-yl)-phenoxy]-ethylamino}-ethanol;

(R)-1-pyridin-3-yl-2-{2-[4-(4-p-tolyl-thiazol-2-yl)-phenoxy]-ethylamino}-ethanol;

(R)-1-pyridin-3-yl-2-{2-[4-(2-p-tolyl-thiazol-4-yl)-phenoxy]-ethylamino}-ethanol;

(R)-1-pyridin-3-yl-2-{2-[4-(2-trifluoromethyl-1H-imidazol-4-yl)-phenoxy]-ethylamino}-ethanol;

(R)-1-pyridin-3-yl-2-(2-{4-[2-(4-trifluoromethyl-phenyl)-thiazol-4-yl]-phenoxy}-ethylamino)-ethanol;

(R)-1-pyridin-3-yl-2-{2-[4-(4-trifluoromethyl-thiazol-2-yl)-phenoxy]-ethylamino}-ethanol; and (R)-1-pyridin-3-yl-2-{2-[4-(2-trifluoromethyl-thiazol-4-yl)-phenoxy]-ethylamino}-ethanol;

a stereoisomer thereof, or a pharmaceutically acceptable salt of said compound or stereoisomer.

4. A compound according to claim 3 selected from the group consisting of:

(R)-2-{2-[4-(ethyl-thiazol-2-yl)-phenoxy]-ethylamino}-1-pyridin-3-yl-ethanol;

(R)-2-{2-[4-(2-methoxymethyl-oxazol-4-yl)-phenoxy]-ethylamino}-1-pyridin-3-yl-ethanol;

(R)-2-{2-[4-(2-methyl-oxazol-4-yl)-phenoxy]-ethylamino}-1-pyridin-3-yl-ethanol;

(R)-2-{2-[4-(2-methyl-thiazol-4-yl)-phenoxy]-ethylamino}-1-pyridin-3-yl-ethanol;

(R)-2-[2-(4-oxazol-4-yl-phenoxy)-ethylamino]-1-pyridin-3-yl-ethanol;

(R)-2-{2-[4-(1H-pyrazol-3-yl)-phenoxy]-ethylamino}-1-pyridin-3-yl-ethanol;

(R)-1-pyridin-3-yl-2-[2-(4-thiazol-2-yl-phenoxy)-ethylamino]-ethanol;

(R)-1-pyridin-3-yl-2-[2-(4-thiazol-4-yl-phenoxy)-ethylamino]-ethanol; and (R)-1-pyridin-3-yl-2-{2-[4-(4-trifluoromethyl-thiazol-2-yl)-phenoxy]-ethylamino}-ethanol;

a stereoisomer thereof, or a pharmaceutically acceptable salt of said compound or stereoisomer.

5. A pharmaceutical composition which comprises a compound of claim 1, a stereoisomer thereof, or a pharmaceutically acceptable salt of said compound or stereoisomer, and a pharmaceutically acceptable carrier, vehicle, or diluent.

6. A method of treating obesity in a mammal in need of such treatment which method comprises administering to said mammal a therapeutically effective amount of a compound of claim 1, a stereoisomer thereof, or a pharmaceutically acceptable salt of said compound or stereoisomer.

7. A method of treating obesity in a mammal in need of such treatment which method comprises administering to said mammal a therapeutically amount of a composition of claim 5.

* * * * *